(12) United States Patent
Pan et al.

(10) Patent No.: US 10,189,812 B2
(45) Date of Patent: Jan. 29, 2019

(54) BI-BENZYL ISOQUINOLINE DERIVATIVE, PREPARATION METHOD AND USE THEREOF IN HEPATOPATHY TREATMENT AND PREVENTION

(71) Applicants: THE KEY LABORATORY OF CHEMISTRY FOR NATURAL PRODUCTS OF GUIZHOU PROVINCE AND CHINESE ACADEMY OF SCIENCES, Guiyang (CN); VERSITECH LTD., Hong Kong (CN)

(72) Inventors: Weidong Pan, Guiyang (CN); Yibin Feng, Hong Kong (CN); Yazhou Liu, Guiyang (CN); Ning Wang, Hong Kong (CN); Lan Huang, Guiyang (CN); Guangyi Liang, Guiyang (CN); Maosheng Zhang, Guiyang (CN); Tianlei Li, Guiyang (CN); Huayong Lou, Guiyang (CN); Zhanxing Hu, Guiyang (CN); Sheng Liu, Guiyang (CN); Peixue Cao, Guiyang (CN); Jinghua Ruan, Guiyang (CN); Junjie Lan, Guiyang (CN); Chao Chen, Guiyang (CN)

(73) Assignees: THE KEY LABORATORY OF CHEMISTRY FOR NATURAL PRODUC, Guiyang (CN); VERSITECH LIMITED, Hong Kong (CN)

( * ) Notice: Subject to any disclaimer, the term of this patent is extended or adjusted under 35 U.S.C. 154(b) by 0 days.

(21) Appl. No.: 15/504,245

(22) PCT Filed: Jun. 29, 2015

(86) PCT No.: PCT/CN2015/082626
§ 371 (c)(1),
(2) Date: Feb. 15, 2017

(87) PCT Pub. No.: WO2016/023404
PCT Pub. Date: Feb. 18, 2016

(65) Prior Publication Data
US 2017/0260161 A1    Sep. 14, 2017

(30) Foreign Application Priority Data
Aug. 15, 2014  (CN) .......................... 2014 1 0403363

(51) Int. Cl.
*C07D 491/18*  (2006.01)
*A61K 31/4748* (2006.01)
*C07D 401/12*  (2006.01)
*C07D 405/14*  (2006.01)
*C07D 409/14*  (2006.01)
*C07D 491/16*  (2006.01)

(52) U.S. Cl.
CPC ......... *C07D 401/12* (2013.01); *C07D 405/14* (2013.01); *C07D 409/14* (2013.01); *C07D 491/16* (2013.01); *C07D 491/18* (2013.01)

(58) Field of Classification Search
CPC .................................................. C07D 491/18
See application file for complete search history.

(56) References Cited

U.S. PATENT DOCUMENTS 6,617,335 B1    9/2003 Wang et al.

FOREIGN PATENT DOCUMENTS

| CN | 102875560 A   | 1/2013 |
| CN | 103772405 A   | 5/2014 |
| WO | 2013026383 A1 | 2/2013 |

(Continued)

OTHER PUBLICATIONS

Wolff, Manfred E. Burger's Medicinal Chemistry, 5th Ed. Part 1, pp. 975-977 (1995).*

(Continued)

*Primary Examiner* — Emily A Bernhardt
(74) *Attorney, Agent, or Firm* — Womble Bond Dickinson (US) LLP; Danielle L. Herritt; Rebecca N. Barnes

(57) ABSTRACT

The invention disclosed a compound of general formula (I), a single stereoisomer thereof, a mixture of stereoisomers thereof, and a prodrug, pharmaceutically acceptable salt and metabolite thereof, $X_1$, $X_2$, $X_3$, $X_4$, $R_1$, $R_2$, x, y and z being as defined in the present invention.

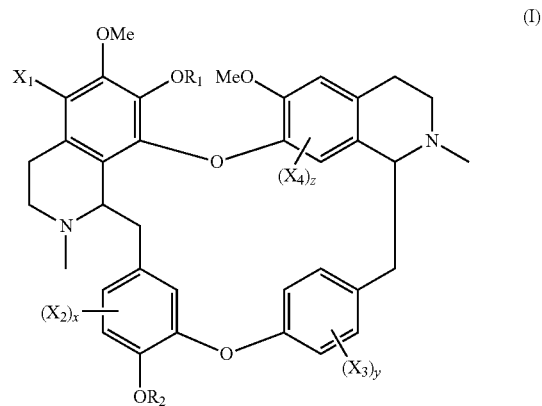

14 Claims, No Drawings

(56) References Cited

FOREIGN PATENT DOCUMENTS

WO         2013107428 A1      7/2013

OTHER PUBLICATIONS

Banker et al. "Modern Pharmaceutics", 3rd Ed. p. 596 (1996).*
Testa et al. Pure Appl. Chem. vol. 76, pp. 907-914 (2004).*
He, P., et al. "Partial synthesis and biological evaluation of bisbenzylisoquinoline alkaloids derivatives: potential modulators of multidrug resistance in cancer," Journal of Asian Natural Products Research, vol. 14, No. 6, Jun. 2012, 564-576.

\* cited by examiner

BI-BENZYL ISOQUINOLINE DERIVATIVE, PREPARATION METHOD AND USE THEREOF IN HEPATOPATHY TREATMENT AND PREVENTION

CROSS-REFERENCE TO RELATED APPLICATIONS

This application is a 371 of International Application No. PCT/CN2015/082626, filed Jun. 29, 2015, which claims priority to S.I.P.O. Patent application No. 201410403363.X filed Aug. 15, 2014, entitled "The Preparation of Bi-Benzyl Isoquinoline Derivative", the entire disclosures of which are incorporated herein by reference.

FIELD OF THE INVENTION

The present invention relates to organic chemistry and pharmaceutical chemistry in the main.

BACKGROUND OF THE INVENTION

Dibenzylisoquinoline alkaloid derivatives have all kinds of bioactivity, mainly comprising antibiosis, anti-inflammatory, anti-hypertension, anti-cancer, anti-platelet aggregation, regulating immune function, antiarrhythmia or anti-liver fibrosis etc.

Tetrandrine is also named hanfangchin A, whose chemical formula is (6,6',7,12-tetramethoxy-2,2'-dimethyl berbamine). It is one kind of dibenzylisoquinoline alkaloid derivatives, which is extracted from the rock root of fangji belonging to Chinese herbal medicine, characterized by chemical structure below:

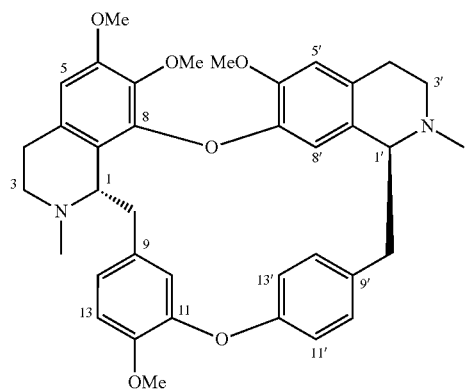 [SMILES: COc1ccc2cc1Oc1ccc(cc1)C[C@H]1c3cc(c(OC)cc3CCN1C)Oc1c(OC)c(OC)cc3c1[C@H](C2)N(C)CC3]

SUMMARY OF INVENTION

The present application relates to a compound of general formula (I), a single stereoisomer thereof, a mixture of stereoisomers thereof, and a prodrug, pharmaceutically acceptable salt and metabolite thereof:

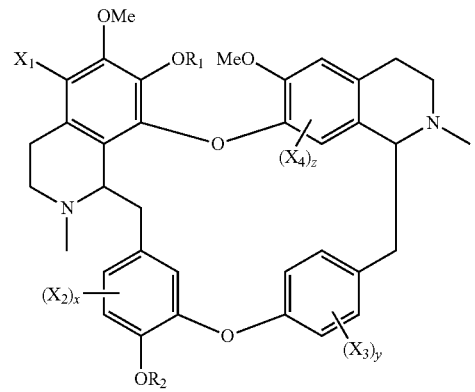

wherein, $X_1$, $X_2$, $X_3$ and $X_4$ are independently selected from hydrogen, halogen, nitro, nitroso, —$SO_3H$, optionally substituted amino or optionally substituted sulfonyl;

$R_1$ and $R_2$ are independently selected from hydrogen, nitroso, optionally substituted alkyl, optionally substituted alkenyl, optionally substituted alkynyl, optionally substituted cycloalkyl, optionally substituted sulfonyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

x is 1, 2 or 3;

y is 1, 2, 3 or 4; and z is 1 or 2;

provided that:

$X_1$, $X_2$, $X_3$ and $X_4$ are not hydrogen simultaneously, and

When one of $X_1$, $X_2$, $X_3$ and $X_4$ is halogen, the rest of $X_1$, $X_2$, $X_3$ and $X_4$ are independently selected from hydrogen, nitro, nitroso, —$SO_3H$, optionally substituted amino or optionally substituted sulfonyl, but they are not hydrogen simultaneously.

According to a further aspect, the present application relates to a compound of general formula (Ia), a single stereoisomer thereof, a mixture of stereoisomers thereof, and a prodrug, pharmaceutically acceptable salt and metabolite thereof:

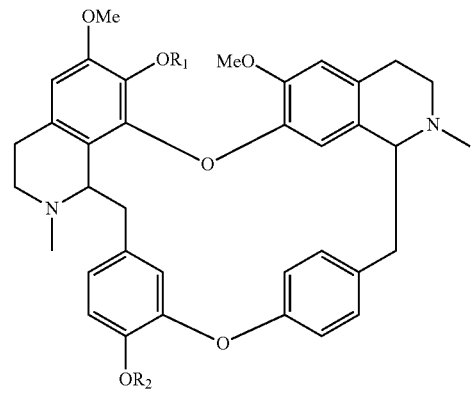

wherein, $R_1$ is selected from nitroso, optionally substituted alkyl, optionally substituted alkenyl, optionally substituted alkynyl, optionally substituted alkylcarbonyl, optionally substituted alkenylcarbonyl, optionally substituted alkynylcarbonyl, optionally substituted cycloalkylcarbonyl, optionally substituted arylcarbonyl, or optionally substituted heteroarylcarbonyl or substituted sulfonyl; and R₂ is selected from hydrogen, optionally substituted alkyl, nitroso, optionally substituted alkylcarbonyl, optionally substituted alkenylcarbonyl, optionally substituted alkynylcarbonyl, optionally substituted cycloalkylcarbonyl, optionally substituted arylcarbonyl, optionally substituted heteroarylcarbonyl or substituted sulfonyl.

According to a further aspect, the present application relates to the compounds, a single stereoisomer thereof, a mixture of stereoisomers thereof, and a prodrug, pharmaceutically acceptable salt and metabolite thereof, wherein the compounds are selected from:

H-01

H-02

H-03
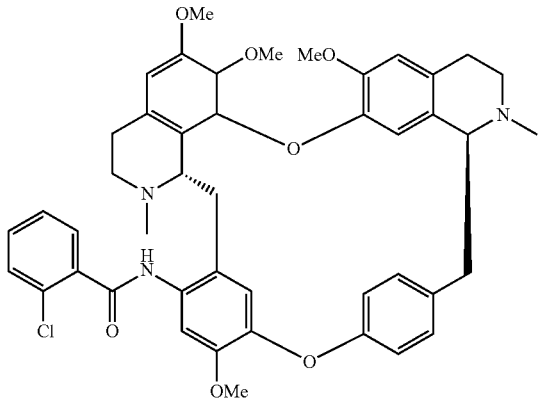

H-04
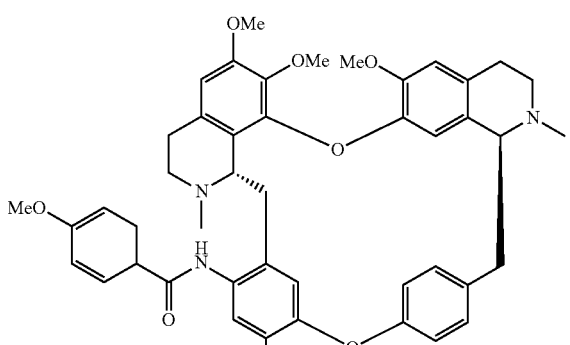

H-05
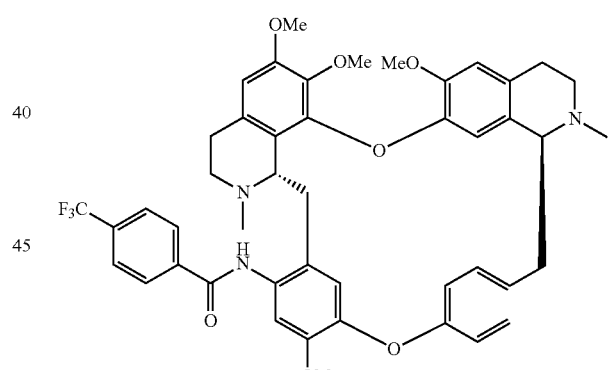

H-06
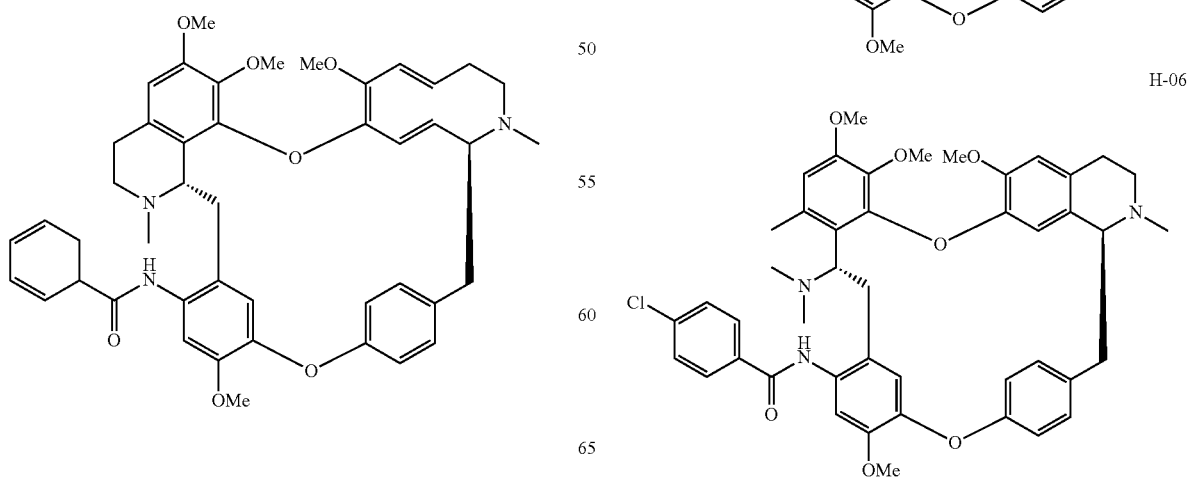

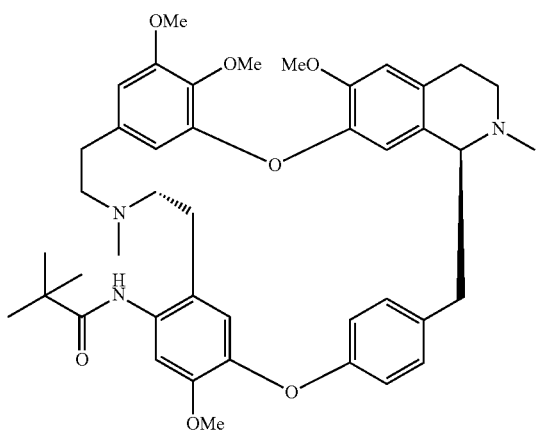
H-07
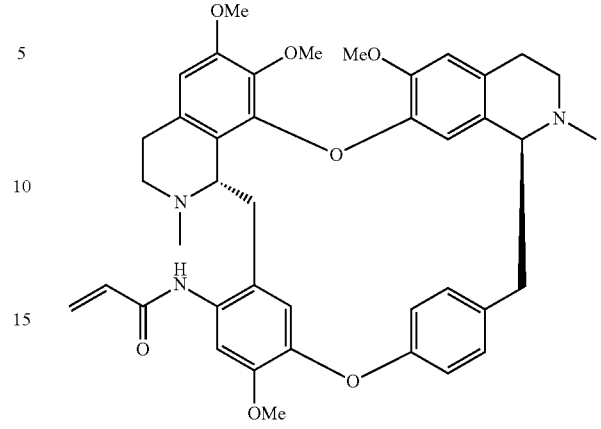
H-10
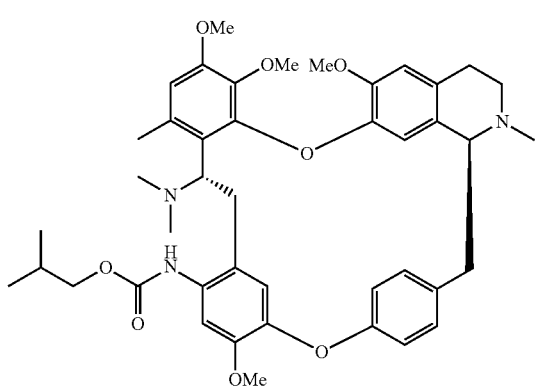
H-08
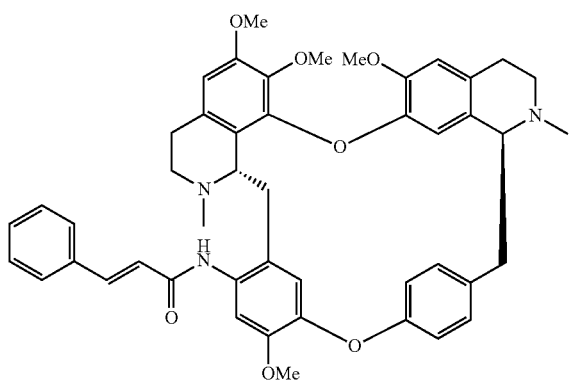
H-09
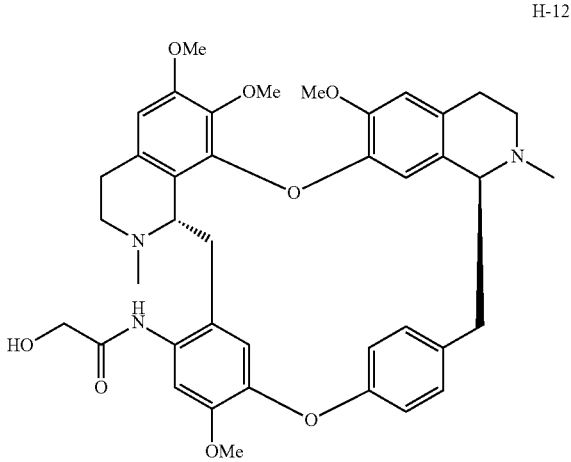
H-11
H-12

H-13
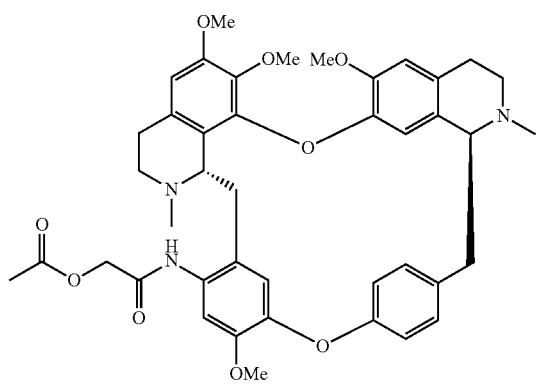
H-16
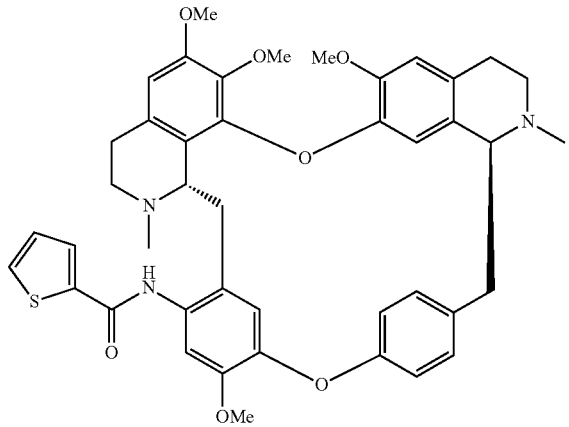
H-14
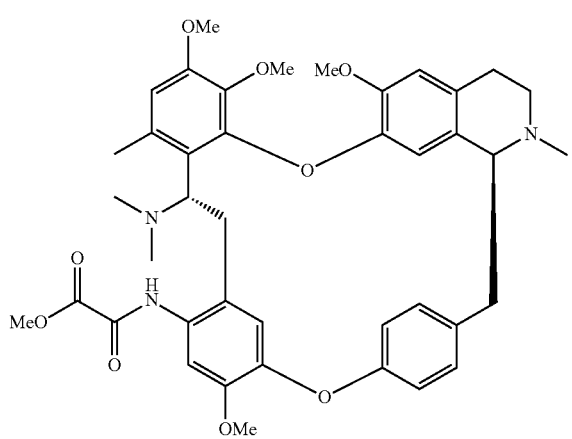
H-17
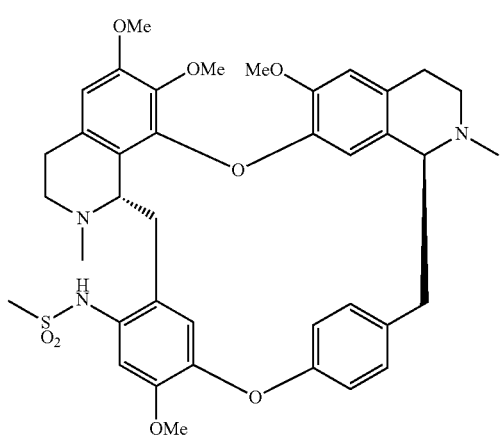
H-15
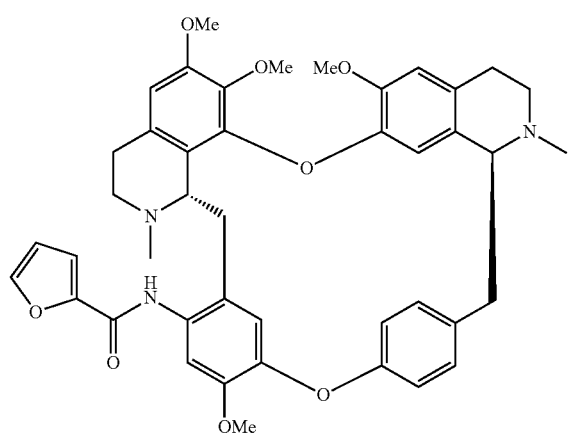
H-18
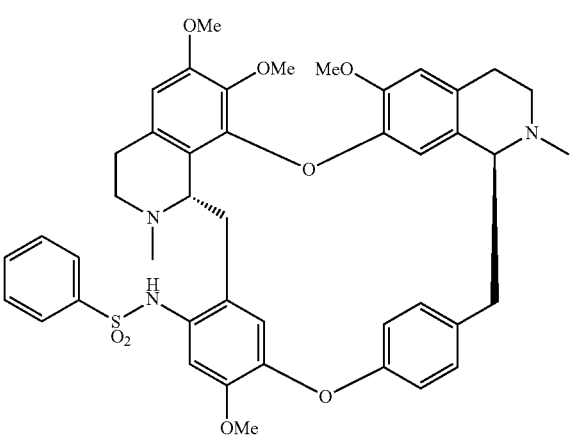

H-19
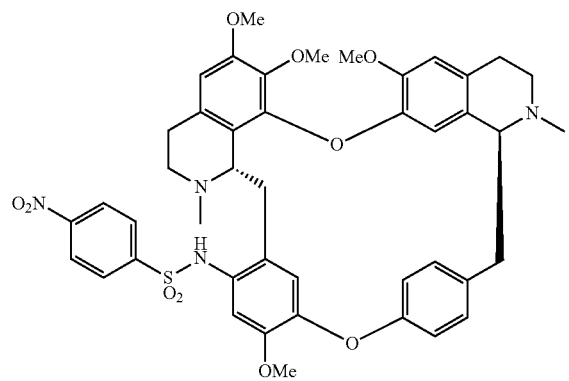
H-20
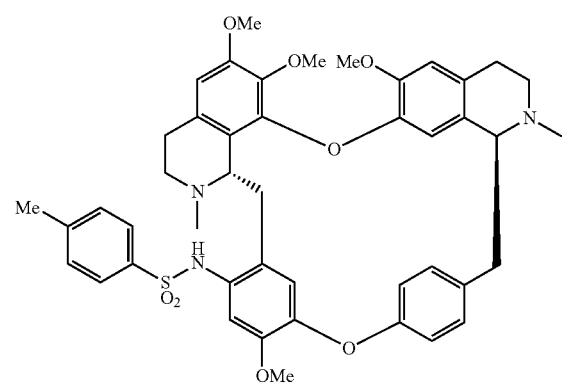
H-21
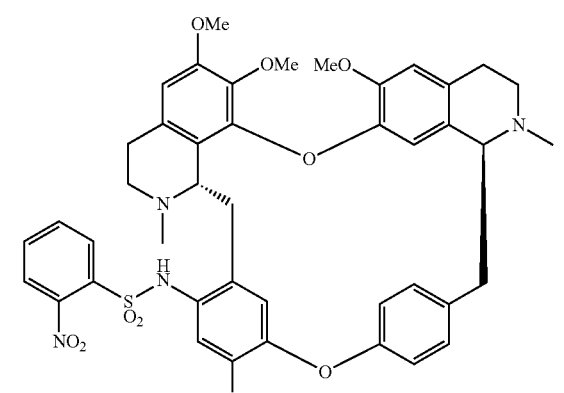
H-22
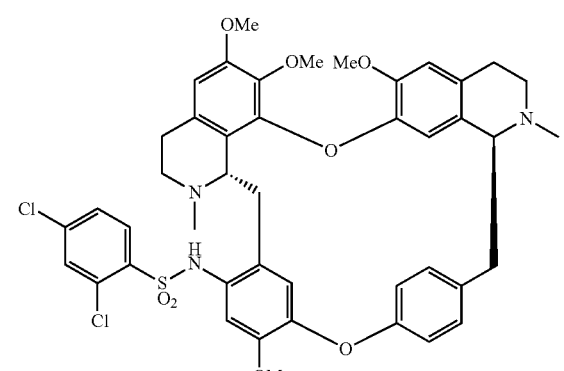
H-23
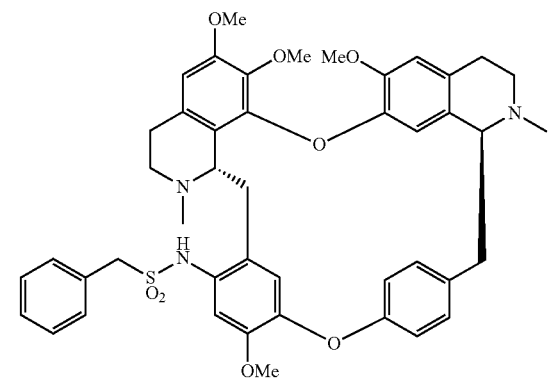
H-24
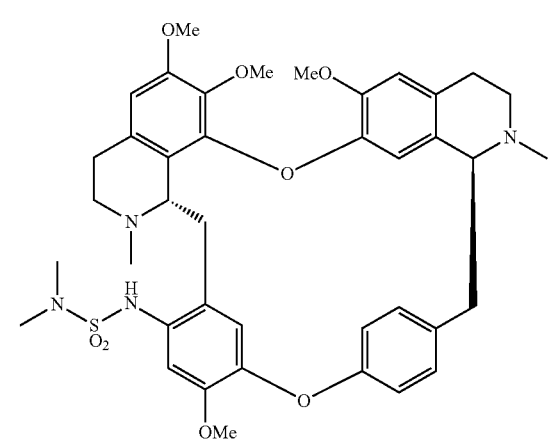
H-25

H-26
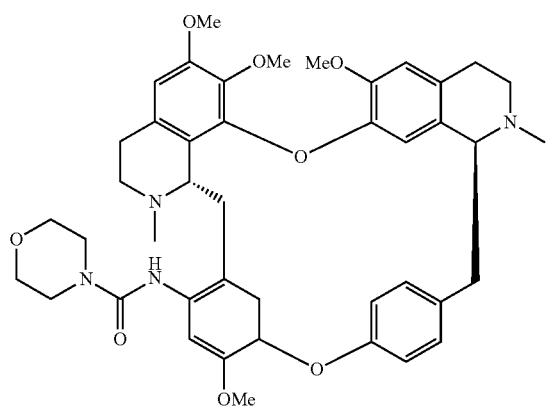
H-27
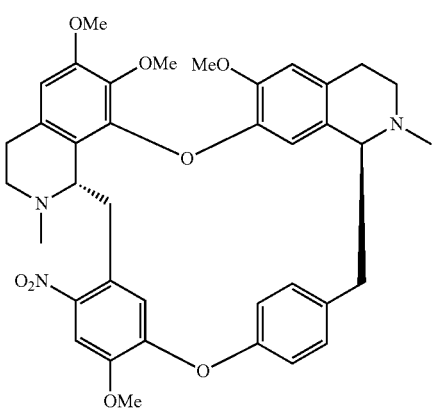
H-28
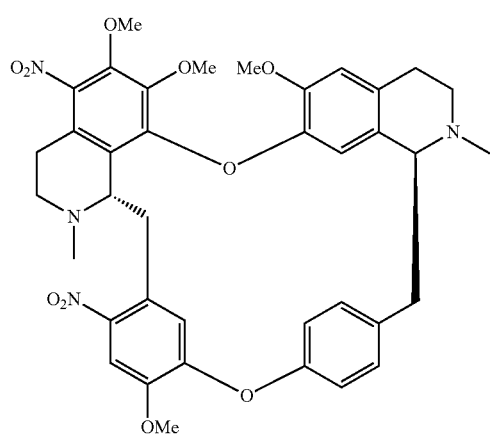
H-29
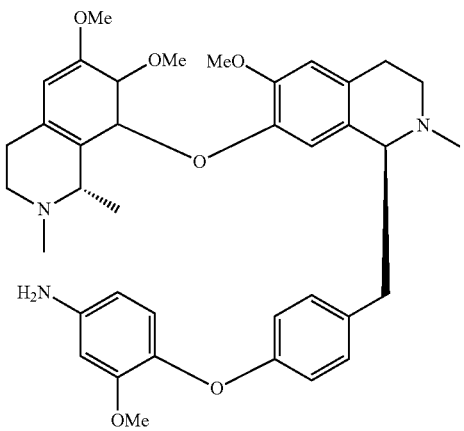
H-30
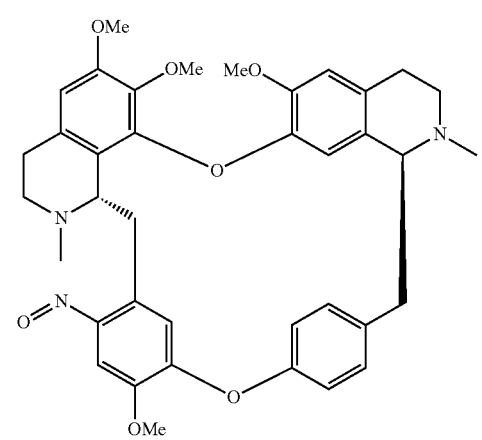
H-31
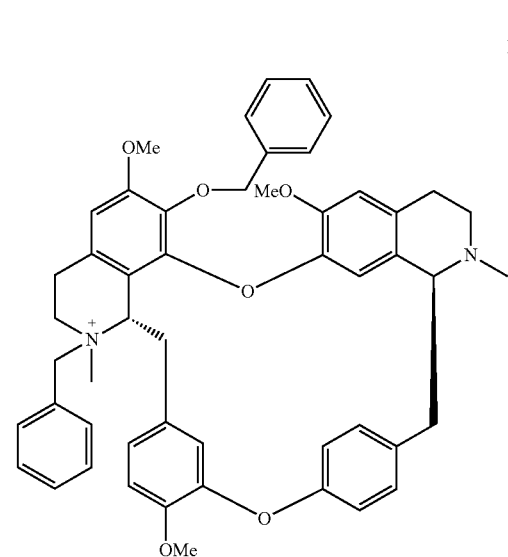

-continued
H-32
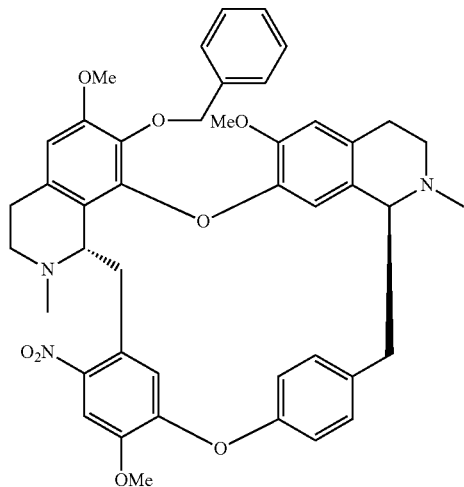
H-33
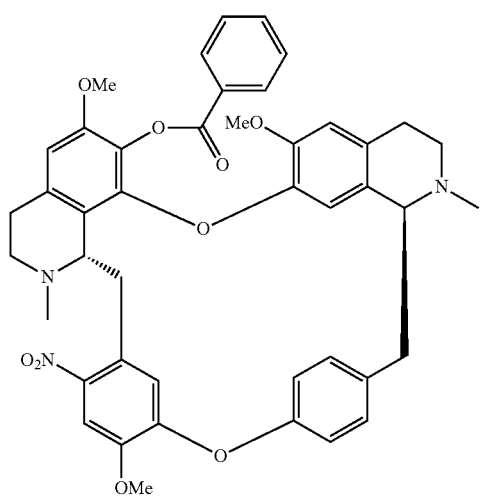
H-34
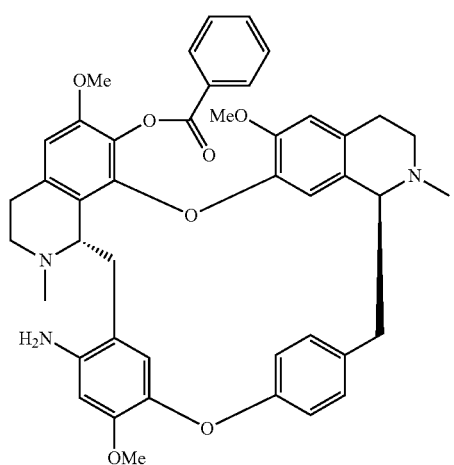
-continued
H-35
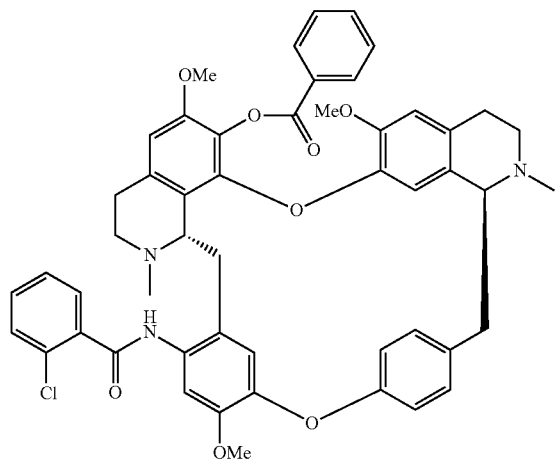
H-36
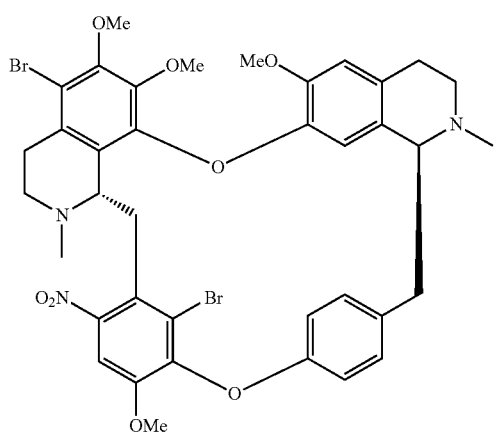
H-37
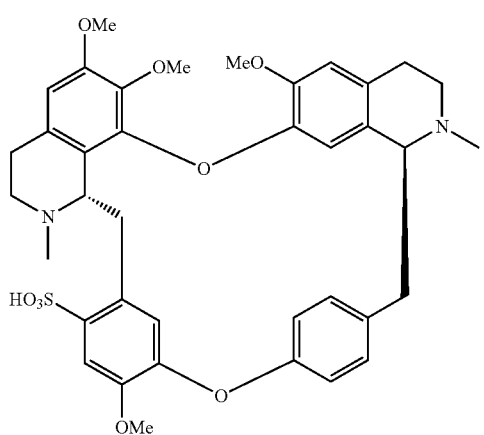

-continued
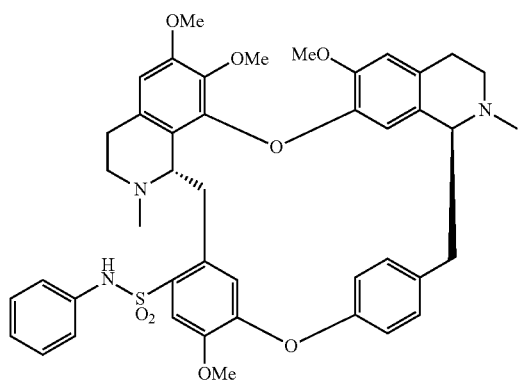
H-38
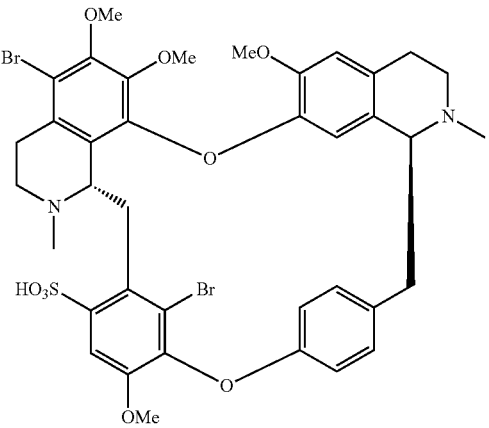
H-41
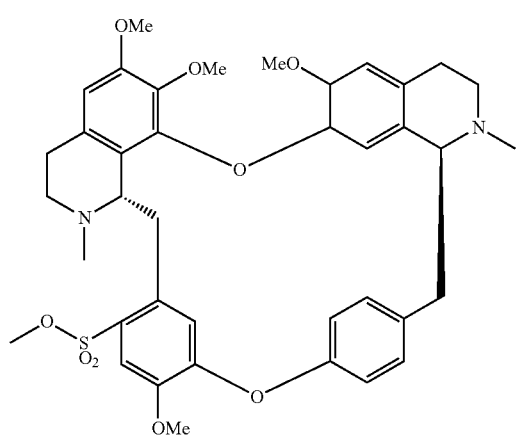
H-39
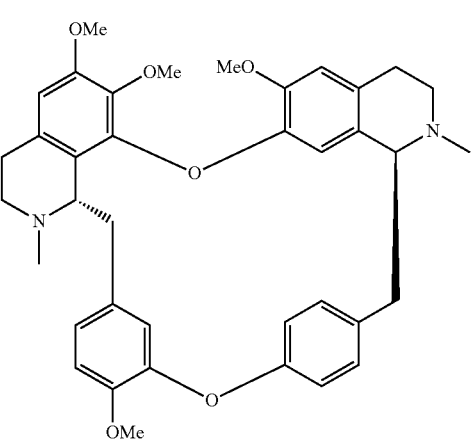
H-42
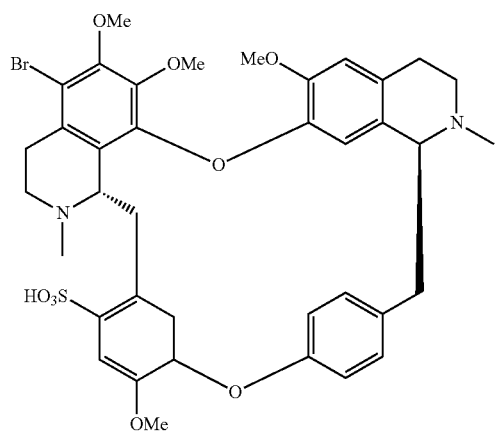
H-40
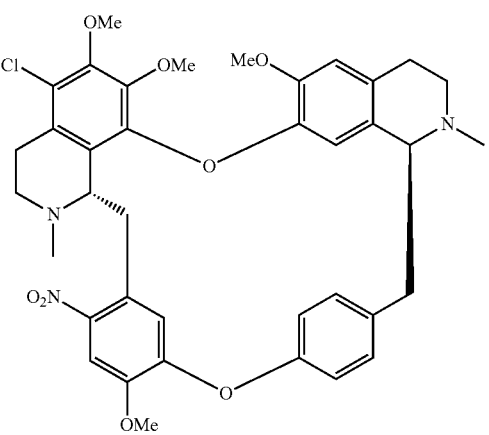
H-43

H-44
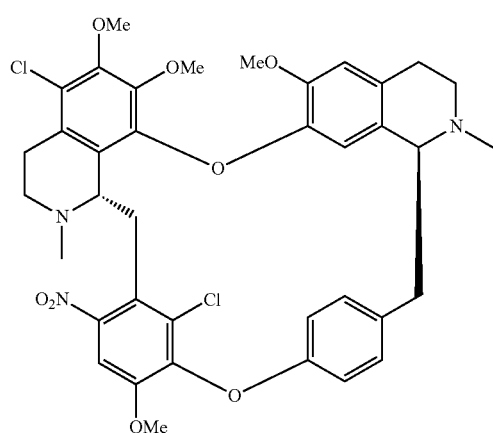
H-45
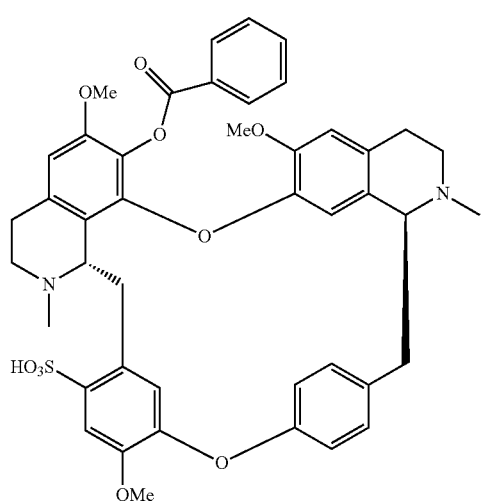
H-46
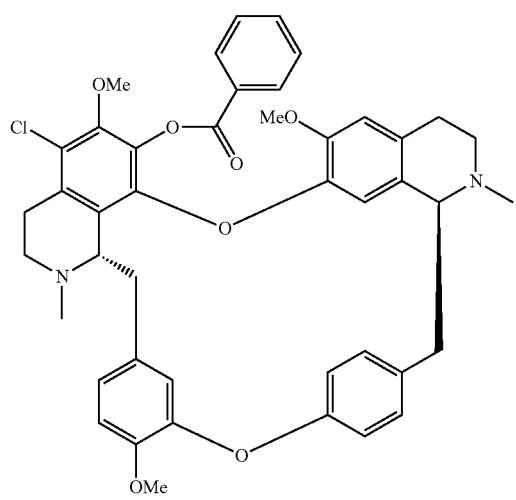
H-47
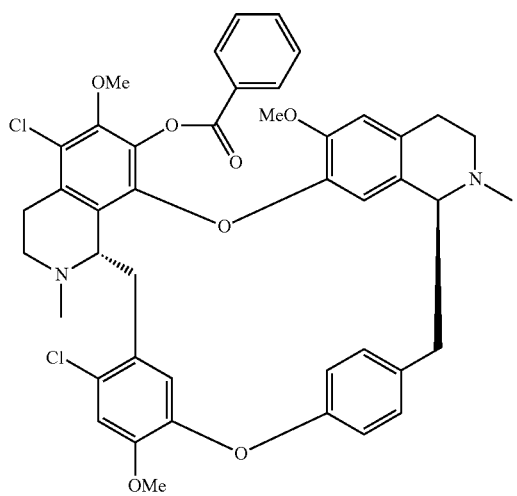
H-48
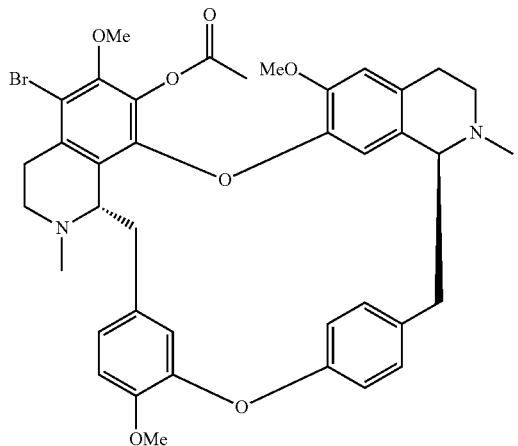
H-49
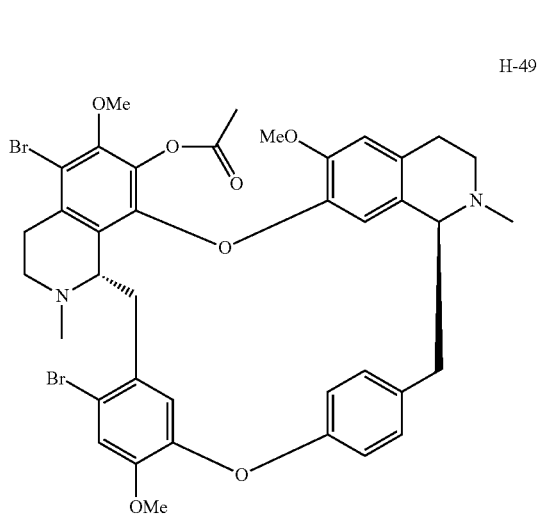

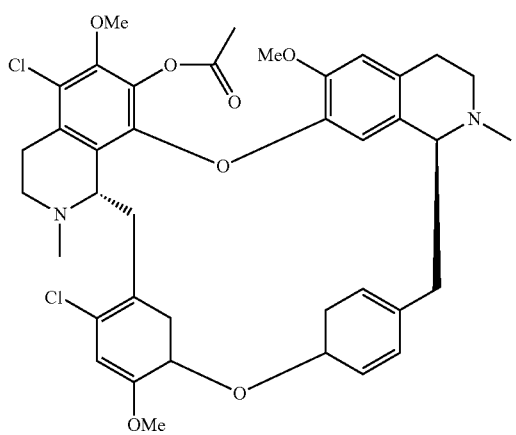

H-50

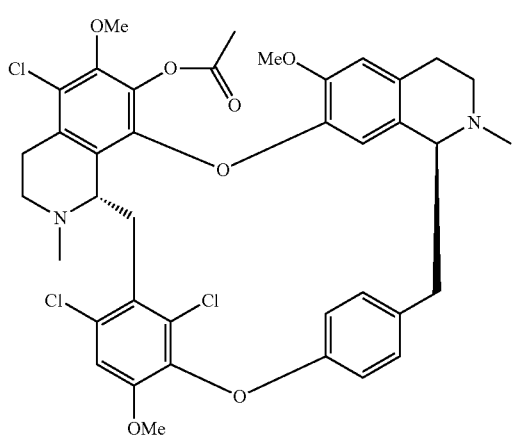

H-51

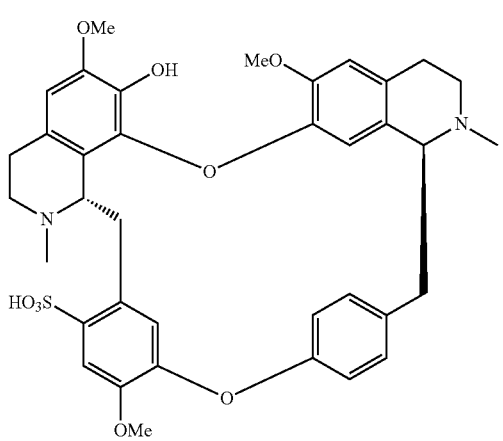

H-52

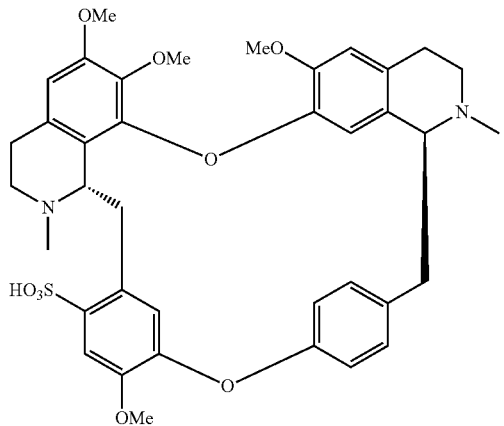

H-53

H-54

H-55

According to a further aspect, the present application relates to a pharmaceutical composition comprising a compound of general formula (I), general formula (Ia) or any one of H-01 to H-55, a single stereoisomer thereof, a mixture of stereoisomers thereof, and a prodrug, pharmaceutically acceptable salt and metabolite thereof, and a pharmaceutically acceptable carrier.

According to a further aspect, the present application relates to a method of preparing compound of general formula (I), a single stereoisomer thereof, a mixture of stereoisomers thereof, and a prodrug, pharmaceutically acceptable salt and metabolite thereof, (I)

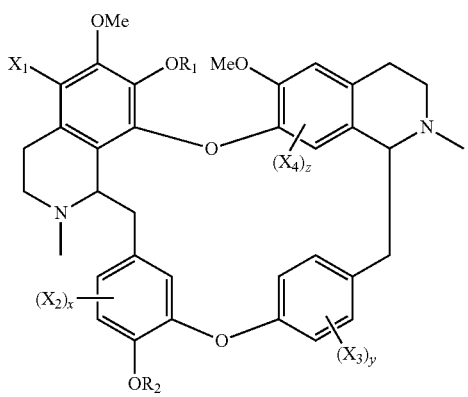

wherein, $X_1$, $X_2$, $X_3$ and $X_4$ are independently nitro; or $X_1$, $X_2$, $X_3$ and $X_4$ are independently hydrogen or nitro, provided that: $X_1$, $X_2$, $X_3$ and $X_4$ are not hydrogen simultaneously;

$R_1$ and $R_2$ are independently selected from hydrogen, nitroso, optionally substituted alkyl, optionally substituted alkenyl, optionally substituted alkynyl, optionally substituted cycloalkyl, optionally substituted sulfonyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

x is 1, 2 or 3;
y is 1, 2, 3 or 4; and
z is 1 or 2;

wherein the method comprises the nitrification reaction of berbamine, tetrandrine or tetrandrine B, the structures are below:

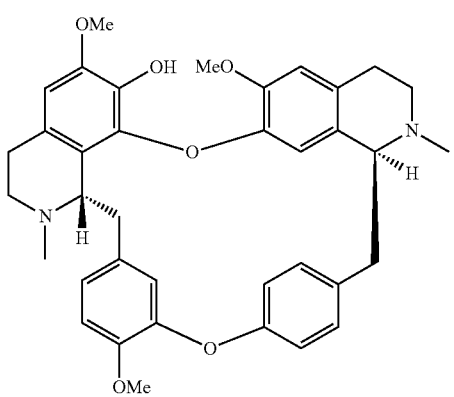

tetrandrine B

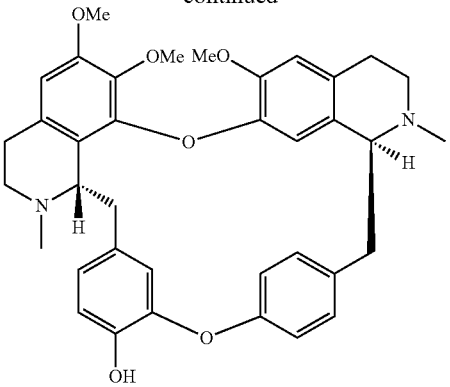

berbamine

According to a further aspect, the present application relates to a method of preparing compound of general formula (I), a single stereoisomer thereof, a mixture of stereoisomers thereof, and a prodrug, pharmaceutically acceptable salt and metabolite thereof,

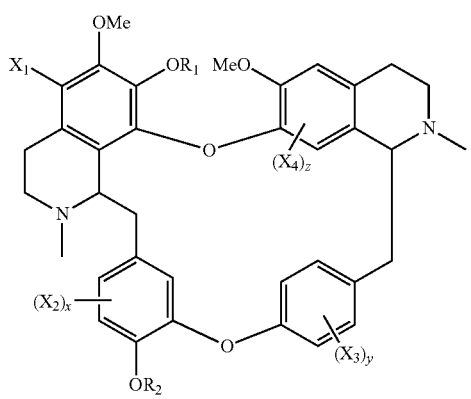

(I)

wherein, $X_1$, $X_2$, $X_3$ and $X_4$ are independently amino; or $X_1$, $X_2$, $X_3$ and $X_4$ are independently hydrogen or amino, provided that: $X_1$, $X_2$, $X_3$ and $X_4$ are not hydrogen simultaneously;

$R_1$ and $R_2$ are independently selected from hydrogen, nitroso, optionally substituted alkyl, optionally substituted alkenyl, optionally substituted alkynyl, optionally substituted cycloalkyl, optionally substituted aryl, optionally substituted sulfonyl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

x is 1, 2 or 3;
y is 1, 2, 3 or 4; and
z is 1 or 2;

wherein the method comprises the nitrification reaction of berbamine, tetrandrine or tetrandrine B, and then the reduction reaction of nitrification product.

According to a further aspect, the present application relates to a method of preparing compound of general formula (I), a single stereoisomer thereof, a mixture of stereoisomers thereof, and a prodrug, pharmaceutically acceptable salt and metabolite thereof,

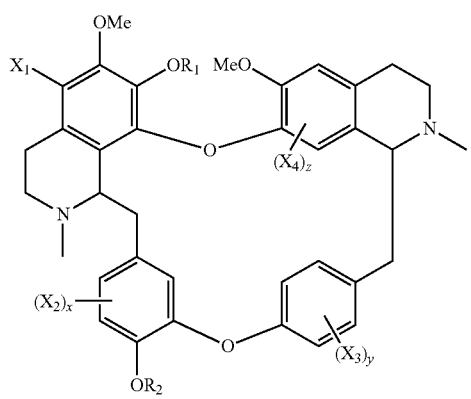

(I)

wherein,

X$_1$, X$_2$, X$_3$ and X$_4$ are independently carbonyl substituted amino; or X$_1$, X$_2$, X$_3$ and X$_4$ are independently hydrogen or —NR$_3$—C(=O)—R$_4$, provided that: X$_1$, X$_2$, X$_3$ and X$_4$ are not hydrogen simultaneously;

R$_1$ and R$_2$ are independently selected from hydrogen, nitroso, optionally substituted alkyl, optionally substituted alkenyl, optionally substituted alkynyl, optionally substituted cycloalkyl, optionally substituted sulfonyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

R$_3$ is selected from hydrogen, optionally substituted alkyl, optionally substituted alkenyl, optionally substituted alkynyl, optionally substituted cycloalkyl, optionally substituted aryl, optionally substituted heteroaryl;

R$_4$ is selected from optionally substituted alkyl, optionally substituted alkenyl, optionally substituted alkynyl, optionally substituted cycloalkyl, optionally substituted aryl, optionally substituted heteroaryl, optionally substituted heterocyclyl, optionally substituted alkoxy, optionally substituted arylcarbonyl, optionally substituted heteroarylcarbonyl, optionally substituted alkoxycarbonyl, optionally substituted alkylcarbonyl, optionally substituted alkenylcarbonyl or optionally substituted alkynylcarbonyl;

x is 1, 2 or 3;

y is 1, 2, 3 or 4; and z is 1 or 2;

wherein the method comprises the nitrification reaction of berbamine, tetrandrine or tetrandrine B, and then the reduction reaction of nitrification product and the acylation reaction of the reduction product.

According to a further aspect, the present application relates to a method of preparing compound of general formula (I), a single stereoisomer thereof, a mixture of stereoisomers thereof, and a prodrug, pharmaceutically acceptable salt and metabolite thereof,

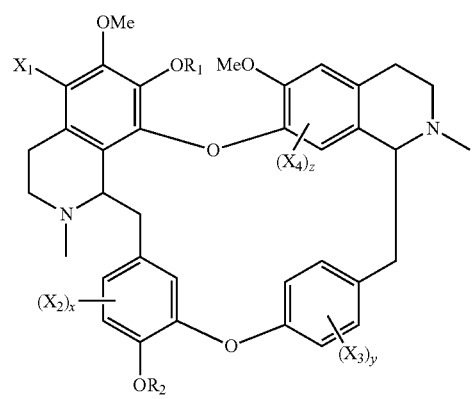

(I)

wherein,

X$_1$, X$_2$, X$_3$ and X$_4$ are independently —SO$_3$H; or X$_1$, X$_2$, X$_3$ and X$_4$ are independently hydrogen or —SO$_3$H, provided that: X$_1$, X$_2$, X$_3$ and X$_4$ are not hydrogen simultaneously;

R$_1$ and R$_2$ are independently selected from hydrogen, nitroso, optionally substituted alkyl, optionally substituted alkenyl, optionally substituted alkynyl, optionally substituted cycloalkyl, optionally substituted sulfonyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

x is 1, 2 or 3;

y is 1, 2, 3 or 4; and z is 1 or 2;

wherein the method comprises the sulfonation reaction of berbamine, tetrandrine or tetrandrine B.

According to a further aspect, the present application relates to a method of preparing compound of general formula (I), a single stereoisomer thereof, a mixture of stereoisomers thereof, and a prodrug, pharmaceutically acceptable salt and metabolite thereof,

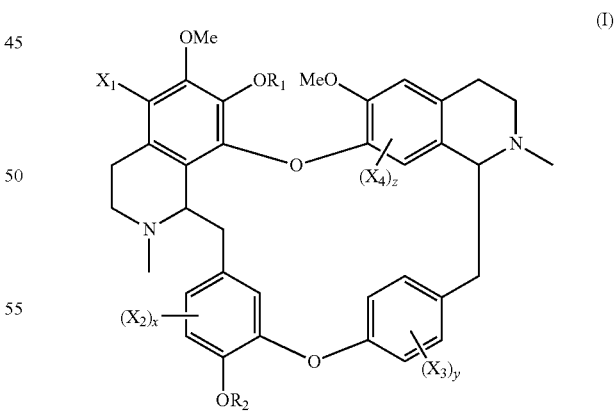

(I)

wherein,

X$_1$, X$_2$, X$_3$ and X$_4$ are independently hydrogen or —NH—S(=O)$_2$—R$_6$, provided that: X$_1$, X$_2$, X$_3$ and X$_4$ are not hydrogen simultaneously;

R$_1$ and R$_2$ are independently selected from hydrogen, nitroso, optionally substituted alkyl, optionally substituted alkenyl, optionally substituted alkynyl, optionally substituted cycloalkyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

$R_6$ is selected from optionally substituted alkyl, optionally substituted alkenyl, optionally substituted alkynyl, optionally substituted cycloalkyl, optionally substituted aryl, optionally substituted heteroaryl, optionally substituted heterocyclyl or optionally substituted amino;

x is 1, 2 or 3;

y is 1, 2, 3 or 4; and z is 1 or 2;

the method comprises the nitrification reaction of reacting berbamine, tetrandrine or tetrandrine B with concentrated nitric acid, performing reduction reaction using Fe powder, generating amino group, and then carrying out base catalyzed reaction of amino group with acid chloride, generating the compound of general formula (I).

According to a further aspect, the present application relates to a method of treating or preventing hepatopathy, the method comprising administering to a subject in need thererof an therapeutically effective amount of a compound or general formula (I), general formula (Ia), or any one of H-1 to H-55, a single stereoisomer thereof, a mixture of stereoisomers thereof, and a prodrug, pharmaceutically acceptable salt and metabolite thereof, or the described pharmaceutical composition.

DETAILED DESCRIPTION OF THE INVENTION

In the following description, certain specific details are included to provide a thorough understanding of various disclosed embodiments. One skilled in the relevant art, however, will recognize that the embodiments may be practiced without one or more these specific details, or with other methods, components, materials, etc.

Unless the context required otherwise, throughout the specification and claims which follows, the term "comprise" and variation thereof, such as "comprises" and "comprising" are to be construed in an open, inclusive sense, which is as "include, but not limited to".

Reference throughout this specification to "one embodiment", or "an embodiment", or "in another embodiment", or "in some embodiments" means that a particular referent feature, structure or characteristic described in connection with the embodiment is included in at least one embodiment. Therefore, the appearance of the phrases "in one embodiment" or "in the embodiment" or "in another embodiment" or "in some embodiments" in various places throughout this specification are not necessarily all referring to the same embodiment. Moreover, the particular features, structures or characteristics may be combined in any suitable manner in one or more embodiments.

It should be noted that, as used in this specification and the appended claims, the singular forms "a", "an" and "the" include plural referents unless the context clearly stated otherwise. Therefore, for example, a reaction comprising "a catalyst" comprises one catalyst, two or more catalyst. It should be also noted that the use of "or" means "and/or" unless stated otherwise.

Definition

Certain chemical groups named herein are preceded by a shorthand notion indicating the total number of carbon atoms that are to be found in the indicated chemical groups. For example, $C_7$-$C_{12}$ alkyl describes an alkyl as defined below, having a total of 7 to 12 carbon atoms, and $C_4$-$C_{12}$ cyclohydrocarbylalkyl describes a cyclohydrocarbylalkyl, as defined below, having a total 4 to 12 carbon atoms. The total number of carbon atoms in the shorthand notation does not include carbons that may exist in the substituents of the groups described.

Accordingly, as used in the specification and appended claims, unless specified to the contrary, the following terms have the meanings indicated:

"hydroxy" refers to the —OH group.

"cyan" refers to the —CN group.

"nitro" refers to the —$NO_2$ group.

"nitroso" refers to the —N=O group.

"amino" refers to the —$NH_2$ group.

"Alkyl" refers to a straight or branched hydrocarbon chain group consisting solely of carbon and hydrogen atoms, containing no unsaturation, having from one to twelve carbon atoms, preferably one to eight or one to six carbon atoms, and which is attached to the rest of the molecular by a single bond, e.g., methyl, ethyl, n-propyl, 1-methylethyl (isopropyl), n-butyl, n-pentyl, 1,1-dimethylethyl (t-butyl), and the like.

The alkyl group may be optionally substituted, i.e. substituted or unsubstituted. When substituted, the substituted group(s) is(are) individually and independently selected from: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"$C_1$-$C_4$ alkyl" refers to an alkyl group as defined above containing one to four carbon atoms. $C_1$-$C_4$ alkyl group may be optionally substituted as defined for alkyl group.

"$C_1$-$C_6$ alkyl" refers to an alkyl group as defined above containing one to six carbon atoms. $C_1$-$C_6$ alkyl group may be optionally substituted as defined for alkyl group.

"$C_1$-$C_{12}$ alkyl" refers to an alkyl group as defined above containing one to twelve carbon atoms. $C_1$-$C_{12}$ alkyl group may be optionally substituted as defined for alkyl group.

In some embodiments, alkyl is $C_1$-$C_4$ alkyl.

In some embodiments, alkyl is $C_1$-$C_6$ alkyl.

In some embodiments, alkyl is $C_1$-$C_{12}$ alkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. The alkenyl groups of the present application may be substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"$C_2$-$C_6$ alkenyl" refers to an alkenyl group as defined above containing two to six carbon atoms. $C_2$-$C_6$ alkenyl group may be optionally substituted as defined for alkenyl group.

"$C_2$-$C_8$ alkenyl" refers to an alkenyl group as defined above containing two to eight carbon atoms. $C_2$-$C_8$ alkenyl group may be optionally substituted as defined for alkenyl group.

"$C_2$-$C_{12}$ alkenyl" refers to an alkenyl group as defined above containing two to twelve carbon atoms. $C_2$-$C_{12}$ alkenyl group may be optionally substituted as defined for alkenyl group.

In some embodiments, alkenyl is $C_2$-$C_6$ alkenyl.
In some embodiments, alkenyl is $C_2$-$C_8$ alkenyl.
In some embodiments, alkenyl is $C_2$-$C_{12}$ alkenyl.

"Alkynyl" refers to a straight or branched hydrocarbon chain radical group consisting solely of carbon and hydrogen atoms, containing at least one triple bond, having from two to twelve carbon atoms, preferably two to eight carbon atoms or two to six carbon atoms and which is attached to the rest of the molecule by a single bond, e.g., ethynyl, propynyl, butynyl, pentynyl, hexynyl, and the like. The alkynyl groups of the present application may be substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"$C_2$-$C_6$ alkynyl" refers to an alkynyl group as defined above containing two to six carbon atoms. $C_2$-$C_6$ alkynyl group may be optionally substituted as defined for alkynyl group.

"$C_2$-$C_8$ alkynyl" refers to an alkynyl group as defined above containing two to eight carbon atoms. $C_2$-$C_8$ alkynyl group may be optionally substituted as defined for alkynyl group.

"$C_2$-$C_{12}$ alkynyl" refers to an alkynyl group as defined above containing two to twelve carbon atoms. $C_2$-$C_{12}$ alkynyl group may be optionally substituted as defined for alkynyl group.

In some embodiments, alkynyl is $C_2$-$C_6$ alkynyl.
In some embodiments, alkynyl is $C_2$-$C_8$ alkynyl.
In some embodiments, alkynyl is $C_2$-$C_{12}$ alkynyl.

The term "halogen" in the present application refers to bromo, chloro, fluoro or iodo.

"Halo alkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Alkoxy" refers to —OR group, wherein R is alkyl radical, as defined above.

"Cycloalkyl" refers to a stable non-aromatic monocyclic or polycyclic hydrocarbon radical consisting solely of carbon and hydrogen atoms, which may include fused or bridged ring systems, having from three to eighteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptly, and cyclooctyl. Polycyclic radicals include, for example, adamantyl, norbornyl, decalinyl, 7,7-dimethyl-bicyclo 2.2.1heptanyl, and the like. The cycloalkyl groups of the present application may be substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"$C_3$-$C_{18}$ cycloalkyl" refers to an cycloalkyl group as defined above containing three to eighteen carbon atoms. $C_3$-$C_{18}$ cycloalkyl group may be optionally substituted as defined for cycloalkyl group.

"$C_3$-$C_{15}$ cycloalkyl" refers to an cycloalkyl group as defined above containing three to fifteen carbon atoms. $C_3$-$C_{15}$ cycloalkyl group may be optionally substituted as defined for cycloalkyl group.

"$C_3$-$C_{10}$ cycloalkyl" refers to an cycloalkyl group as defined above containing three to ten carbon atoms. $C_3$-$C_{10}$ cycloalkyl group may be optionally substituted as defined for cycloalkyl group.

In some embodiments, cycloalkyl is $C_3$-$C_{18}$ cycloalkyl.
In some embodiments, cycloalkyl is $C_3$-$C_{15}$ cycloalkyl.
In some embodiments, cycloalkyl is $C_3$-$C_{10}$ cycloalkyl.

"Aryl" refers to aromatic monocyclic or multicyclic hydrocarbon ring system consisting only of hydrogen and carbon and containing from 6 to 18 carbon atoms, preferably six to twelve carbon atoms or six to ten carbon atoms where the ring system may be partially saturated. Aryl groups include, but are not limited to groups such as phenyl, naphthyl or fluorenyl. The aryl groups in the present application may be substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"$C_6$-$C_{18}$ aryl" refers to an aryl group as defined above containing six to eighteen carbon atoms. $C_6$-$C_{18}$ aryl group may be optionally substituted as defined for aryl group.

"$C_6$-$C_{12}$ aryl" refers to an aryl group as defined above containing six to twelve carbon atoms. $C_6$-$C_{12}$ aryl group may be optionally substituted as defined for aryl group.

"$C_6$-$C_{10}$ aryl" refers to an aryl group as defined above containing six to ten carbon atoms. $C_6$-$C_{10}$ aryl group may be optionally substituted as defined for aryl group.

In some embodiments, aryl is $C_6$-$C_{18}$ aryl.

In some embodiments, aryl is $C_6$-$C_{12}$ aryl.

In some embodiments, aryl is $C_6$-$C_{10}$ aryl.

"Heteroaryl" refers to a 5- to 18-membered aromatic ring radical which consists of carbon atom and from one to five heteroatoms selected from the group consisting of nitrogen, oxygen and sulfur. The heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzooxazolyl, benzodioxolyl, benzodioxinyl, benzopyranyl, benzopyranonyl, benzofuryl, benzofuranonyl, benzothienyl (benzothiophenyl), benzotriazolyl, benzo[4,6]imidazo[1,2]apyridinyl, carbazolyl, cinnolinyl, dibenzofuranyl, furyl, thienyl, furanonyl, isothiazolyl, imidazolyl, indazolyl, indolyl, indazolyl, isoindolyl, indolinyl, isoindolinyl, indoly, isoxazolyl, naphthyridinyl, oxadiazolyl, 2-oxoazepinyl, oxazolyl, epoxy ethyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl.

Heteroaryl may be optionally substituted, i.e. substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"5- to 18-membered heteroaryl" refers to a 5- to 18-membered aromatic ring radical which consists of carbon atom and from one to five heteroatoms selected from the group consisting of nitrogen, oxygen and sulfur. 5- to 18-membered heteroaryl may be optionally substituted as defined for heteroaryl group.

"5- to 12-membered heteroaryl" refers to a 5- to 12-membered aromatic ring radical which consists of carbon atom and from one to five heteroatoms selected from the group consisting of nitrogen, oxygen and sulfur. 5- to 12-membered heteroaryl may be optionally substituted as defined for heteroaryl group.

"5- to 10-membered heteroaryl" refers to a 5- to 10-membered aromatic ring radical which consists of carbon atom and from one to five heteroatoms selected from the group consisting of nitrogen, oxygen and sulfur. 5- to 10-membered heteroaryl may be optionally substituted as defined for heteroaryl group.

In some embodiments, heteroaryl is 5- to 18-membered heteroaryl.

In some embodiments, heteroaryl is 5- to 12-membered heteroaryl.

In some embodiments, heteroaryl is 5- to 10-membered heteroaryl.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; and the heterocyclyl radical may be partially or fully saturated. Examples of such heterocyclyl radicals include, but are not limited to, dioxolanyl, thienyl[1,3]dithianyl, ecahydroisoquinolyl, imidazolinyl, imidazolidinyl, isothiazolidinyl, isoxazolidinyl, morpholinyl, octahydroindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, trithianyl, triazinyl, tetrahydropyranyl, thiomorpholinyl, thiamorpholinyl, 1-oxo-thiomorpholinyl and 1,1-dioxo-thiomorpholinyl.

"Carbonyl" refers to the groups whose carbon atoms and oxygen atoms are bonded with double bond. (i.e. C(=O) radical).

"Alkylcarbonyl" refers to —C(=O)R, wherein R is alkyl radical, as defined above. Alkylcarbonyl groups include, but are not limited to groups such as —C(=O)$CH_3$, —C(=O)$CH_2CH_3$, —C(=O)$CF_3$, —C(=O)$CCl_3$, —C(=O)$CClH_2$ and —C(=O)$CH_2CN$. The alkylcarbonyl of the present application may be substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"Alkenylcarbonyl" refers to —C(=O)R, wherein R is alkenyl radical, as defined above. Alkenylcarbonyl groups include, but are not limited to groups such as —C(=O)CH=$CH_2$, —C(=O)CH=$CHCH_3$, —C(=O)CH=$CF_2$, —C(=O)CH=$CCl_2$ and —C(=O)CH=$CHCH_2CN$. The alkenylcarbonyl groups of the present application may be substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"Alkynylcarbonyl" refers to —C(=O)R, wherein R is alkynyl radical, as defined above. Alkynylcarbonyl groups include, but are not limited to groups such as —C(=O)C≡CH, —C(=O)$CH_2$C≡CH, —C(=O)C≡CF and —C(=O)C≡$CCH_2CN$. The alkynylcarbonyl of the present application may be substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"Arylcarbonyl" refers to —C(=O)R, wherein R is aryl radical, as defined above. Arylcarbonyl groups include, but are not limited to groups such as —C(=O)Ph, —C(=O)(PhCF$_3$), —C(=O)(PhOMe) and —C(=O)(PhNO$_2$). The arylcarbonyl of the present application may be substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"Heteroarylcarbonyl" refers to —C(=O)R, wherein R is heteroaryl radical, as defined above. Heteroarylcarbonyl groups include, but are not limited to groups such as, 2-thenoyl, 2-furoyl. The heteroarylcarbonyl groups of the present application may be substituted or unsubstituted. When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"Sulfonyl" refers to —S(=O)$_2$R, wherein R may be alkyl, cycloalkyl, heterocyclyl, aryl, heteroaryl, hydroxy, amino and the like. Sulfonyl groups include, but are not limited to groups such as —S(=O)$_2$CH$_3$(mesyl), —S(=O)$_2$CF$_3$, —S(=O)$_2$CH$_2$CH$_3$ and 4-methyl phenyl sulfonyl (tosyl). When substituted, the substituted group(s) is(are) individually and independently selected from one or more: alkyl, alkenyl, alkynyl, cycloalkyl, aryl, heteroaryl, heteroalicyclic, hydroxy, alkoxy, aryloxy, mercapto, hydrocarbylthio, arylthio, cyan, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, amino including mono- and bi-substituted amino group, and the protected derivatives thereof. Whenever a substituted is described as being "optionally substituted", that substituent may be substituted with one of the above substituents.

"Prodrug" is meant to indicate to a compound which can be converted under physiological conditions or by solvolysis to a biologically active compound of the present application. Therefore, the term "prodrug" refers to a metabolic precursor of a compound of the present application that is pharmaceutically acceptable. A prodrug may be inactive when administered to a subject in need thereof, but is converted in vivo to an active compound of the present application. Prodrugs are typically rapidly transformed in vivo to yield the parent compound of the present application, for example, by hydrolysis in blood. The prodrug compound often provides advantages of solubility, tissue compatibility or controlled-release in organism of mammals (see Bundgard, H., Design of Prodrugs (1985), pp. 7-9, 21-24 (Elsevier, Amsterdam)).

A discussion of prodrugs is provided in Higuchi, T., et al, "Pro-drugs as Novel Delivery Systems," A.C.S. Symposium Series, (1975), Vol. 14 and Bioreversible Carriers in Drug Design, ed. Edward B. Roche, American Pharmaceutical Association and Pergamon Press, both of which are incorporated in full by reference herein.

The term "prodrug" is also meant to include any covalently bonded carriers which release the active compound of the present application in vivo when such a prodrug is administered to a mammal subject. Prodrugs of a compound of the present application can be prepared by modifying a functional group present in the compound of the present application in such a way that the modifications are cleaved either in routine manipulation or in vivo, to the parent compound of the present application. Prodrugs include compounds of the present application, wherein hydroxy, amino or mercapto group is bonded to any group that, when the prodrug of a compound of the present application is administered to a mammal subject, cleaves to form free hydroxy, free amino or free mercapto group, respectively. Examples of a prodrug include, but are not limited to, acetate, formate and benzoate derivatives of alcohol or amine functional groups in the compound of the present application and the like.

"Optional" or "optionally" means that the subsequently described event of circumstances may or may not occur, and that the description includes instances where said events or circumstances occur and instance in which it does not. For example, "optionally substituted aryl" means that the aryl group may or may not be substituted and the description includes both substituted aryl groups and aryl groups having no substitution.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and have no side effects on preparing a pharmaceutical composition.

"Pharmaceutically acceptable salts" include both "pharmaceutically acceptable acid addition salts" and "pharmaceutically acceptable base addition salts".

"Pharmaceutically acceptable acid addition salt" refers to those salts which retain the biological effectiveness and properties of the free bases, which are not biologically or otherwise undesirable, and which are formed with inorganic acids such as, but not limited to hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxoglutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

"Pharmaceutically acceptable base addition salt" refers to those salts which retain the biological effectiveness and properties of the free acids, which are not biologically or otherwise undesirable. These salts are prepared from addition of an inorganic or an organic base to the free acid. Salts derived from inorganic bases include, but are not limited to, sodium, potassium, lithium, ammonium, calcium, magnesium, iron, zinc, copper, manganese, aluminum slats, and the like. Preferred inorganic salts are the ammonium, sodium, potassium, calcium, and magnesium salts. Salts derived from organic bases include, but are not limited to, slats of primary, secondary and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminethanol, dicyclohexylamine, lysine, arginine, histidine, caffeine, procaine, hydrabamine, choline, betaine, benethamine, benzathine, ethylenediamine, glucosamine, methylglucosamine, theobromine, triethanolamine, trometamol, purine, piperazine, piperidine, N-ethyl piperidine, polyamine resin and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A polymorph is a composition having the same chemical formula, but a different structure.

A "pharmaceutical composition" refers to a formulation of a compound of the present application and a medium generally accepted in the art for the delivery of the biologically active compound to a subject. Such a medium includes all pharmaceutically acceptable carriers, diluents or excipients.

A pharmaceutical composition comprising a compound of general formula (I) or a pharmaceutical composition of general formula (Ia) can be prepared according to formulation and be used as following dosage form: tablets, capsules or elixir for oral administration; suppository for rectal administration; sterile solution, suspension for injection administration; patch for transdermal administration and subcutaneous sediments, and the like. The injection may be prepared as the following forms: solution or suspension, a solid dosage form suitably being prepared as solution or suspension prior to injection, or emulsion. Suitable excipient may be for example, water, saline, glucose, mannitol, lactose, lecithin, albumin, sodium glutamate, cysteine hydrochloride, and the like. Additionally, if necessary, the pharmaceutical composition for injection may contain few amounts of nontoxic auxiliaries such as wetting agent, pH buffer and the like. If necessary, absorption reinforcing agent (such as liposome) may be used.

Preparation for parenteral administration may contain an aqueous solution of the active compound in the form of aqueous solution. Additionally, the suspension of the active compound can be prepared as suitable oily injection suspension. Suitable lipotropic solvent or carrier includes fatty oils such as sesame oil, or other organic oil such as soybean oil, pomelo oil, apricot kernel oil, or aliphatic ester such as ethyl oleate or triglyceride, or liposome. Aqueous injection suspension may include a substance for enhancing the viscosity of the suspension, such as sodium carboxymethylcellulose, sorbitol or glucan. Optionally, the suspension may include suitable stabilizer or reagent for improving the solubility of the compound, so as to prepare a solution having high concentration.

A pharmaceutical preparation for oral administration can be obtained as following process: contacting the active compound with solid excipient, and the resultant mixture is optionally grounded, and the granular mixture is processed, if necessary, suitable adjuvant is added so as to obtain tablets or sugarcoat agent core. Suitable excipient is specifically filler such as sugar, including lactose, saccharose, mannitol or sorbitol; cellulose preparation such as corn starch, wheat starch, rice starch, potato starch, gelatin, tragacanth, methylcellulose, hydroxypropyl methyl cellulose, sodium carboxymethyl cellulose, and/or polyvinylpyrrolidone (PVP). If necessary, the disintegrant may be added, such as crosslinked polyvinylpyrrolidone, agar or alginic acid or alginate such as sodium alginate. The sugarcoat agent core can be suitably coated. For this purpose, concentrated sugar solution can be used, and this solution can optionally comprise acacia, talc, polyvinylpyrrolidone, polycarboxyvinyl gels, polyethylene glycol and/or titanium dioxide, lacquer solution and suitable organic solvent or mixture of solvents. For recognizing or expressing the features of different combinations of the dose of the active compound, a dye or pigment can be added into tablets or sugarcoat agent coating. These preparations can be produced according to well-known methods in the art.

The present application is also directed to various pharmaceutical compositions for delivery such as intraocular delivery, nasal delivery and in-ear delivery, as well-known in the art. Pharmaceutical formulation includes aqueous ophthalmic solution of the active compound, which can be present in the form of aqueous solution such as eye drops, or gellengums or hydrogels; ophthalmic ointment; ophthalmic suspension, such as particle, small aggregated particle having medicine suspended in liquid carrier medium, liposoluble preparation, and microbeads; and ophthalmic implant. For stability and comfortability, these suitable pharmaceutical preparations are more often and preferably prepared as sterile, isotomic and buffered preparation. Pharmaceutical composition also includes drops and sprays, and usually imitate nose secretion in many ways so as to ensure the maintenance of the normal cilium effect. As known by a person having ordinary skill in the art, suitable preparation is most often and preferably isotonic and slightly buffered at pH of 5.5 to 6.5, and most often and preferably contains an antibiotic preservative and suitable a pharmaceutical stabilizer. Pharmaceutical preparation for transportation in ear includes suspension and ointment which is locally applied in the ear. Common solvents for these ear preparations include glycerol and water.

A compound of general formula (I), a compound of general formula (Ia) or a pharmaceutical composition comprising the compound of general formula (I) or the compound of general formula (Ia) can be administered through oral routine or non-oral routine. While orally administered, it can be administered as capsule, tablet, granule, spray, syrup or other dosage form. While non-orally administered, it can be administered as aqueous suspension, oily preparation, etc, or drop, suppository, unction, ointment, etc. While administered by injection, it can be administered by means of subcutaneous routine, intraperitoneal routine, intravenous routine, intramuscular routine.

"Therapeutically effective amount" refers to that amount of a compound of the present application which, when administered to a mammal, preferably a human, is sufficient to effect treatment, as defined below, of a disease or condition mediated in the subject such as a mammal, preferably a human. The amount of a compound of the present application which constitutes a "therapeutically effective amount" will vary depending on the selected compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a subject such as a mammal, preferably a human, having the disease or disorder of interest, and includes:

(i) preventing the disease or condition from occurring in a subject such as a mammal, in particular, when the subject such as a mammal is predisposed to the condition but has not yet been diagnosed as having it;

(ii) inhibiting the disease or condition, i.e. arresting its development; or (iii) relieving the disease or condition, i.e. causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the present application, or their pharmaceutically acceptable salts may contain one or more asymmetric centers and may thus give rise to enantiomers, diastereoisomers, and other stereoismeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers can be prepared using chiral synthons or chiral reagents, or resolved using conventional techniques such as HPLC using a chiral column. When the compounds described herein contain olefinic double bonds or other centers of geometric asymmetry, and unless specified otherwise, it is intended that the compounds include E and Z geometric isomers. Likewise, all tautomeric forms are also intended to be included.

"A stereoisomer" refers to a compound consisting of identical atoms bonded by identical chemical bonds, but having different three-dimensional structures which are uninterchangeably. The present application covers various stereoisomers and mixtures thereof.

As used herein, the term "contact" refers to that two or more substances get close each other to interact.

EMBODIMENTS

On the one aspect, the present application relates to a compound of general formula (I), a single stereoisomer thereof, a mixture of stereoisomers thereof, and a prodrug, pharmaceutically acceptable salt and metabolite thereof:

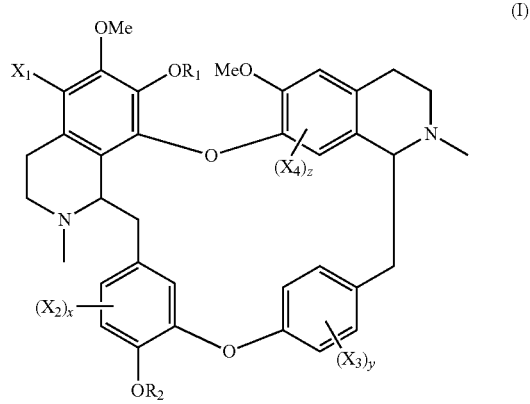

(I)

wherein, $X_1$, $X_2$, $X_3$ and $X_4$ are independently selected from hydrogen, halogen, nitro, nitroso, —$SO_3H$, optionally substituted amino or optionally substituted sulfonyl;

$R_1$ and $R_2$ are independently selected from hydrogen, nitroso, optionally substituted alkyl, optionally substituted alkenyl, optionally substituted alkynyl, optionally substituted cycloalkyl, optionally substituted sulfonyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

x is 1, 2 or 3;

y is 1, 2, 3 or 4; and z is 1 or 2;

provided that:

$X_1$, $X_2$, $X_3$ and $X_4$ are not hydrogen simultaneously; and when one of $X_1$, $X_2$, $X_3$ and $X_4$ is halogen, the rest of $X_1$, $X_2$, $X_3$ and $X_4$ are independently selected from hydrogen, nitro, nitroso, —$SO_3H$, optionally substituted amino or optionally substituted sulfonyl, but they are not hydrogen simultaneously.

In some embodiments, $X_1$, $X_2$, $X_3$ and $X_4$ are independently selected from hydrogen, halogen, nitro, nitroso, amino, —$SO_3H$, —$NR_3$—C(=O)—$R_4$, —$NR_5$—S(=O)$_2$—$R_6$ or —S(=O)$_2$—$R_7$;

$R_1$ and $R_2$ are independently selected from hydrogen, nitroso, optionally substituted alkyl, optionally substituted alkenyl, optionally substituted alkynyl, optionally substituted cycloalkyl, optionally substituted sulfonyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

$R_3$ and $R_5$ are independently selected from hydrogen, optionally substituted alkyl, optionally substituted alkenyl, optionally substituted alkynyl, optionally substituted cycloalkyl, optionally substituted aryl, optionally substituted heteroaryl;

$R_4$ is selected from optionally substituted alkyl, optionally substituted alkenyl, optionally substituted alkynyl, optionally substituted cycloalkyl, optionally substituted aryl, optionally substituted heteroaryl, optionally substituted heterocyclyl, optionally substituted alkoxy, optionally substituted arylcarbonyl, optionally substituted heteroarylcarbonyl, optionally substituted alkoxycarbonyl, optionally substituted alkylcarbonyl, optionally substituted alkenylcarbonyl or optionally substituted alkynylcarbonyl;

$R_6$ and $R_7$ are independently selected from optionally substituted alkyl, optionally substituted alkenyl, optionally substituted alkynyl, optionally substituted cycloalkyl, optionally substituted aryl, optionally substituted heteroaryl, optionally substituted heterocyclyl or optionally substituted amino;

x is 1, 2 or 3;
y is 1, 2, 3 or 4;
z is 1 or 2; and
provided that:
$X_1$, $X_2$, $X_3$ and $X_4$ are not hydrogen simultaneously; and when one of $X_1$, $X_2$, $X_3$ and $X_4$ is halogen, the rest of $X_1$, $X_2$, $X_3$ and $X_4$ are independently selected from hydrogen, nitro, nitroso, amino, —$SO_3H$, —$NR_3$—C(=O)—$R_4$, —$NR_5$—S(=O)$_2$—$R_6$ or —S(=O)$_2$—$R_7$, but they are not hydrogen simultaneously.

In some embodiments, x is 1, 2 or 3.
In some embodiments, y is 1, 2 or 3 or 4.
In some embodiments, z is 1 or 2.
In some embodiments, $X_1$, $X_2$, $X_3$ and $X_4$ are independently selected from hydrogen, halogen, nitro, nitroso, —$SO_3H$, amino substituted with optionally substituted alkylcarbonyl, amino substituted with optionally substituted alkenylcarbonyl, amino substituted with optionally substituted alkynylcarbonyl, amino substituted with optionally substituted alkoxycarbonyl, amino substituted with optionally substituted cycloalkylcarbonyl, amino substituted with optionally substituted arylcarbonyl, amino substituted with optionally substituted heterocyclylcarbonyl, amino substituted with optionally substituted aminocarbonyl, amino substituted with optionally substituted heteroarylcarbonyl, amino substituted with optionally substituted alkoxycarbonyl carbonyl, amino substituted with optionally substituted alkylsulfonyl, amino substituted with optionally substituted alkenylsulfonyl, amino substituted with optionally substituted alkynylsulfonyl, amino substituted with optionally substituted alkoxysulfonyl, amino substituted with optionally substituted arylsulfonyl, amino substituted with optionally substituted heterocyclylsulfonyl, amino substituted with optionally substituted heteroarylsulfonyl, amino substituted with optionally substituted aminosulfonyl, sulfonyl substituted with optionally substituted arylamino or sulfonyl substituted with optionally substituted alkyl.

In some embodiments, $X_1$, $X_2$, $X_3$ and $X_4$ are independently selected from hydrogen, halogen, nitro, nitroso, —$SO_3H$, alkylcarbonyl substituted amino, amino substituted with hydroxy substituted alkylcarbonyl, amino substituted with ester substituted alkylcarbonyl, alkenylcarbonyl substituted amino, alkoxycarbonyl substituted amino, amino substituted with aryl substituted alkoxycarbonyl, amino substituted with halogen substituted arylcarbonyl, amino substituted with alkoxy substituted arylcarbonyl, amino substituted with haloalkyl substituted arylcarbonyl, alkoxycarbonyl carbonyl substituted amino, heterocyclyl carbonyl substituted amino, alkylsulfonyl substituted amino, arylalkylsulfonyl substituted amino, arylsulfonyl substituted amino, amino substituted with nitro substituted arylsulfonyl, amino substituted with alkyl substituted arylsulfonyl, amino substituted with halogen substituted arylsulfonyl, amino substituted with alkyl substituted amino sulfonyl, aryl amino substituted sulfonyl or alkoxy substituted alkyl substituted sulfonyl.

In some embodiments, $R_1$ is selected from hydrogen, nitroso, alkyl, aryl substituted alkyl, aryl, alkylcarbonyl or arylcarbonyl.

In some embodiments, x is 1, and $X_2$ is selected from halogen, nitro, nitroso, amino, —$SO_3H$, alkylcarbonyl substituted amino, amino substituted with hydroxy substituted alkylcarbonyl, amino substituted with ester substituted alkylcarbonyl, alkenylcarbonyl substituted amino, amino substituted with aryl substituted alkenylcarbonyl, alkoxycarbonyl substituted amino, amino substituted with aryl substituted alkoxycarbonyl, arylcarbonyl substituted amino, amino substituted with halogen substituted arylcarbonyl, amino substituted with alkoxy substituted arylcarbonyl, amino substituted with haloalkyl substituted arylcarbonyl, alkoxycarbonyl carbonyl substituted amino, heterocyclyl carbonyl substituted amino, heteroarylcarbonyl substituted amino, alkylsulfonyl substituted amino, arylalkylsulfonyl substituted amino, arylsulfonyl substituted amino, amino substituted with nitro substituted arylsulfonyl, amino substituted with alkyl substituted arylsulfonyl, amino substituted with halogen substituted arylsulfonyl, amino substituted with alkyl substituted amino sulfonyl, aryl amino substituted sulfonyl or alkoxy substituted alkyl substituted sulfonyl.

In some embodiments, y is 4, and $X_3$ is hydrogen.
In some embodiments, z is 2, and $X_4$ is hydrogen.
In some embodiments, $X_1$ is hydrogen.

In some embodiments, x is 2, and one $X_2$ is hydrogen, the other $X_2$ is selected from amino, nitro, nitroso, —$SO_3H$, Br, Cl, methylcarbonylamino, isopropylcarbonylamino, isobutylcarbonylamino, ethenylcarbonylamino, styrylcarbonylamino, 2-methylpropenylcarbonylamino, 2-methylpropoxycarbonylamino, hydroxymethylcarbonylamino, methylcarbonyloxymethylcarbonylamino, methoxycarbonylcarbonylamino, furylcarbonylamino, thienylcarbonylamino, morpholinylcarbonylamino, phenylcarbonylamino, 2-chlorophenylcarbonylamino, 4-chlorophenylcarbonylamino, 4-methoxyphenylcarbonylamino, trifluoromethylphenylcarbonylamino, phenylmethoxycarbonylamino, methanesulfonylamino, benzsulfamide, 2-nitrobenzsulfamide, 4-nitrobenzsulfamide, 4-methylbenzsulfamide, 4-chlorobenzsulfamide, 2,4-dichlorobenzsulfamide, phenylmethanesulfonylamino, dimethylaminosulfonylamino, phenylaminosulfonyl or methoxymethylsulfonyl.

In some embodiments, $R_2$ is alkyl.
In some embodiments, $R_2$ is $C_1$-$C_6$ alkyl.
In some embodiments, $R_2$ is methyl.

In some embodiments, R₁ is alkyl, and R₂ is alkyl.

In some embodiments, $R_1$ is $C_1$-$C_6$ alkyl, and $R_2$ is $C_1$-$C_6$ alkyl.

In some embodiments, $R_1$ methyl, and $R_2$ is methyl.

In some embodiments, $R_1$ is alkyl, and $R_2$ is hydrogen.

In some embodiments, $R_1$ is $C_1$-$C_6$ alkyl, and $R_2$ is hydrogen.

In some embodiments, $R_1$ is methyl, and $R_2$ is hydrogen.

In some embodiments, $X_1$ is halogen, $X_2$, $X_3$ and $X_4$ are independently selected from nitro, nitroso, amino, —SO₃H, —NR₃—C(=O)—R₄, —NR₅—S(=O)₂—R₆ or —S(=O)₂—R₇.

In some embodiments, $X_1$ is halogen, $X_2$ is selected from nitro and/or —SO₃H, $X_3$ and $X_4$ is hydrogen, x is 1.

In some embodiments, x is 1, $X_2$ is at the position of C-14.

In some embodiments, x is 2, $X_2$ is at the position of C-10 and C-14 respectively.

In some embodiments, $X_3$ and $X_4$ is hydrogen.

In some embodiments, $R_1$ is selected from hydrogen, nitroso, optionally substituted $C_1$-$C_6$ alkyl, optionally substituted phenylcarbonyl or optionally substituted $C_1$-$C_6$ alkylcarbonyl.

In some embodiments, $R_1$ is selected from hydrogen, methyl, benzyl, benzoyl, nitroso or acetyl.

In some embodiments, $R_1$ is selected from hydrogen, methyl, benzyl, benzoyl, nitroso or acetyl; and/or $R_2$ is methyl; and/or $X_1$ is hydrogen, nitro or halogen (halogen preferably is Br or Cl); and/or x is 1 or 2, and at least one $X_2$ is hydrogen, amino, nitro, nitroso, —SO₃H, Br, Cl, methylcarbonylamino, isobutylcarbonylamino, ethenylcarbonylamino, styrylcarbonylamino, 2-methylpropenylcarbonylamino, 2-methylpropoxycarbonylamino, hydroxymethylcarbonylamino, methylcarbonyloxymethylcarbonylamino, methoxycarbonylcarbonylamino, furylcarbonylamino, thienylcarbonylamino, morpholinylcarbonylamino, phenylcarbonylamino, 2-chlorophenylcarbonylamino, 4-chlorophenylcarbonylamino, 4-methoxyphenylcarbonylamino, trifluoromethylphenylcarbonylamino, phenylmethoxycarbonylamino, methanesulfonylamino, benzsulfamide, 2-nitrobenzsulfamide, 4-nitrobenzsulfamide, 4-methylbenzsulfamide, 4-chlorobenzsulfamide, 2,4-dichlorobenzsulfamide, phenylmethanesulfonylamino, dimethylaminosulfonylamino, phenylaminosulfonyl or methoxymethylsulfonyl; and/or y is 3, and $X_3$ is hydrogen; and/or z is 2, and $X_4$ is hydrogen, provided that:

$X_1$, $X_2$, $X_3$ and $X_4$ are not hydrogen simultaneously, and when one of $X_1$, $X_2$, $X_3$ and $X_4$ is halogen, the rest of $X_1$, $X_2$, $X_3$ and $X_4$ are not hydrogen simultaneously, According to a further aspect, the present application relates to a compound of general formula (Ia), a single stereoisomer thereof, a mixture of stereoisomers thereof, and a prodrug, pharmaceutically acceptable salt and metabolite thereof:

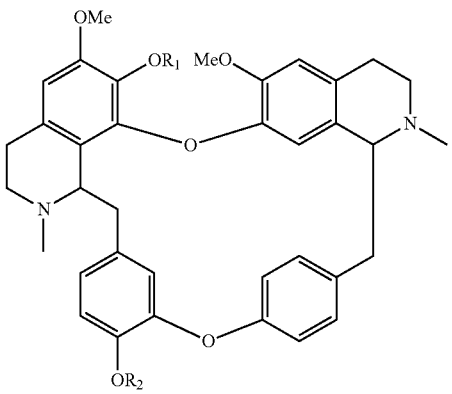

(Ia)

wherein, $R_1$ is selected from nitroso, optionally substituted alkyl, optionally substituted alkenyl, optionally substituted alkynyl, optionally substituted alkylcarbonyl, optionally substituted alkenylcarbonyl, optionally substituted alkynylcarbonyl, optionally substituted cycloalkylcarbonyl, optionally substituted arylcarbonyl, optionally substituted heteroarylcarbonyl or optionally substituted sulfonyl; and $R_2$ is selected from hydrogen, optionally substituted alkyl, nitroso, optionally substituted alkylcarbonyl, optionally substituted alkenylcarbonyl, optionally substituted alkynylcarbonyl, optionally substituted cycloalkylcarbonyl, optionally substituted arylcarbonyl or optionally substituted heteroarylcarbonyl or optionally substituted sulfonyl.

In some embodiments, $R_1$ is selected from halogen substituted alkylcarbonyl, halogen substituted alkenylcarbonyl, halogen substituted alkynylcarbonyl, halogen substituted cycloalkylcarbonyl, halogen substituted arylcarbonyl or halogen substituted heteroarylcarbonyl.

In some embodiments, $R_1$ is selected from cyan substituted alkylcarbonyl, cyan substituted alkenylcarbonyl, cyan substituted alkynylcarbonyl, cyan substituted cycloalkylcarbonyl, cyan substituted arylcarbonyl orcyan substituted heteroarylcarbonyl.

In some embodiments, $R_1$ is selected from hydroxy substituted alkylcarbonyl, hydroxy substituted alkenylcarbonyl, hydroxy substituted alkynylcarbonyl, hydroxy substituted cycloalkylcarbonyl, hydroxy substituted arylcarbonyl or hydroxy substituted heteroarylcarbonyl.

In some embodiments, $R_1$ is selected from nitro substituted alkylcarbonyl, nitro substituted alkenylcarbonyl, nitro substituted alkynylcarbonyl, nitro substituted cycloalkylcarbonyl, nitro substituted arylcarbonyl or nitro substituted heteroarylcarbonyl.

In some embodiments, $R_1$ is selected from optionally substituted alkyl substituted alkylcarbonyl, alkenylcarbonyl substituted with optionally substituted alkyl, alkynylcarbonyl substituted with optionally substituted alkyl, cycloalkylcarbonyl substituted with optionally substituted alkyl, arylcarbonyl substituted with optionally substituted alkyl or heteroarylcarbonyl substituted with optionally substituted alkyl.

In some embodiments, $R_1$ is selected from alkylcarbonyl substituted with optionally substituted alkoxy, alkenylcarbonyl substituted with optionally substituted alkoxy, alkynylcarbonyl substituted with optionally substituted alkoxy, cycloalkylcarbonyl substituted with optionally substituted alkoxy, arylcarbonyl substituted with optionally substituted alkoxy or heteroarylcarbonyl substituted with optionally substituted alkoxy.

In some embodiments, $R_1$ is selected from trifluoromethylcarbonyl, chloromethylcarbonyl or 3-trifluoromethylphenylcarbonyl.

The different groups or substituents of the above-mentioned can be combined optionally.

According to a further aspect, the present application relates to the compound, a single stereoisomer thereof, a mixture of stereoisomers thereof, and a prodrug, pharmaceutically acceptable salt and metabolite thereof, wherein the compound is selected from:

H-01
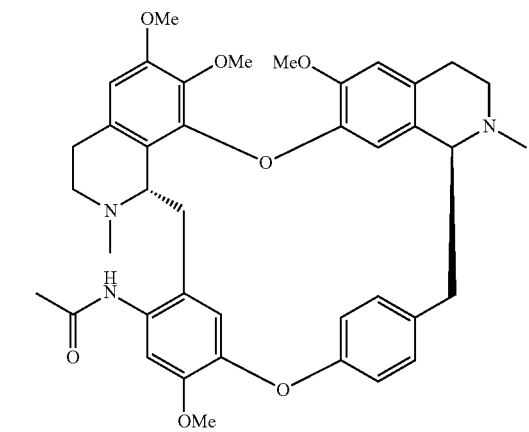

H-02
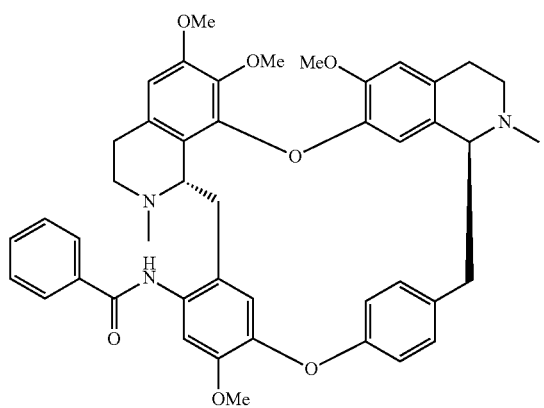

H-03
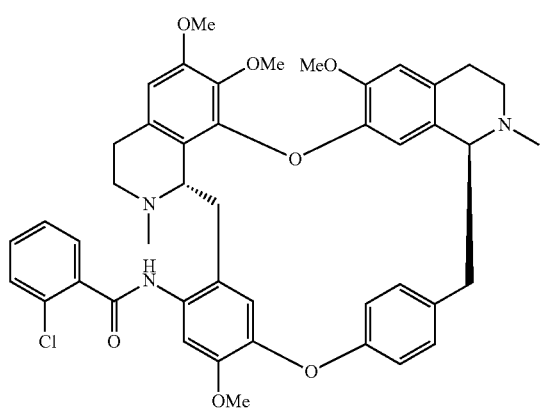

H-04
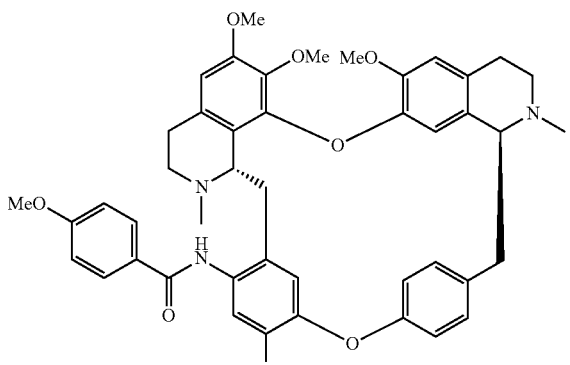

H-05
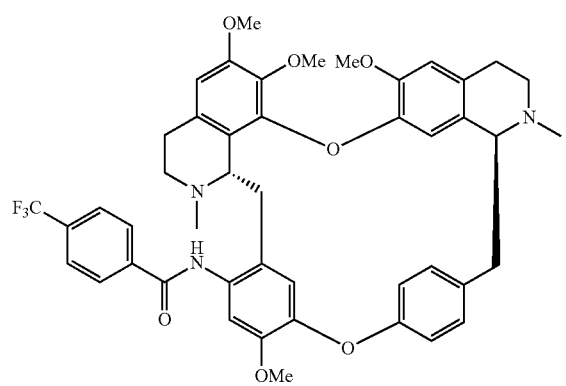

H-06
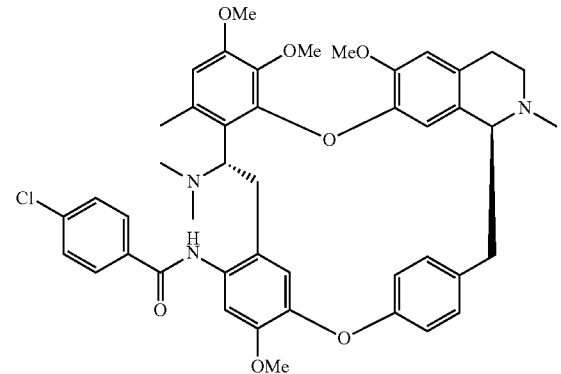

H-07
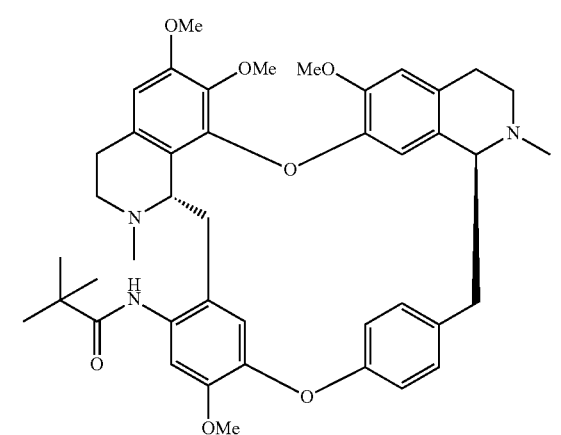

H-08
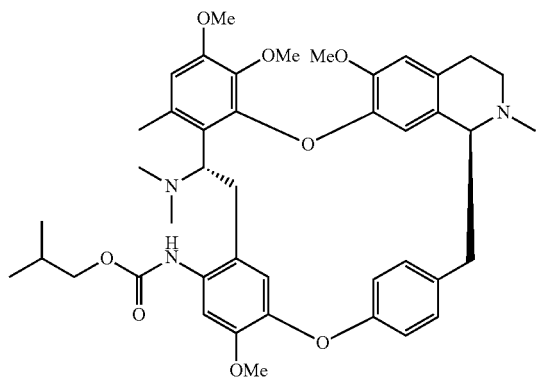
H-11
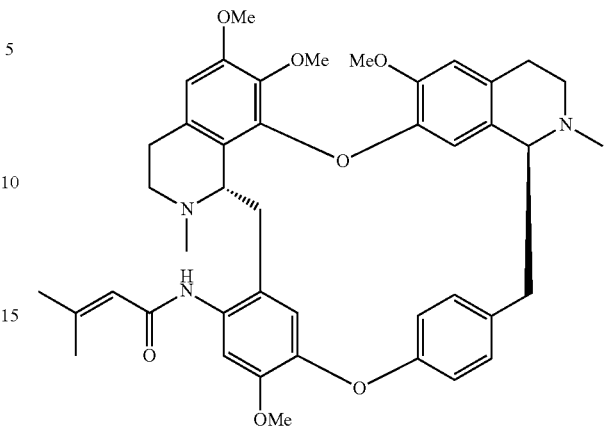
H-09
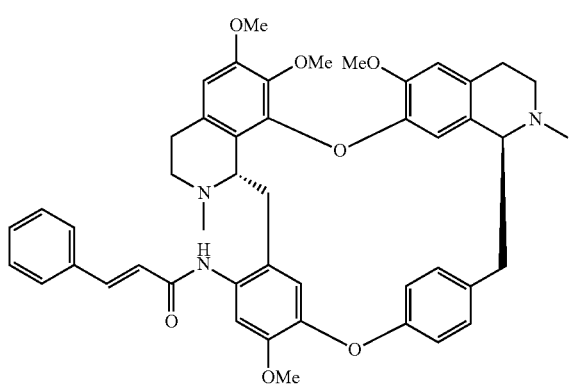
H-12
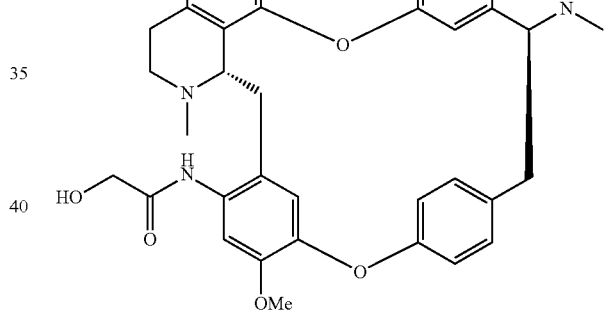
H-10
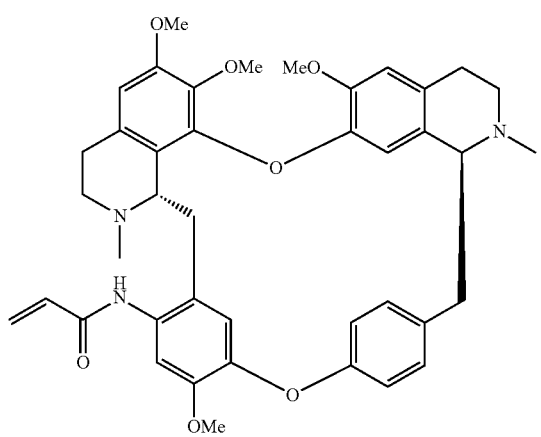
H-13
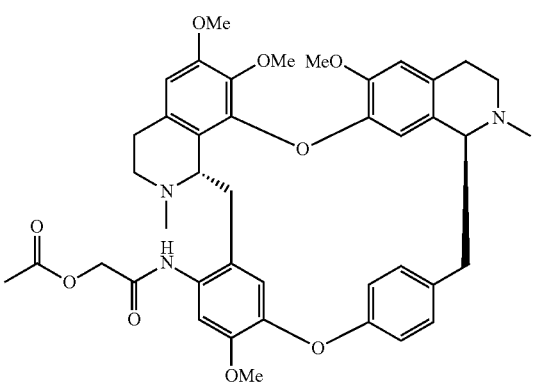

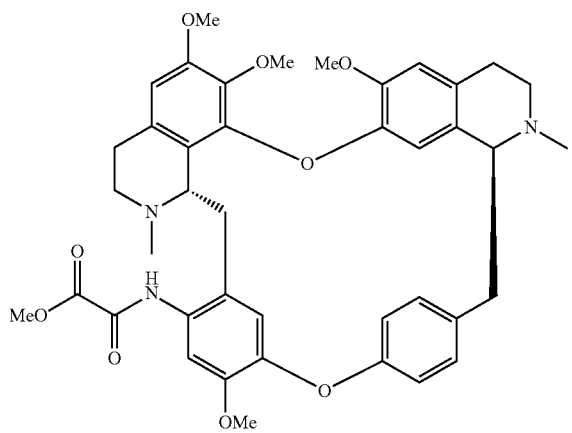
H-14
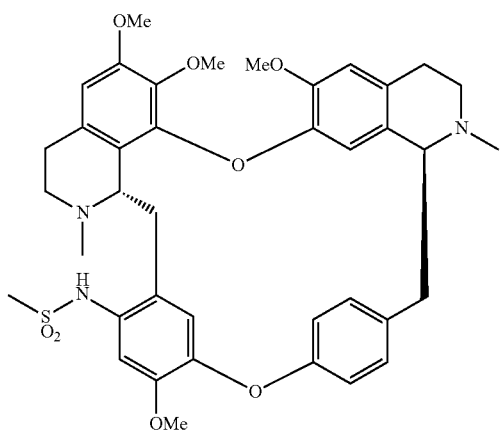
H-17
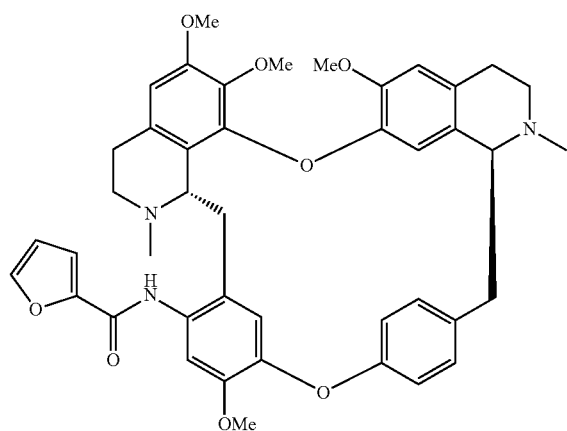
H-15
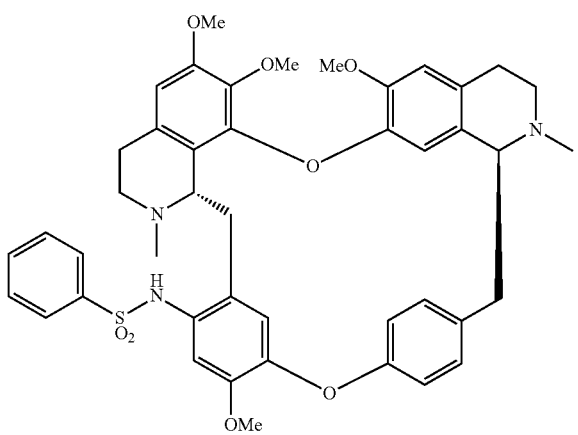
H-18
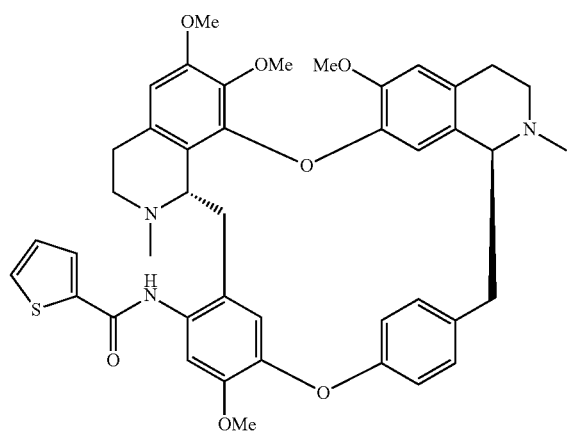
H-16
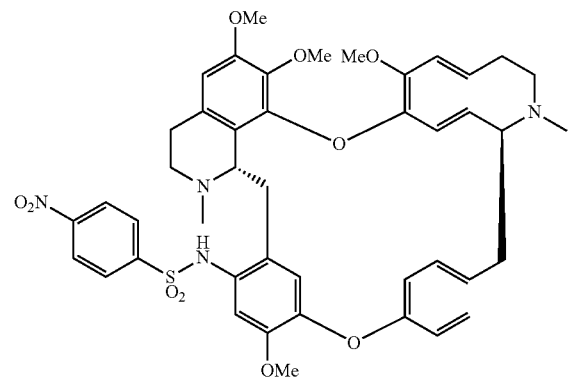
H-19

-continued
H-20
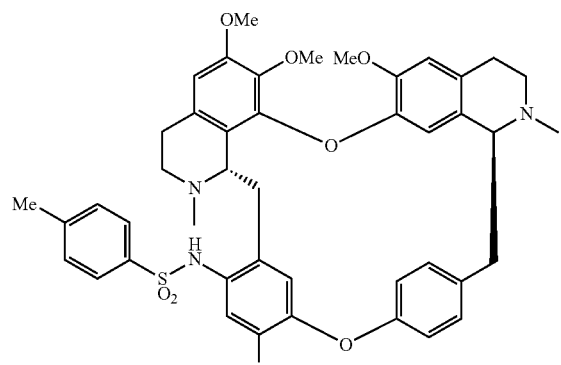
H-21
H-22
H-23
-continued
H-24
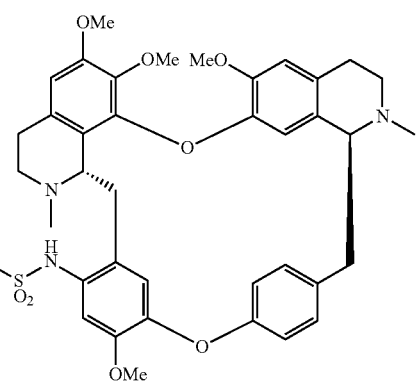
H-25
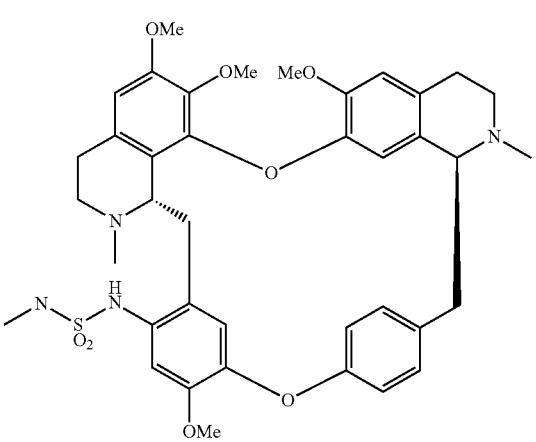
H-26
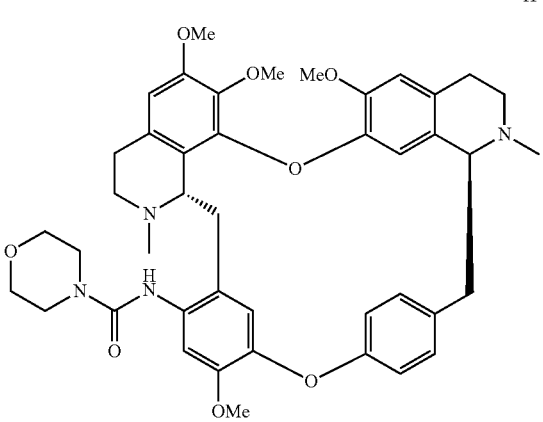

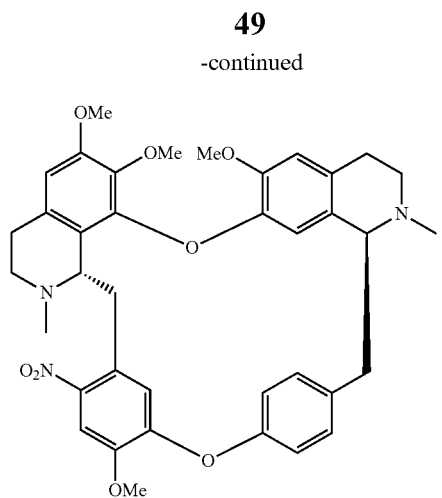
H-27
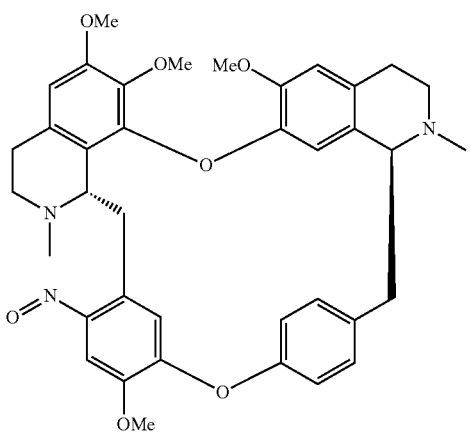
H-30
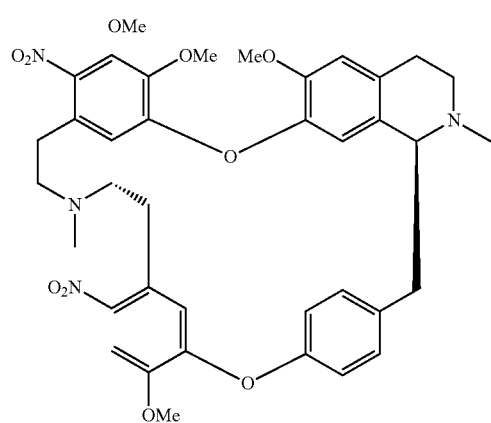
H-28
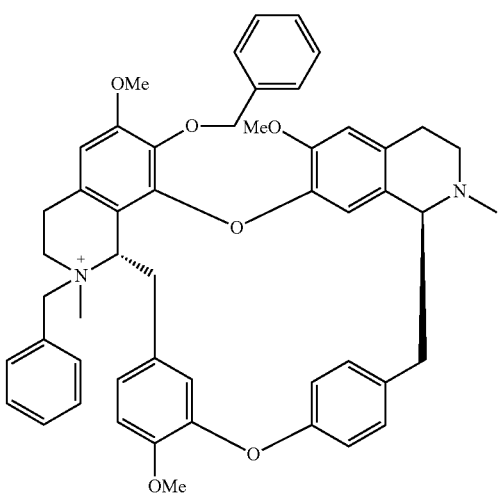
H-31
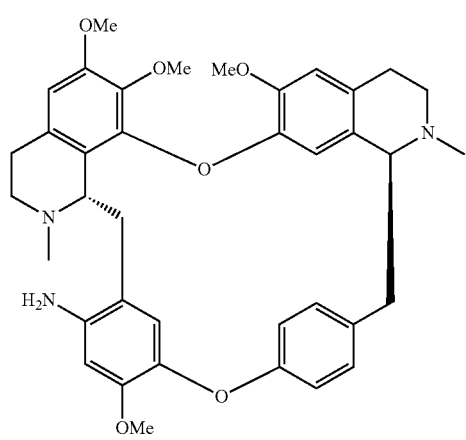
H-29
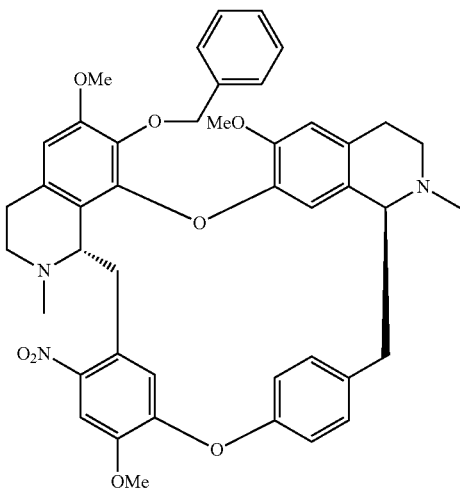
H-32

-continued
H-33
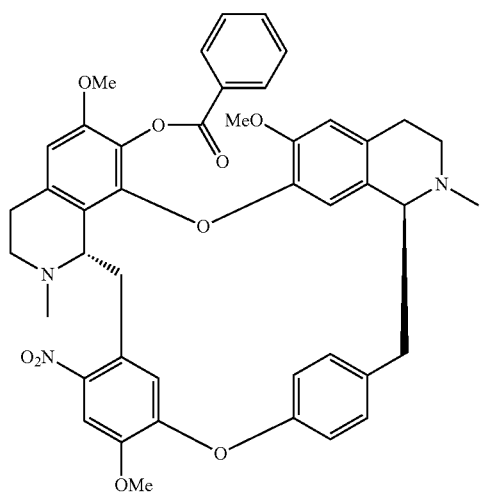
H-34
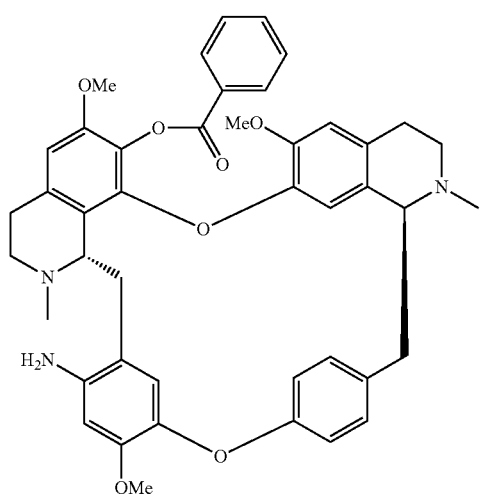
H-35
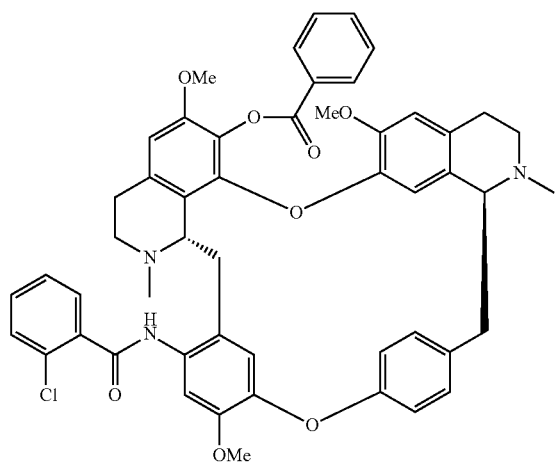
-continued
H-36
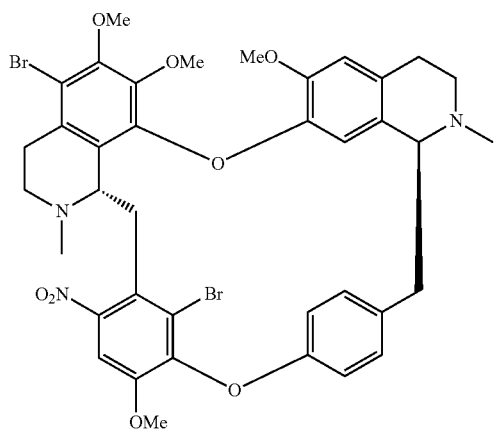
H-37
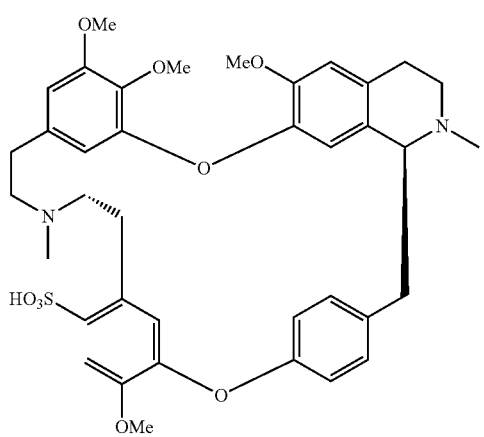
H-38
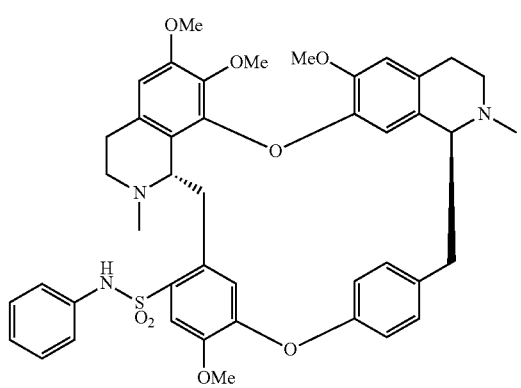

-continued
H-39
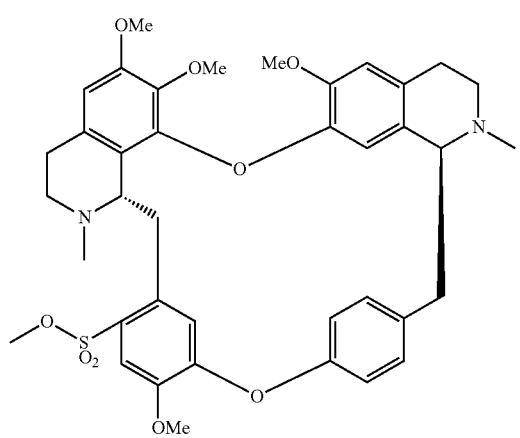
H-42
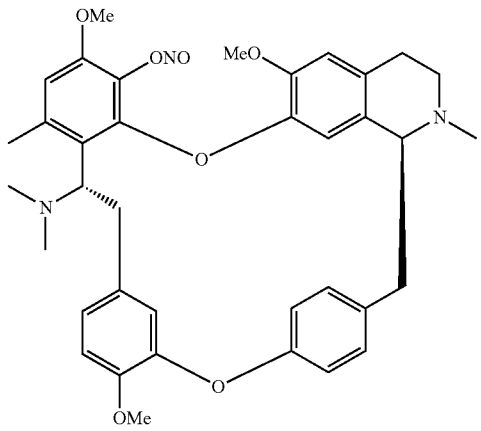
H-40
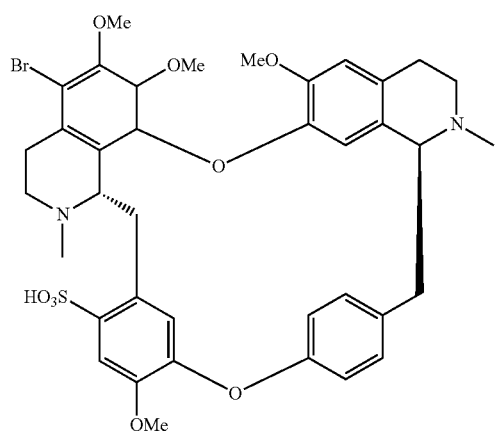
H-43
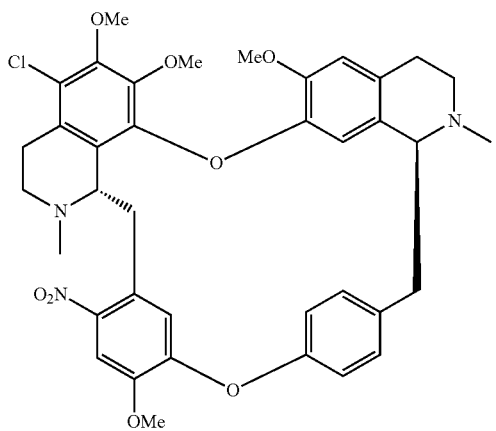
H-41
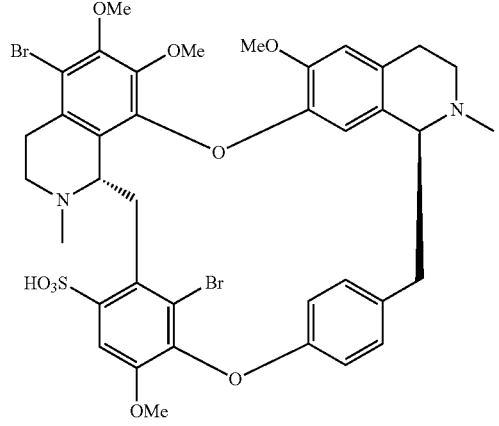
H-44
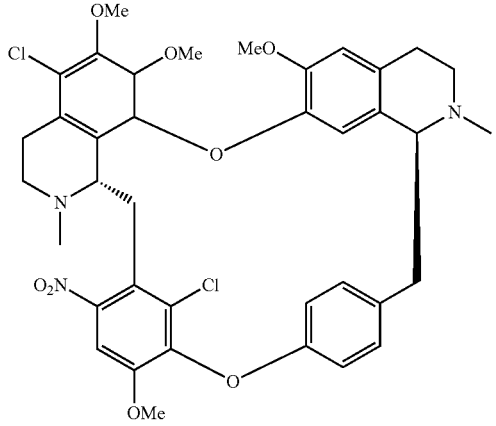

H-45
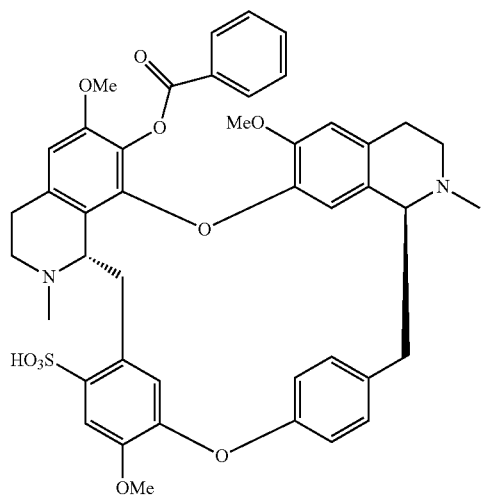
H-46
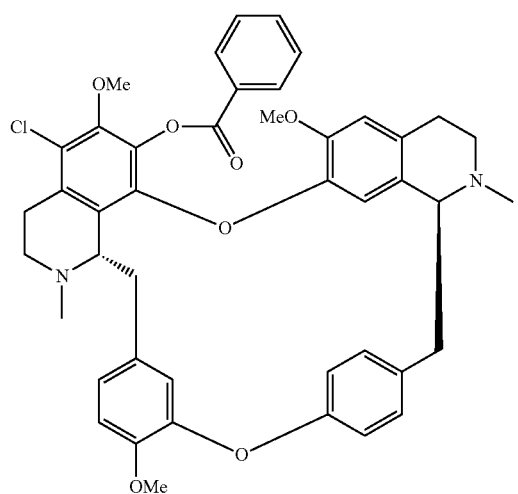
H-47
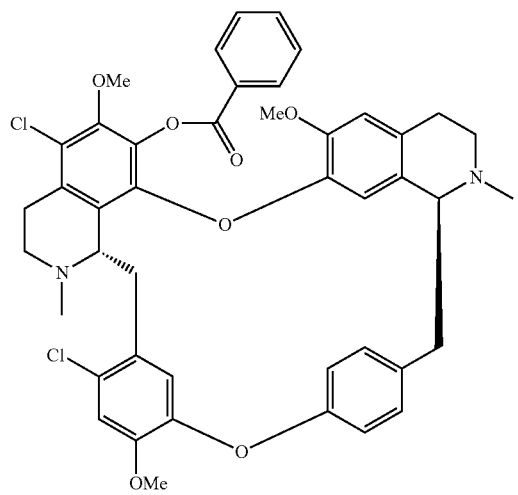
H-48
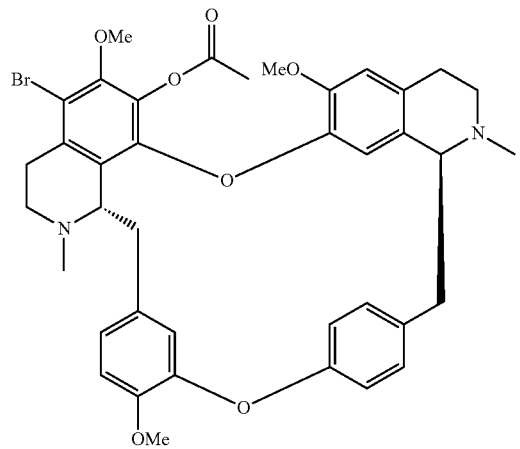
H-49
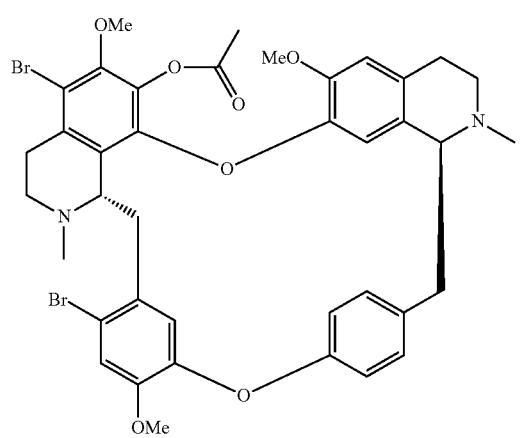
H-50
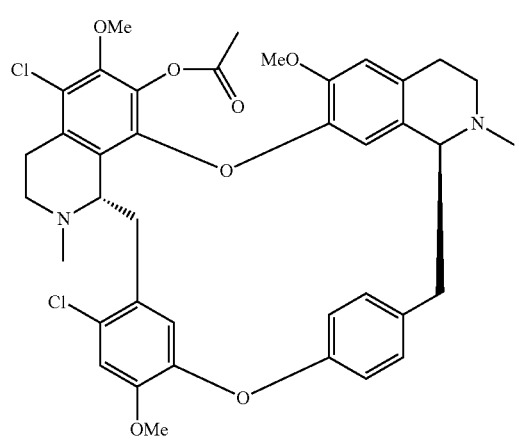

H-51
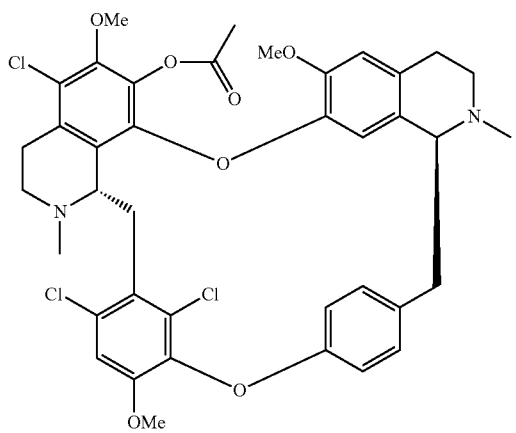

H-54
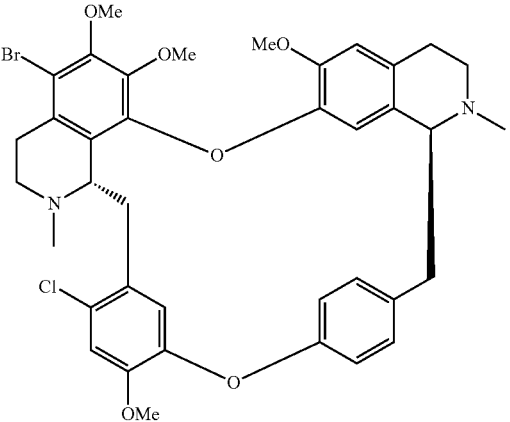

H-52
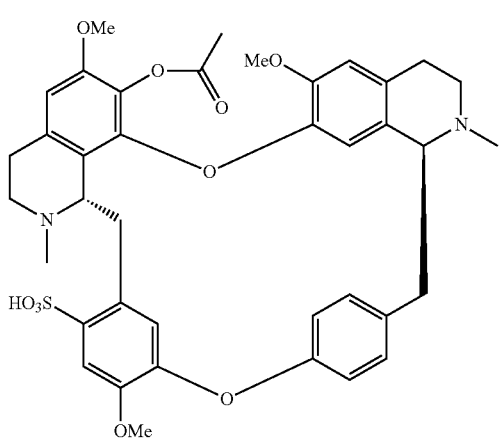

H-55
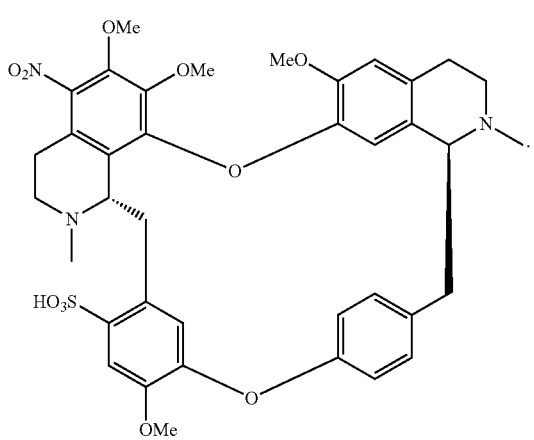

H-53
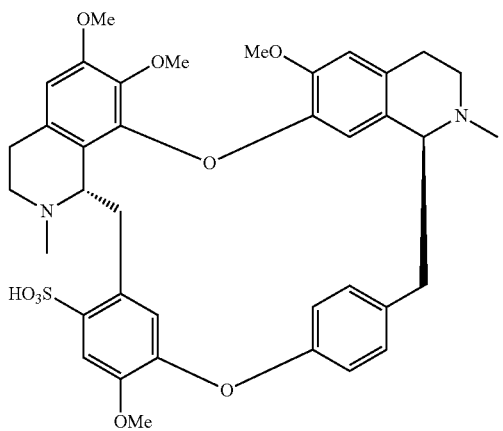

According to a further aspect, the present application relates to a pharmaceutical composition comprising a compound of general formula (I), general formula (Ia), or any one of H-01 to H-55, a single stereoisomer thereof, a mixture of stereoisomers thereof, and a prodrug, pharmaceutically acceptable salt and metabolite thereof, and a pharmaceutically acceptable carrier.

The exemplary dosage forms of the pharmaceutical composition in the present application include but are not limited to, for example tablet, capsule, pill, suppository, cream, ointment, injection or infusion.

According to a further aspect, the present application relates to a method of preparing compound of general formula (I), a single stereoisomer thereof, a mixture of stereoisomers thereof, and a prodrug, pharmaceutically acceptable salt and metabolite thereof,

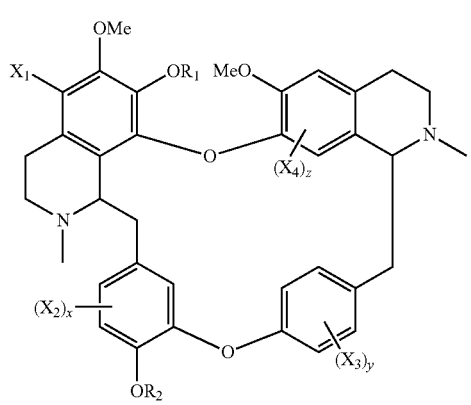 (I)

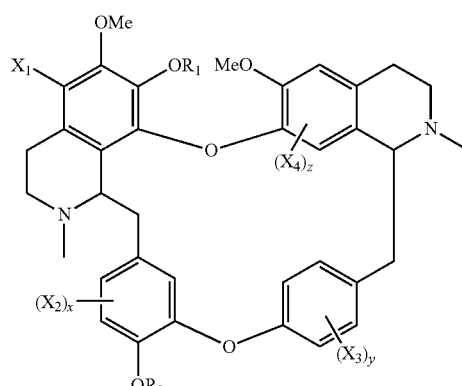 (I)

wherein, $X_1$, $X_2$, $X_3$ and $X_4$ are independently nitro; or $X_1$, $X_2$, $X_3$ and $X_4$ are independently hydrogen or nitro, provided that: $X_1$, $X_2$, $X_3$ and $X_4$ are not hydrogen simultaneously;

$R_1$ and $R_2$ are independently selected from hydrogen, nitroso, optionally substituted alkyl, optionally substituted alkenyl, optionally substituted alkynyl, optionally substituted cycloalkyl, optionally substituted sulfonyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

x is 1, 2 or 3;

y is 1, 2, 3 or 4; and z is 1 or 2;

wherein the method comprises the nitrification reaction of berbamine, tetrandrine or tetrandrine B.

In some embodiments, the nitrification reaction is performed using mixed acid of acetic anhydride and nitric acid.

In some embodiments, the nitrification reaction is performed in non-polar solvent.

The exemplary non-polar solvents using in the above-mentioned nitrification reaction include but are not limited to, for example dichloromethane, chloroform and 1,2-dichloroethane.

In some embodiments, the nitrification reaction is performed at about −10° C. to about 5° C., preferably 0° C.

In some embodiments, the nitrification reaction is performed at about 0° C.

In some embodiments, the nitrification reaction is performed in inert gas.

The exemplary inert gases using in the above-mentioned nitrification reaction include but are not limited to, for example argon, helium or nitrogen.

According to a further aspect, the present application relates to a method of preparing compound of general formula (I), a single stereoisomer thereof, a mixture of stereoisomers thereof, and a prodrug, pharmaceutically acceptable salt and metabolite thereof, wherein, $X_1$, $X_2$, $X_3$ and $X_4$ are independently amino; or $X_1$, $X_2$, $X_3$ and $X_4$ are independently hydrogen or amino, provided that: $X_1$, $X_2$, $X_3$ and $X_4$ are not hydrogen simultaneously;

$R_1$ and $R_2$ are independently selected from hydrogen, nitroso, optionally substituted alkyl, optionally substituted alkenyl, optionally substituted alkynyl, optionally substituted cycloalkyl, optionally substituted sulfonyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

x is 1, 2 or 3;

y is 1, 2, 3 or 4; and z is 1 or 2;

wherein the method comprises the nitrification reaction of berbamine, tetrandrine or tetrandrine B, and then the reduction reaction of nitrification product.

In some embodiments, $NaBH_4$ is used in the reduction reaction.

In some embodiments, $NiCl_2.6H_2O$ is used as catalyst in the reduction reaction.

In some embodiments, the reduction reaction is performed at −15° C. to 0° C.

In some embodiments, the reduction reaction is performed in ice-bath.

In some embodiments, the reduction reaction is performed in polar aprotic solvent.

The exemplary polar aprotic solvents using in the above-mentioned reduction reaction include but are not limited to, for example tetrahydrofuran, 1,4-dioxane and dimethyl formamide.

According to a further aspect, the present application relates to a method of preparing compound of general formula (I), a single stereoisomer thereof, a mixture of stereoisomers thereof, and a prodrug, pharmaceutically acceptable salt and metabolite thereof,

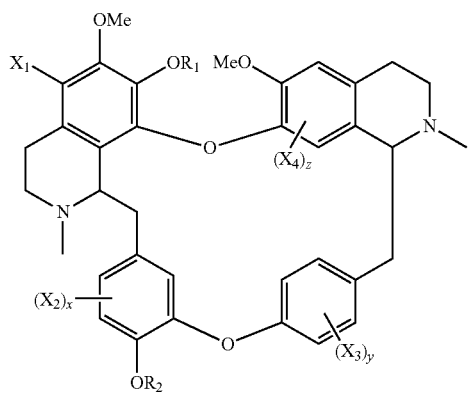 (I)

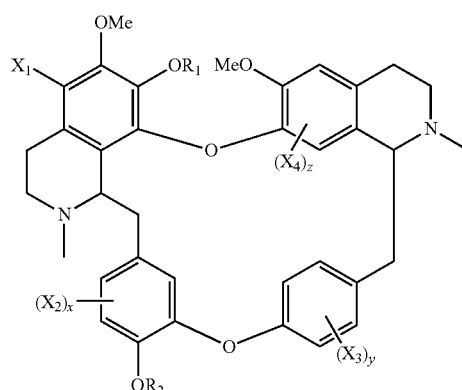 (I)

wherein, $X_1$, $X_2$, $X_3$ and $X_4$ are independently carbonyl substituted amino; or $X_1$, $X_2$, $X_3$ and $X_4$ are independently hydrogen or —$NR_3$—C(=O)—$R_4$, provided that: $X_1$, $X_2$, $X_3$ and $X_4$ are not hydrogen simultaneously;

$R_1$ is selected from hydrogen, optionally substituted alkyl, nitroso, optionally substituted alkenyl, optionally substituted alkynyl, optionally substituted cycloalkyl, optionally substituted aryl, optionally substituted heteroaryl, optionally substituted arylcarbonyl, optionally substituted heteroarylcarbonyl, optionally substituted sulfonyl, optionally substituted alkylcarbonyl, optionally substituted alkenylcarbonyl or optionally substituted alkynylcarbonyl;

x is 1, 2 or 3;

y is 1, 2, 3 or 4; and z is 1 or 2;

wherein the method comprises the nitrification reaction of berbamine, tetrandrine or tetrandrine B, and then the reduction reaction of nitrification product and the acylation reaction of the reduction product.

In some embodiments, the acyl halides or sulfonyl halides is used in the acylation reaction.

In some embodiments, the acylation reaction is performed in basic solven.

The exemplary basic solvents using in the above-mentioned acylation reaction include but are not limited to, for example pyridine, diethylamine in dichloromethane solution and triethylamine in dichloromethane solution.

In some embodiments, the acylation reaction is performed in 0° C. to room temperature.

In some embodiments, the acylation reaction is performed in ice-bath.

In some embodiments, the acylation reaction is performed in inert gas.

The exemplary inert gases using in the above-mentioned acylation reaction include but are not limited to, for example argon, helium or nitrogen.

According to a further aspect, the present application relates to a method of preparing compound of general formula (I), a single stereoisomer thereof, a mixture of stereoisomers thereof, and a prodrug, pharmaceutically acceptable salt and metabolite thereof, wherein, $X_1$, $X_2$, $X_3$ and $X_4$ are independently —$SO_3H$; or $X_1$, $X_2$, $X_3$ and $X_4$ are independently hydrogen or —$SO_3H$, provided that: $X_1$, $X_2$, $X_3$ and $X_4$ are not hydrogen simultaneously;

$R_1$ and $R_2$ are independently selected from hydrogen, nitroso, optionally substituted alkyl, optionally substituted alkenyl, optionally substituted alkynyl, optionally substituted cycloalkyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

x is 1, 2 or 3;

y is 1, 2, 3 or 4; and z is 1 or 2;

wherein the method comprises the sulfonation reaction of berbamine, tetrandrine or tetrandrine B.

In some embodiments, sulfate and concentrated sulfuric acid are used in the sulfonation reaction.

In some embodiments, the sulfonation reaction is performed in non-polar solvent.

The exemplary inert gases using in the above-mentioned acylation reaction include but are not limited to non-polar solvents, for example dichloromethane, chloroform, or 1,2-dichloroethane.

In some embodiments, the sulfonation reaction is performed at about −15° C. to 0° C.

In some embodiments, the sulfonation reaction is performed in ice-bath.

According to a further aspect, the present application relates to a method of preparing compound of general formula (I), a single stereoisomer thereof, a mixture of stereoisomers thereof, and a prodrug, pharmaceutically acceptable salt and metabolite thereof,

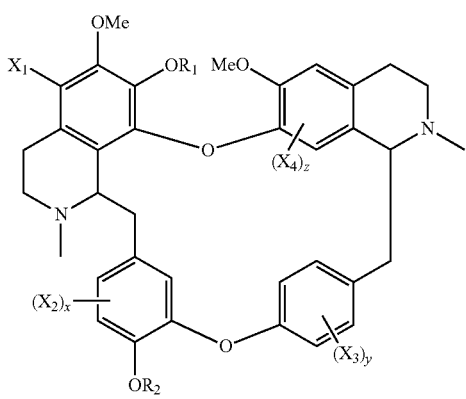

wherein,

X₁, X₂, X₃ and X₄ are independently hydrogen or —NH—S(=O)₂—R₆, provided that: X₁, X₂, X₃ and X₄ are not hydrogen simultaneously;

R₁ and R₂ are independently selected from hydrogen, nitroso, optionally substituted alkyl, optionally substituted alkenyl, optionally substituted alkynyl, optionally substituted cycloalkyl, optionally substituted aryl, optionally substituted heteroaryl, optionally substituted arylcarbonyl, optionally substituted heteroarylcarbonyl, optionally substituted alkylcarbonyl, optionally substituted alkenylcarbonyl or optionally substituted alkynylcarbonyl;

R₆ is selected from optionally substituted alkyl, optionally substituted alkenyl, optionally substituted alkynyl, optionally substituted cycloalkyl, optionally substituted aryl, optionally substituted heteroaryl, optionally substituted heterocyclyl or optionally substituted amino;

x is 1, 2 or 3;
y is 1, 2, 3 or 4; and
z is 1 or 2;

the method comprises the nitrification reaction of reacting berbamine, tetrandrine or tetrandrine B with concentrated nitric acid, performing reduction reaction using Fe powder, generating amino group, and then carrying out base catalyzed reaction of amino group with acid chloride, generating the compound of general formula (I).

According to a further aspect, the present application relates to a method of treating or preventing hepatopathy, the method comprising administering to a subject in need thererof an therapeutically effective amount of a compound of general formula (I), a compound of general formula (Ia) or any one of H-1 to H-55 a single stereoisomer thereof, a mixture of stereoisomers thereof, and a prodrug, pharmaceutically acceptable salt and metabolite thereof, according to any one of 1 to 20, or the above-mentioned pharmaceutical composition.

In some embodiments, the subject is mammal.
In some embodiments, the mammal is human.
In some embodiments, the hepatopathy is viral liver disease and non-viral liver disease.

The exemplary hepatopathy which can be treated or prevented using the compound in the the present application, include but are not limited to, for example hepatitis, alcoholic liver disease, drug or toxin-induced liver disease, metabolic abnormal liver disease and fatty liver disease.

EXAMPLES

Although any one skilled in the art is capable of preparing the compounds of the present application according to the general techniques disclosed herein above, more specific details on synthetic techniques for the compound of the present application are provided elsewhere in this specification for conveniences. In addition, all reagents and reaction conditions employed in synthesis are known to those skilled in the art and are available from ordinary commercial sources.

Example 1

The Preparation of Tetrandrine Nitro-Derivative H-27

At 0° C. and under nitrogen atmosphere, to a 10 mL round flask was added (CH₃CO)₂O (1.5 mL), after that concentrated nitric acid (0.6 mL) were dropped slowly with stirring. The resultant mixture was slowly cooled to −10° C. after stirring for 5 min to obtain mixed acid. To the mixed acid was dropped slowly tetrandrine (500 mg, 0.8 mmol) in absolute chloroform (3 mL) for 15 min.

The reaction was carried on for 70 min with TLC detection and was stopped by water. PH was adjusted with stronger ammonia water, extracted with chloroform completely, washed with saturated NaCl solution, dried over anhydrous MgSO₄, filtered and evaporated to dryness. Chloroform was recovered to give solid product (610 mg), purified by column chromatography (chloroform:methanol=50:1) to give pure compound H-27 (496 mg, yield 92%).

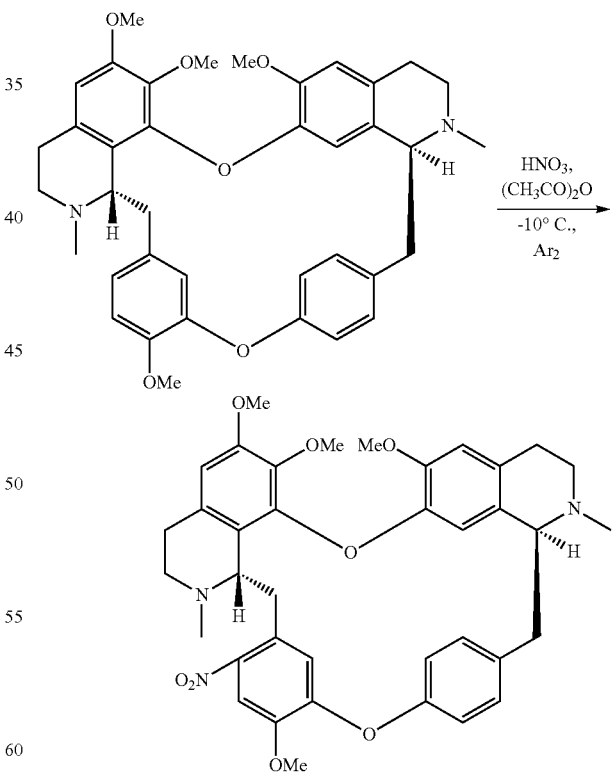

Spectral Data
MS data is obtained by Agilent MS-5973, NMR data is obtained by Varian INOVA-400.

H-27 C₃₈H₄₁N₃O₈; EI-MS: m/z 667.32 [M]⁺; ¹H-NMR (CDCl₃, 400 MHz) δ (ppm): 7.42 (1H, s, H-13), 7.37 (1H, dd, J=2.0, 8.0 Hz, H-14'), 7.12 (1H, dd, J=2.4, 8.0 Hz, H-13'), 6.77 (1H, dd, J=2.8, 8.4 Hz, H-11'), 6.54 (1H, s, H-10), 6.52 (1H, s, H-5'), 6.30 (1H, s, H-5), 6.28 (1H, d, J=2.0 Hz, H-10'), 5.98 (1H, s, H-8'), 3.98 (3H, s, 12-OCH$_3$), 3.91 (1H, dd, J=6.0, 10.8 Hz, H-1'), 3.75 (3H, s, 6-OCH$_3$), 3.66 (1H, m, H-1), 3.38 (3H, s, 6'-OCH$_3$), 3.18 (3H, s, 7-OCH$_3$), 2.63 (3H, s, 2'-NCH$_3$), 2.21 (3H, s, 2-NCH$_3$).

In analogy with example 1, H-28 (yield 43%) was prepared, wherein the ratio of mixed acid is constant, volume is 4 mL, the time of reaction is extended to 200 min.

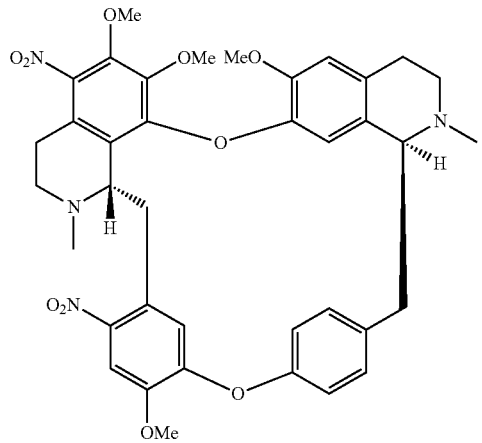 [SMILES: COc1cc([N+](=O)[O-])c2cc1Oc1ccc(cc1)C[C@H]1c3cc(c(OC)cc3CCN1C)Oc1c(OC)c(OC)c([N+](=O)[O-])c3c1[C@H](C2)N(C)CC3]

Spectral Data

H-28 C$_{38}$H$_{40}$N$_4$O$_{10}$; ESI-MS: m/z 713.74 [M+H]$^+$; $^1$H-NMR (CDCl$_3$, 400 MHz) δ (ppm): 7.42 (1H, s, H-13), 7.39 (1H, dd, J=2.4, 8.4 Hz, H-14'), 7.15 (1H, dd, J=2.8, 8.4 Hz, H-13'), 6.77 (1H, dd, J=2.4, 8.4 Hz, H-11'), 6.55 (1H, s, H-10), 6.52 (1H, s, H-5'), 6.30 (1H, dd, J=2.0, 8.4 Hz, H-10'), 6.00 (1H, s, H-8'), 3.99 (3H, s, 12-OCH$_3$), 3.79 (3H, s, 6-OCH$_3$), 3.44 (3H, s, 6'-OCH$_3$), 3.21 (3H, s, 7-OCH$_3$), 2.66 (3H, s, 2'-NCH$_3$), 2.20 (3H, s, 2-NCH$_3$).

Example 2

The Preparation of Tetrandrine Nitro- and Reductive Derivative H-29

To a 25 mL round flask were added anhydrous H-27 (100 mg, 0.15 mmol) and tetrahydrofuran (2 mL). H-27 was dissolved completely with stirring. At 0° C., to the reaction mixture was added NiCl$_2$.6H$_2$O (10.8 mg, 0.046 mmol) dissolved in methanol (1 mL). The mixture was added NaBH$_4$ (28.4 mg, 0.75 mmol) with stirring. The reaction was kept for 20 min in ice-bath. After TLC detection, the reaction is stopped and the resultant was poured in ice-water. The aqueous layer was extracted thrice with chloroform, washed with saturated NaCl solution, dried over anhydrous MgSO$_4$, filtered and evaporated to dryness. Chloroform was recovered to give solid product (96 mg), purified by column chromatography (chloroform:methanol=50:1) to obtain H-29 (78 mg, yield 78%), H-30 (12 mg, yield 12%).

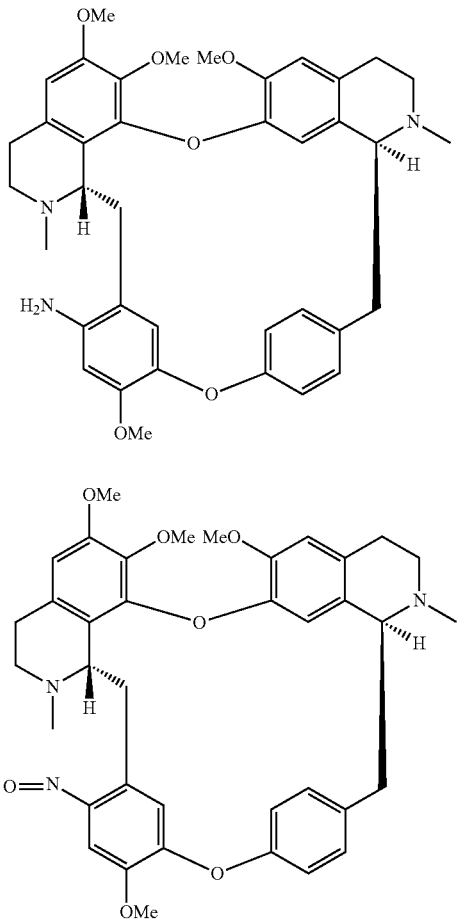

Spectral Data

H-29 C$_{38}$H$_{43}$N$_3$O$_6$; ESI-MS: m/z 638.52 [M+H]$^+$; $^1$H-NMR (CDCl$_3$, 400 MHz) δ (ppm): 7.28 (1H, d, J=9.6 Hz, H-14'), 7.18 (1H, dd, J=2.0, 8.0 Hz, H-13'), 6.60 (1H, dd, J=2.0, 8.4 Hz, H-11'), 6.50 (1H, s, H-10), 6.46 (1H, s, H-5'), 6.31 (1H, s, H-5), 6.29 (1H, s, H-13), 6.12 (1H, dd, J=1.6, 8.0 Hz, H-10'), 5.87 (1H, s, H-8'), 3.94 (1H, d, J=9.2 Hz, H-1'), 3.87 (3H, s, 12-OCH$_3$), 3.80 (1H, dd, J=5.2, 11.2 Hz, H-1), 3.73 (3H, s, 6-OCH$_3$), 3.35 (3H, s, 6'-OCH$_3$), 3.11 (3H, s, 7-OCH$_3$), 2.61 (3H, s, 2'-NCH$_3$), 2.42 (3H, s, 2-NCH$_3$).

H-30 C$_{38}$H$_{41}$N$_3$O$_7$; ESI-MS: m/z 652.34 [M+H]$^+$; $^1$H-NMR (CDCl$_3$, 400 MHz) δ (ppm): 7.33 (1H, dd, J=2.4, 8.4 Hz, H-14'), 7.21 (1H, dd, J=2.4, 8.0 Hz, H-13'), 6.60 (1H, dd, J=2.8, 8.4 Hz, H-11'), 6.50 (1H, s, H-13), 6.47 (1H, s, H-10), 6.32 (1H, s, H-5), 6.31 (1H, s, H-5'), 6.04 (1H, dd, J=2.4, 8.4 Hz, H-10'), 5.89 (1H, s, H-8'), 3.92 (1H, m, H-1'), 3.88 (3H, s, 12-OCH$_3$), 3.80 (1H, m, H-1), 3.75 (3H, s, 6-OCH$_3$), 3.49 (3H, s, 6'-OCH$_3$), 3.36 (3H, s, 7-OCH$_3$), 2.66 (3H, s, 2'-NCH$_3$), 2.42 (3H, s, 2-NCH$_3$).

Example 3

The Preparation of Tetrandrine Amidated and Sulfonamide Derivative

To a 10 mL round flask were added anhydrous H-29 (50 mg, 0.08 mmol). At 0° C. and under Ar atmosphere, to the mixture was added pyridine (1.5 mL). H-29 was dissolved completely with stirring. To the mixture was added acyl chloride (1.5 eq.), the reaction was kept for 3 h to 4 h with TLC detection and stopped. The mixture was poured in ice-water, adjusted pH to alkaline with saturated NaHCO$_3$ solution. The aqueous layer was extracted thrice with chloroform., washed with saturated NaCl solution, dried over anhydrous MgSO$_4$, filtered and evaporated to dryness. The Chloroform was recovered. The crude product was separated by column chromatography (chloroform:methanol=40:1) to give pure product.

In analogy with example 3, 26 of amidated and sulfonamide compounds (H-01 to H-26, yield 40%-80%) were prepared except that the corresponding acyl chloride compounds were used.

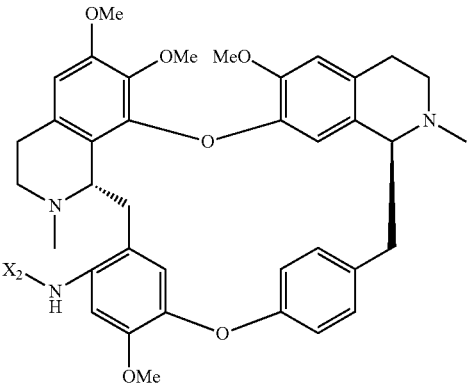

| No. | Sample | X$_2$ |
|---|---|---|
| 1 | H-01 |  |
| 2 | H-02 | 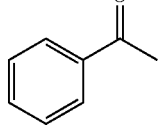 |
| 3 | H-03 | 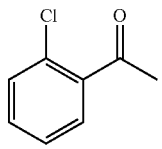 |
| 4 | H-04 | 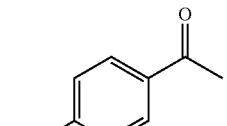 |
| 5 | H-05 | 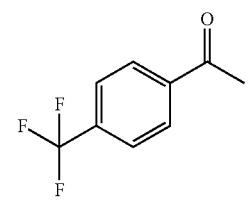 |

-continued

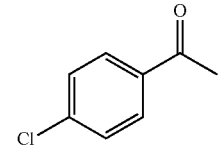

| No. | Sample | X$_2$ |
|---|---|---|
| 6 | H-06 | 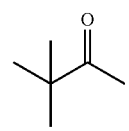 |
| 7 | H-07 | 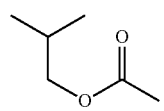 |
| 8 | H-08 | 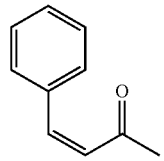 |
| 9 | H-09 | 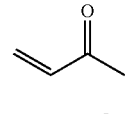 |
| 10 | H-10 | 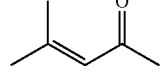 |
| 11 | H-11 | 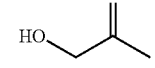 |
| 12 | H-12 | 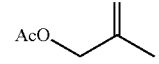 |
| 13 | H-13 | 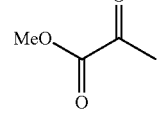 |
| 14 | H-14 | |

69
-continued

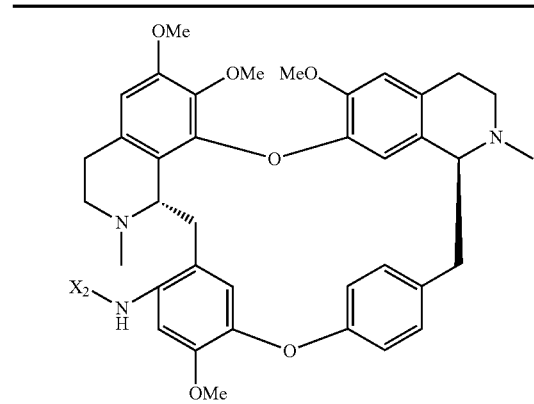

| No. | Sample | X₂ |
|---|---|---|
| 15 | H-15 | 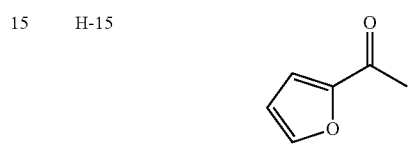 |
| 16 | H-16 | 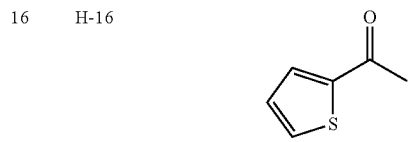 |
| 17 | H-17 |  |
| 18 | H-18 | 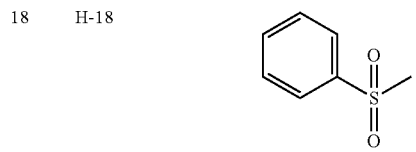 |
| 19 | H-19 | 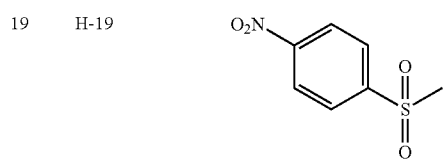 |
| 20 | H-20 | 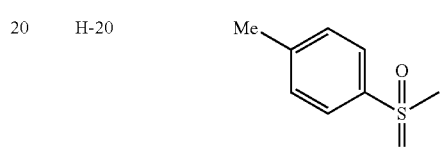 |
| 21 | H-21 | 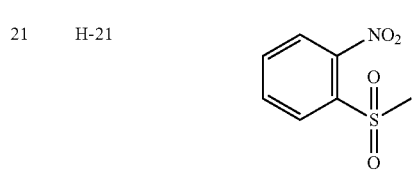 |

70
-continued

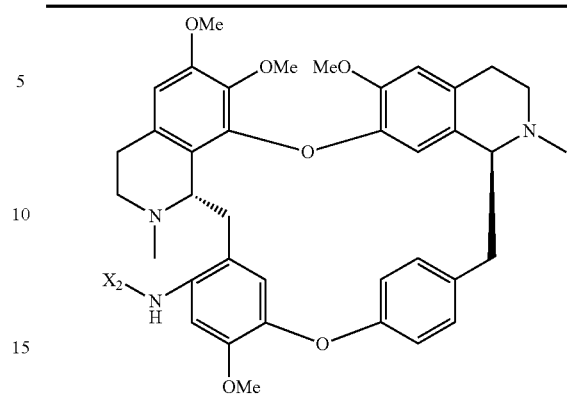

| No. | Sample | X₂ |
|---|---|---|
| 22 | H-22 |  |
| 23 | H-23 |  |
| 24 | H-24 | 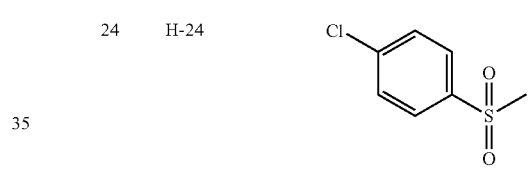 |
| 25 | H-25 |  |
| 26 | H-26 | 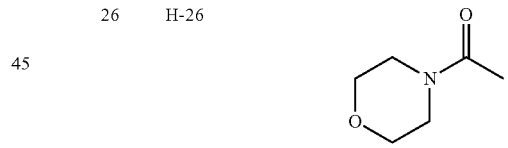 |

Spectral Data

H-01 $C_{40}H_{45}N_3O_7$; ESI-MS: m/z 680.23 [M+H]⁺; ¹H-NMR (CDCl₃, 400 MHz) δ (ppm): 12.02 (1H, s, —CONH—), 7.90 (1H, s, H-13), 7.30 (1H, dd, J=1.6, 8.0 Hz, H-14'), 7.22 (1H, dd, J=2.4, 8.0 Hz, H-13'), 6.59 (1H, d, J=2.8 Hz, H-11'), 6.57 (1H, s, H-10), 6.47 (1H, s, H-5'), 6.32 (1H, s, H-5), 6.13 (1H, dd, J=2.0, 8.4 Hz, H-10'), 5.89 (1H, s, H-8'), 3.99 (1H, d, J=9.2 Hz, H-1'), 3.94 (3H, s, 12-OCH₃), 3.82 (1H, dd, J=5.2, 11.2 Hz, H-1), 3.75 (3H, s, 6-OCH₃), 3.37 (3H, s, 6'-OCH₃), 3.10 (3H, s, 7-OCH₃), 2.61 (3H, s, 2'-NCH₃), 2.51 (3H, s, 2-NCH₃).

H-02 $C_{45}H_{47}N_3O_7$; ESI-MS: m/z 742.51 [M+H]⁺; ¹H-NMR (CDCl₃, 400 MHz) δ (ppm): 12.27 (1H, s, —CONH—), 7.81 (1H, s, H-13), 7.36 (1H, dd, J=1.6, 10.0 Hz, H-14'), 7.24 (1H, dd, J=2.4, 10.4 Hz, H-13'), 6.63 (1H, d, J=2.4 Hz, H-11'), 6.62 (1H, s, H-10), 6.48 (1H, s, H-5'), 6.25 (1H, s, H-5), 6.15 (1H, dd, J=2.0, 8.4 Hz, H-10'), 5.90

(1H, s, H-8'), 4.04 (1H, d, J=9.2 Hz, H-1'), 3.97 (3H, s, 12-OCH$_3$), 3.84 (1H, d, J=6.0 Hz, H-1), 3.72 (3H, s, 6-OCH$_3$), 3.37 (3H, s, 6'-OCH$_3$), 3.10 (3H, s, 7-OCH$_3$), 2.62 (3H, s, 2'-NCH$_3$), 2.47 (3H, s, 2-NCH$_3$).

H-03 C$_{45}$H$_{46}$ClN$_3$O$_7$; ESI-MS: m/z 776.26 [M+H]$^+$; $^1$H-NMR (CDCl$_3$, 400 MHz) δ (ppm): 12.80 (1H, s, —CONH—), 8.10 (1H, s, H-13), 7.31 (1H, dd, J=2.0, 8.4 Hz, H-14'), 7.23 (1H, dd, J=2.4, 8.0 Hz, H-13'), 6.60 (1H, d, J=2.4 Hz, H-11'), 6.59 (1H, s, H-10), 6.45 (1H, s, H-5'), 6.21 (1H, s, H-5), 6.14 (1H, dd, J=1.6, 8.4 Hz, H-10'), 5.88 (1H, s, H-8'), 4.00 (3H, s, 12-OCH$_3$), 3.93 (1H, d, J=9.2 Hz, H-1'), 3.81 (1H, dd, J=5.2, 11.2 Hz, H-1), 3.71 (3H, s, 6-OCH$_3$), 3.33 (3H, s, 6'-OCH$_3$), 3.07 (3H, s, 7-OCH$_3$), 2.60 (3H, s, 2'-NCH$_3$), 2.17 (3H, s, 2-NCH$_3$).

H-04 C$_{46}$H$_{49}$N$_3$O$_8$; ESI-MS: m/z 772.54 [M+H]$^+$; $^1$H-NMR (CDCl$_3$, 400 MHz) δ (ppm): 7.76 (1H, s, H-13), 7.32 (1H, dd, J=1.6, 7.6 Hz, H-14'), 7.23 (1H, dd, J=2.8, 8.0 Hz, H-13'), 6.63 (1H, d, J=2.8 Hz, H-11'), 6.61 (1H, s, H-10), 6.49 (1H, s, H-5'), 6.26 (1H, s, H-5), 6.15 (1H, dd, J=2.0, 8.4 Hz, H-10'), 5.90 (1H, s, H-8'), 4.04 (1H, d, J=9.2 Hz, H-1'), 3.96 (3H, s, 12-OCH$_3$), 3.84 (1H, dd, J=5.2, 10.4 Hz, H-1), 3.72 (3H, s, 6-OCH$_3$), 3.37 (3H, s, 6'-OCH$_3$), 3.10 (3H, s, 7-OCH$_3$), 2.63 (3H, s, 2'-NCH$_3$), 2.49 (3H, s, 2-NCH$_3$).

H-05 C$_{46}$H$_{46}$N$_3$O$_7$F$_3$; ESI-MS: m/z 810.57 [M+H]$^+$; $^1$H-NMR (CDCl$_3$, 400 MHz) δ (ppm): 12.42 (1H, s, CONH), 7.80 (1H, s, H-13), 7.32 (1H, dd, J=2.4, 8.4 Hz, H-14'), 7.23 (1H, dd, J=2.4, 8.0 Hz, H-13'), 6.63 (1H, s, H-10), 6.61 (1H, dd, J=2.8, 8.4 Hz, H-11'), 6.48 (1H, s, H-5'), 6.25 (1H, s, H-5), 6.15 (1H, dd, J=2.0, 8.4 Hz, H-10'), 5.89 (1H, s, H-8'), 4.04 (1H, d, J=9.2 Hz, H-1'), 3.97 (3H, s, 12-OCH$_3$), 3.80 (1H, dd, J=5.6, 10.8 Hz, H-1), 3.72 (3H, s, 6-OCH$_3$), 3.37 (3H, s, 6'-OCH$_3$), 3.08 (3H, s, 7-OCH$_3$), 2.60 (3H, s, 2'-NCH$_3$), 2.47 (3H, s, 2-NCH$_3$).

H-06 C$_{45}$H$_{46}$N$_3$O$_7$Cl; ESI-MS: m/z 776.32 [M+H]$^+$; $^1$H-NMR (CDCl$_3$, 400 MHz) δ (ppm): 12.30 (1H, s, CONH), 7.75 (1H, s, H-13), 7.32 (1H, dd, J=2.0, 8.4 Hz, H-14'), 7.23 (1H, dd, J=2.4, 8.0 Hz, H-13'), 6.62 (1H, s, H-10), 6.60 (1H, d, J=2.4 Hz, H-11'), 6.48 (1H, s, H-5'), 6.26 (1H, s, H-5), 6.15 (1H, dd, J=2.0, 8.4 Hz, H-10'), 5.89 (1H, s, H-8'), 4.04 (1H, d, J=9.2 Hz, H-1'), 3.96 (3H, s, 12-OCH$_3$), 3.82 (1H, dd, J=5.6, 11.2 Hz, H-1), 3.75 (3H, s, 6-OCH$_3$), 3.37 (3H, s, 6'-OCH$_3$), 3.09 (3H, s, 7-OCH$_3$), 2.61 (3H, s, 2'-NCH$_3$), 2.47 (3H, s, 2-NCH$_3$).

H-07 C$_{43}$H$_{51}$N$_3$O$_7$; ESI-MS: m/z 772.55 [M+H]$^+$; $^1$H-NMR (CDCl$_3$, 400 MHz) δ (ppm): 10.39 (1H, s, CONH), 7.82 (1H, s, H-13), 7.31 (1H, d, J=7.2 Hz, H-14'), 7.20 (1H, d, J=8.0 Hz, H-13'), 6.62 (1H, s, H-10), 6.61 (1H, s, H-11'), 6.47 (1H, s, H-5'), 6.32 (1H, s, H-5), 6.15 (1H, d, J=8.0 Hz, H-10'), 5.87 (1H, s, H-8'), 3.98 (1H, d, J=8.8 Hz, H-1'), 3.95 (3H, s, 12-OCH$_3$), 3.82 (1H, dd, J=5.2, 10.4 Hz, H-1), 3.75 (3H, s, 6-OCH$_3$), 3.36 (3H, s, 6'-OCH$_3$), 3.08 (3H, s, 7-OCH$_3$), 2.61 (3H, s, 2'-NCH$_3$), 2.41 (3H, s, 2-NCH$_3$).

H-08 C$_{43}$H$_{51}$N$_3$O$_8$; ESI-MS: m/z 738.38 [M+H]$^+$; $^1$H-NMR (CDCl$_3$, 400 MHz) δ (ppm): 11.93 (1H, s, CONH), 7.72 (1H, s, H-13), 7.30 (1H, dd, J=2.0, 8.4 Hz, H-14'), 7.21 (1H, dd, J=2.8, 8.4 Hz, H-13'), 6.60 (1H, dd, J=2.4, 8.4 Hz, H-11'), 6.52 (1H, s, H-10), 6.48 (1H, s, H-5'), 6.31 (1H, s, H-5), 6.15 (1H, dd, J=2.0, 8.4 Hz, H-10'), 5.90 (1H, s, H-8'), 3.97 (1H, s, H-1'), 3.94 (3H, s, 12-OCH$_3$), 3.92 (2H, m, CH$_2$), 3.83 (1H, m, H-1), 3.74 (3H, s, 6-OCH$_3$), 3.37 (3H, s, 6'-OCH$_3$), 3.11 (3H, s, 7-OCH$_3$), 2.61 (3H, s, 2'-NCH$_3$), 2.46 (3H, s, 2-NCH$_3$).

H-09 C$_{47}$H$_{49}$N$_3$O$_7$; ESI-MS: m/z 768.56 [M+H]$^+$; $^1$H-NMR (CDCl$_3$, 400 MHz) δ (ppm): 12.36 (1H, s, CONH), 8.11 (1H, s, H-13), 7.78 (1H, d, J=15.6 Hz, CH=CH), 7.30 (1H, dd, J=2.0, 8.4 Hz, H-14'), 7.23 (1H, dd, J=2.4, 8.0 Hz, H-13'), 6.61 (1H, s, H-10), 6.58 (1H, d, J=2.4, 8.4 Hz, H-11'), 6.51 (1H, s, CH=CH), 6.47 (1H, s, H-5'), 6.33 (1H, s, H-5), 6.13 (1H, dd, J=2.0, 8.4 Hz, H-10'), 5.89 (1H, s, H-8'), 4.06 (1H, d, J=8.8 Hz, H-1'), 3.98 (3H, s, 12-OCH$_3$), 3.80 (1H, m, H-1), 3.75 (3H, s, 6-OCH$_3$), 3.48 (3H, s, 6'-OCH$_3$), 3.09 (3H, s, 7-OCH$_3$), 2.60 (3H, s, 2'-NCH$_3$), 2.58 (3H, s, 2-NCH$_3$).

H-10 C$_{41}$H$_{45}$N$_3$O$_7$; ESI-MS: m/z 692.54 [M+H]$^+$; $^1$H-NMR (CDCl$_3$, 400 MHz) δ (ppm): 12.24 (1H, s, CONH), 8.05 (1H, s, H-13), 7.30 (1H, d, J=7.6 Hz, H-14'), 7.22 (1H, dd, J=2.4, 8.4 Hz, H-13'), 6.59 (1H, s, H-10), 6.56 (1H, s, H-11'), 6.47 (1H, s, H-5'), 6.31 (1H, s, H-5), 6.13 (1H, d, J=7.6 Hz, H-10'), 5.89 (1H, s, H-8'), 4.01 (1H, d, J=9.2 Hz, H-1'), 3.95 (3H, s, 12-OCH$_3$), 3.80 (1H, dd, J=5.2, 10.8 Hz, H-1), 3.74 (3H, s, 6-OCH$_3$), 3.36 (3H, s, 6'-OCH$_3$), 3.09 (3H, s, 7-OCH$_3$), 2.60 (3H, s, 2'-NCH$_3$), 2.51 (3H, s, 2-NCH$_3$).

H-11 C$_{43}$H$_{49}$N$_3$O$_7$; ESI-MS: m/z 720.5 [M+H]$^+$; $^1$H-NMR (CDCl$_3$, 400 MHz) δ (ppm): 11.88 (1H, s, CONH), 7.99 (1H, s, H-13), 7.29 (1H, dd, J=2.4, 8.0 Hz, H-14'), 7.21 (1H, dd, J=2.4, 8.4 Hz, H-13'), 6.59 (1H, d, J=2.4 Hz, H-11'), 6.57 (1H, s, H-10), 6.47 (1H, s, H-5'), 6.31 (1H, s, H-5), 6.12 (1H, dd, J=2.0, 8.4 Hz, H-10'), 5.88 (1H, s, H-8'), 3.99 (1H, d, J=9.2 Hz, H-1'), 3.96 (3H, s, 12-OCH$_3$), 3.80 (1H, dd, J=5.6, 11.2 Hz, H-1), 3.75 (3H, s, 6-OCH$_3$), 3.36 (3H, s, 6'-OCH$_3$), 3.10 (3H, s, 7-OCH$_3$), 2.60 (3H, s, 2'-NCH$_3$), 2.50 (3H, s, 2-NCH$_3$).

H-12 C$_{40}$H$_{45}$N$_3$O$_8$; ESI-MS: m/z 696.3 [M+H]$^+$; $^1$H-NMR (CDCl$_3$, 400 MHz) δ (ppm): 12.47 (1H, s, CONH), 7.88 (1H, s, H-13), 7.31 (1H, dd, J=2.0, 8.0 Hz, H-14'), 7.22 (1H, dd, J=2.4, 8.0 Hz, H-13'), 6.58 (1H, dd, J=2.4, 8.4 Hz, H-11'), 6.57 (1H, s, H-10), 6.47 (1H, s, H-5'), 6.31 (1H, s, H-5'), 6.14 (1H, dd, J=2.0, 8.4 Hz, H-10'), 5.89 (1H, s, H-8'), 3.98 (1H, s, H-1'), 3.95 (3H, s, 12-OCH$_3$), 3.81 (1H, dd, J=5.6, 11.2 Hz, H-1), 3.75 (3H, s, 6-OCH$_3$), 3.36 (3H, s, 6'-OCH$_3$), 3.10 (3H, s, 7-OCH$_3$), 2.60 (3H, s, 2'-NCH$_3$), 2.47 (3H, s, 2-NCH$_3$).

H-13 C$_{42}$H$_{47}$N$_3$O$_9$; ESI-MS: m/z 738.3 [M+H]$^+$; $^1$H-NMR (CDCl$_3$, 400 MHz) δ (ppm): 12.36 (1H, s, CONH), 7.86 (1H, s, H-13), 7.30 (1H, dd, J=2.0, 8.0 Hz, H-14'), 7.21 (1H, dd, J=2.8, 8.0 Hz, H-13'), 6.58 (1H, dd, J=2.8, 8.4 Hz, H-11'), 6.57 (1H, s, H-10), 6.47 (1H, s, H-5'), 6.31 (1H, s, H-5'), 6.13 (1H, dd, J=2.4, 8.8 Hz, H-10'), 5.89 (1H, s, H-8'), 3.98 (1H, m, H-1'), 3.93 (3H, s, 12-OCH$_3$), 3.79 (1H, m, H-1), 3.75 (3H, s, 6-OCH$_3$), 3.36 (3H, s, 6'-OCH$_3$), 3.10 (3H, s, 7-OCH$_3$), 2.60 (3H, s, 2'-NCH$_3$), 2.50 (3H, s, 2-NCH$_3$).

H-14 C$_{41}$H$_{45}$N$_3$O$_9$; ESI-MS: ink: 724.3 [M+H]$^+$; $^1$H-NMR (CDCl$_3$, 400 MHz) δ (ppm): 13.49 (1H, s, CONH), 7.90 (1H, s, H-13), 7.33 (1H, dd, J=2.0, 8.0 Hz, H-14'), 7.22 (1H, dd, J=2.8, 8.0 Hz, H-13'), 6.61 (1H, dd, J=2.8, 8.4 Hz, H-11'), 6.60 (1H, s, H-10), 6.49 (1H, s, H-5'), 6.32 (1H, s, H-5), 6.14 (1H, dd, J=2.0, 8.8 Hz, H-10'), 5.90 (1H, s, H-8'), 3.96 (3H, s, 12-OCH$_3$), 3.87 (1H, d, J=5.6, 11.2 Hz, H-1'), 3.75 (3H, s, 6-OCH$_3$), 3.37 (3H, s, 6'-OCH$_3$), 3.11 (3H, s, 7-OCH$_3$), 2.62 (3H, s, 2'-NCH$_3$), 2.49 (3H, s, 2-NCH$_3$).

H-15 C$_{43}$H$_{45}$N$_3$O$_8$; ESI-MS: m/z 732.5 [M+H]$^+$; $^1$H-NMR (CDCl$_3$, 400 MHz) δ (ppm): 12.44 (1H, s, CONH), 7.86 (1H, s, H-13), 7.31 (1H, dd, J=2.0, 8.0 Hz, H-14'), 7.22 (1H, dd, J=3.2, 8.4 Hz, H-13'), 6.64 (1H, d, J=2.8 Hz, H-11'), 6.62 (1H, s, H-10), 6.48 (1H, s, H-5'), 6.31 (1H, s, H-5), 6.14 (1H, dd, J=2.0, 8.4 Hz, H-10'), 5.90 (1H, 5, H-8'), 4.03 (1H, d, J=8.8 Hz, H-1'), 3.96 (3H, s, 12-OCH$_3$), 3.81 (1H, dd, J=5.6, 11.2 Hz, H-1), 3.75 (3H, s, 6-OCH$_3$), 3.37 (3H, s, 6'-OCH$_3$), 3.10 (3H, s, 7-OCH$_3$), 2.60 (3H, s, 2'-NCH$_3$), 2.54 (3H, s, 2-NCH$_3$).

H-16 $C_{43}H_{45}N_3O_7S$; ESI-MS: m/z 748.3 [M+H]$^+$; $^1$H-NMR (CDCl$_3$, 400 MHz) δ (ppm): 12.07 (1H, s, —CONH—), 7.68 (1H, s, H-13), 7.31 (1H, dd, J=2.0, 8.4 Hz, H-14'), 7.23 (1H, dd, J=3.2, 8.4 Hz, H-13'), 6.23 (1H, s, H-10), 6.30 (1H, d, J=2.4 Hz, H-11'), 6.48 (1H, s, H-5'), 6.28 (1H, s, H-5), 6.15 (1H, dd, J=2.0, 10.4 Hz, H-10'), 5.89 (1H, s, H-8'), 4.06 (1H, d, J=9.2 Hz, H-1'), 3.95 (3H, s, 12-OCH$_3$), 3.81 (1H, dd, J=5.6, 11.2 Hz, H-1), 3.73 (3H, s, 6-OCH$_3$), 3.38 (3H, s, 6'-OCH$_3$), 3.09 (3H, s, 7-OCH$_3$), 2.60 (3H, s, 2'-NCH$_3$), 2.54 (3H, s, 2-NCH$_3$).

H-17 $C_{39}H_{45}N_3O_8S$; ESI-MS: m/z 716.2 [M+H]$^+$; $^1$H-NMR (CDCl$_3$, 400 MHz) δ (ppm): 7.36 (1H, dd, J=2.4, 8.4 Hz, H-14'), 7.06 (1H, dd, J=2.4, 8.0 Hz, H-13'), 6.96 (1H, s, H-13), 6.88 (1H, dd, J=2.8, 8.4 Hz, H-11'), 6.80 (1H, s, H-10), 6.52 (1H, s, H-5'), 6.35 (1H, d, J=2.0 Hz, H-10'), 6.33 (1H, s, H-5), 5.93 (1H, s, H-8'), 3.96 (3H, s, 12-OCH$_3$), 3.85 (1H, m, H-1'), 3.75 (3H, s, 6-OCH$_3$), 3.36 (3H, s, 6'-OCH$_3$), 3.20 (3H, s, 7-OCH$_3$), 2.17 (3H, s, 2'-NCH$_3$), 2.07 (3H, s, 2-NCH$_3$).

H-18 $C_{44}H_{47}N_3O_8S$; ESI-MS: m/z 778.3 [M+H]$^+$; $^1$H-NMR (CDCl$_3$, 400 MHz) δ (ppm): 7.29 (1H, d, J=2.0 Hz, H-14'), 7.24 (1H, s, H-13), 7.17 (1H, dd, J=2.8, 8.0 Hz, H-13'), 6.55 (1H, dd, J=2.4, 8.4 Hz, H-11'), 6.46 (1H, s, H-10), 6.40 (1H, s, H-5'), 6.29 (1H, s, H-5), 6.12 (1H, dd, J=2.0, 8.8 Hz, H-10'), 5.84 (1H, s, H-8'), 3.93 (3H, s, 12-OCH$_3$), 3.85 (1H, d, J=10.0 Hz, H-1'), 3.78 (1H, dd, J=5.6, 11.2 Hz, H-1), 3.73 (3H, s, 6-OCH$_3$), 3.35 (3H, s, 6'-OCH$_3$), 3.07 (3H, s, 7-OCH$_3$), 2.58 (3H, s, 2'-NCH$_3$), 2.50 (3H, s, 2-NCH$_3$).

H-19 $C_{44}H_{46}N_4O_{10}S$; ESI-MS: m/z 823.2 [M+H]$^+$; $^1$H-NMR (CDCl$_3$, 400 MHz) δ (ppm): 7.30 (1H, d, J=2.0 Hz, H-14'), 7.28 (1H, s, H-13), 7.18 (1H, dd, J=2.8, 8.4 Hz, H-13'), 6.55 (1H, dd, J=2.8, 8.8 Hz, H-11'), 6.46 (1H, s, H-10), 6.39 (1H, s, H-5'), 6.30 (1H, s, H-5), 6.13 (1H, dd, J=2.0, 8.4 Hz, H-10'), 5.85 (1H, s, H-8'), 3.95 (3H, s, 12-OCH$_3$), 3.90 (1H, d, J=8.8 Hz, H-1'), 3.77 (1H, dd, J=5.6, 11.2 Hz, H-1), 3.73 (3H, s, 6-OCH$_3$), 3.35 (3H, s, 6'-OCH$_3$), 3.07 (3H, s, 7-OCH$_3$), 2.57 (3H, s, 2'-NCH$_3$), 2.54 (3H, s, 2-NCH$_3$).

H-20 $C_{45}H_{49}N_3O_8S$; ESI-MS: m/z 792.2 [M+H]$^+$; $^1$H-NMR (CDCl$_3$, 400 MHz) δ (ppm): 7.28 (1H, d, J=6.8 Hz, H-14'), 7.25 (1H, s, H-13), 7.15 (1H, d, J=8.0 Hz, H-13'), 6.55 (1H, dd, J=1.6, 8.0 Hz, H-11'), 6.46 (1H, s, H-10), 6.40 (1H, s, H-5'), 6.30 (1H, s, H-5), 6.12 (1H, d, J=7.6 Hz, H-10'), 5.84 (1H, s, H-8'), 3.93 (3H, s, 12-OCH$_3$), 3.84 (1H, d, J=9.2 Hz, H-1'), 3.79 (1H, dd, J=5.2, 11.2 Hz, H-1), 3.73 (3H, s, 6-OCH$_3$), 3.35 (3H, s, 6'-OCH$_3$), 3.07 (3H, s, 7-OCH$_3$), 2.59 (3H, s, 2'-NCH$_3$), 2.49 (3H, s, 2-NCH$_3$).

H-21 $C_{44}H_{46}N_4O_{10}S$; ESI-MS: m/z 823.2 [M+H]$^+$; $^1$H-NMR (CDCl$_3$, 400 MHz) δ (ppm): 7.25 (1H, d, J=2.0 Hz, H-14'), 7.16 (1H, dd, J=2.4, 8.0 Hz, H-13'), 6.90 (1H, s, H-13), 6.50 (1H, dd, J=2.4, 8.4 Hz, H-11'), 6.48 (1H, s, H-10), 6.44 (1H, s, H-5'), 6.36 (1H, s, H-5), 6.11 (1H, dd, J=1.6, 8.4 Hz, H-10'), 5.88 (1H, s, H-8'), 4.14 (1H, d, J=9.6 Hz, H-1'), 3.88 (1H, m, H-1), 3.79 (3H, s, 12-OCH$_3$), 3.77 (3H, s, 6-OCH$_3$), 3.38 (3H, s, 6'-OCH$_3$), 3.11 (3H, s, 7-OCH$_3$), 2.69 (3H, s, 2'-NCH$_3$), 2.58 (3H, s, 2-NCH$_3$).

H-22 $C_{44}H_{45}N_3O_8Cl_2S$; ESI-MS: m/z 846.2 [M+H]$^+$; $^1$H-NMR (CDCl$_3$, 400 MHz) δ (ppm): 7.27 (1H, dd, J=2.0, 8.0 Hz, H-14'), 7.16 (1H, dd, J=2.4, 8.0 Hz, H-13'), 6.84 (1H, s, H-13), 6.51 (1H, dd, J=2.8, 8.4 Hz, H-11'), 6.48 (1H, s, H-10), 6.45 (1H, s, H-5'), 6.33 (1H, s, H-5), 6.12 (1H, dd, J=2.0, 8.4 Hz, H-10'), 5.88 (1H, s, H-8'), 4.02 (1H, d, J=9.2 Hz, H-1'), 3.78 (3H, s, 12-OCH$_3$), 3.77 (1H, s, H-1), 3.75 (3H, s, 6-OCH$_3$), 3.38 (3H, s, 6'-OCH$_3$), 3.10 (3H, s, 7-OCH$_3$), 2.61 (3H, s, 2'-NCH$_3$), 2.58 (3H, s, 2-NCH$_3$).

H-23 $C_{45}H_{49}N_3O_8S$; ESI-MS: m/z 792.2 [M+H]$^+$; $^1$H-NMR (CDCl$_3$, 400 MHz) δ (ppm): 7.33-7.29 (7H, m, H-Ph, 13, 14'), 7.22 (1H, dd, J=2.4, 8.0 Hz, H-13'), 6.54 (1H, dd, J=2.8, 8.4 Hz, H-11'), 6.49 (1H, s, H-10), 6.46 (1H, s, H-5'), 6.24 (1H, s, H-5), 6.14 (1H, dd, J=2.0, 8.8 Hz, H-10'), 5.86 (1H, s, H-8'), 3.94 (3H, s, 12-OCH$_3$), 3.78 (2H, m, H-1', 1), 3.73 (3H, s, 6-OCH$_3$), 3.34 (3H, s, 6'-OCH$_3$), 3.08 (3H, s, 7-OCH$_3$), 2.58 (3H, s, 2'-NCH$_3$), 2.30 (3H, s, 2-NCH$_3$).

H-24 $C_{44}H_{46}N_3O_8ClS$; ESI-MS: m/z 812.2 [M+H]$^+$; $^1$H-NMR (CDCl$_3$, 400 MHz) δ (ppm): 7.29 (1H, dd, J=2.0, 8.4 Hz, H-14'), 7.24 (1H, s, H-13), 7.18 (1H, dd, J=2.4, 8.0 Hz, H-13'), 6.56 (1H, dd, J=2.8, 8.4 Hz, H-11'), 6.46 (1H, s, H-10), 6.41 (1H, s, H-5'), 6.30 (1H, s, H-5), 6.13 (1H, dd, J=2.0, 8.4 Hz, H-10'), 5.85 (1H, s, H-8'), 3.94 (3H, s, 12-OCH$_3$), 3.83 (2H, m, H-1', 1), 3.74 (3H, s, 6-OCH$_3$), 3.35 (3H, s, 6'-OCH$_3$), 3.08 (3H, s, 7-OCH$_3$), 2.58 (3H, s, 2'-NCH$_3$), 2.50 (3H, s, 2-NCH$_3$).

H-25 $C_{40}H_{48}N_4O_8S$; ESI-MS: m/z 745.3 [M+H]$^+$; $^1$H-NMR (CDCl$_3$, 400 MHz) δ (ppm): 7.28 (1H, dd, J=2.4, 8.0 Hz, H-14'), 7.18 (1H, dd, J=2.4, 8.0 Hz, H-13'), 6.61 (1H, dd, J=2.4, 8.0 Hz, H-11'), 6.50 (1H, s, H-13), 6.46 (1H, s, H-10), 6.31 (1H, s, H-5'), 6.29 (1H, s, H-5), 6.12 (1H, dd, J=2.0, 8.4 Hz, H-10'), 5.87 (1H, s, H-8'), 3.94 (1H, m, H-1'), 3.88 (3H, s, 12-OCH$_3$), 3.81 (1H, m, H-1), 3.74 (3H, s, 6-OCH$_3$), 3.35 (3H, s, 6'-OCH$_3$), 3.11 (3H, s, 7-OCH$_3$), 2.88 (6H, s, CH$_3$), 2.59 (3H, s, 2'-NCH$_3$), 2.42 (3H, s, 2-NCH$_3$).

H-26 $C_{43}H_{50}N_4O_8$; ESI-MS: m/z 716.3 [M+H]$^+$; $^1$H-NMR (CDCl$_3$, 400 MHz) δ (ppm): 10.19 (1H, s, —CONH—), 7.32 (1H, s, H-13), 7.29 (1H, dd, J=1.6, 8.0 Hz, H-14'), 7.21 (1H, dd, J=2.4, 8.0 Hz, H-13'), 6.59 (1H, s, H-10), 6.58 (1H, d, J=2.4 Hz, H-11'), 6.46 (1H, s, H-5'), 6.30 (1H, s, H-5), 6.12 (1H, dd, J=2.0, 8.4 Hz, H-10'), 5.87 (1H, s, H-8'), 3.98 (1H, d, J=9.2 Hz, H-1'), 3.93 (3H, s, 12-OCH$_3$), 3.74 (3H, s, 6-OCH$_3$), 3.35 (3H, s, 6'-OCH$_3$), 3.09 (3H, s, 7-OCH$_3$), 2.60 (3H, s, 2'-NCH$_3$), 2.43 (3H, s, 2-NCH$_3$).

Example 4

The Preparation of Benzyl Tetrandrine B Derivatives

Experiment procedure: To a 10 mL round flask were added anhydrous tetrandrine B (50 mg, 0.08 mmol), and then anhydrous DMF (2 mL) under Ar atmosphere, NaH (7 mg, 0.16 mmol, 55%). The mixture was stirred well before dropping BnBr (20 µL, 0.16 mmol). The reaction was kept for 8 h at room temperature. The reaction was completed with TLC detection and was stopped with saturated NH$_4$Cl solution, then the mixture was poured in ice-water. The aqueous layer was extracted thrice with chloroform., washed with saturated NaCl solution, dried over anhydrous MgSO$_4$, filtered and evaporated to dryness. Chloroform was recovered and the crude product was separated by column chromatography (silica gel 15 g, 200 to 300 mesh; chloroform:methanol=30:1) to give pure H-31 (15 mg, yield 21%).

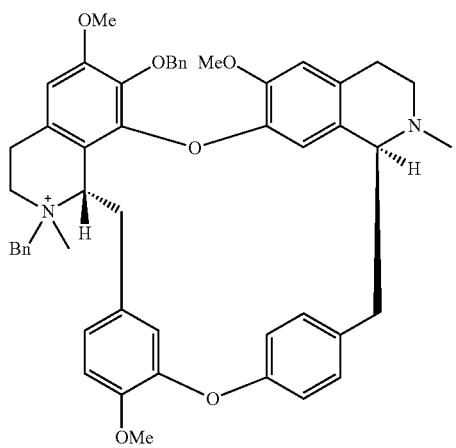 [SMILES: COc1ccc2cc1Oc1ccc(cc1)C[C@H]1c3cc(c(OC)cc3CCN1C)Oc1c(OCc3ccccc3)c(OC)cc3c1[C@H](C2)[N+](C)(Cc1ccccc1)CC3]

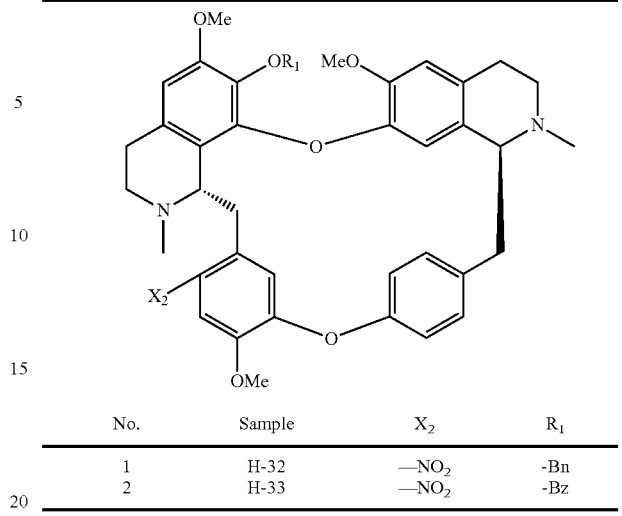

| No. | Sample | X₂ | R₁ |
|---|---|---|---|
| 1 | H-32 | —NO$_2$ | -Bn |
| 2 | H-33 | —NO$_2$ | -Bz |

Spectral Data

H-31 $C_{51}H_{53}N_2O_6$; ESI-MS: m/z 790.5 [M+H]$^+$; $^1$H-NMR (CDCl$_3$, 400 MHz) δ (ppm): 7.02 (1H, dd, J=2.4, 8.0 Hz, H-14'), 6.98 (1H, d, J=8.0 Hz, H-13'), 6.90 (1H, d, J=2.0 Hz, H-14), 6.88 (1H, d, J=4.0 Hz, H-13), 6.65 (1H, s, H-10), 6.55 (1H, dd, J=2.4, 8.0 Hz, H-11'), 6.53 (1H, s, H-5'), 6.48 (1H, dd, J=2.4, 8.0 Hz, H-10'), 6.33 (1H, s, H-5), 5.68 (1H, s, H-8'), 3.89 (3H, s, 12-OCH$_3$), 3.80 (3H, s, 6-OCH$_3$), 3.76 (1H, d, J=4.8 Hz, H-1'), 3.44 (3H, s, 6'-OCH$_3$), 2.83 (3H, s, 2'-NCH$_3$), 2.60 (3H, s, 2-NCH$_3$).

Example 5

The Preparation of Tetrandrine B Nitro-Derivatives

Experiment procedure: At 0° C. and Ar atmosphere, to a 10 mL round flask was added (CH$_3$CO)$_2$ (0.8 mL), then was dropped slowly concentrated nitric acid (0.5 mL) with stirring for 5 min and cooled to −10° C. To the mixed acid was dropped H-31 (50 mg, 0.07 mmol) in anhydrous chloroform (1 mL) for 10 min slowly. The reaction was completed for 1.5 h with TLC detection and was stopped by water, adjusted pH with stronger ammonia water, extracted with chloroform completely, washed with saturated NaCl solution, dried over anhydrous MgSO$_4$, filtered and evaporated to dryness. Chloroform was recovered to give solid product (48 mg), purified by column chromatography (chloroform:methanol:diethylamine=40:1:0.1) to give pure H-32 (46 mg, yield 92%).

In analogy with H-32, H-33 (yield 90%) was prepared, except that 7-tetrandrine B benzoylated was used instead of H-31.

Spectral Data

H-32 $C_{44}H_{45}N_3O_8$; ESI-MS: m/z 744.2 [M+H]$^+$; $^1$H-NMR (CDCl$_3$, 400 MHz) δ (ppm): 7.42 (1H, s, H-13), 7.37 (1H, dd, J=2.0, 8.0 Hz, H-14'), 7.13 (1H, dd, J=2.4, 8.0 Hz, H-13'), 6.75 (1H, dd, J=2.4, 8.0 Hz, H-11'), 6.52 (1H, s, H-10), 6.51 (1H, s, H-5'), 6.33 (1H, s, H-5), 6.29 (1H, dd, J=2.0, 8.4 Hz, H-10'), 5.85 (1H, s, H-8'), 3.99 (3H, s, 12-OCH$_3$), 3.81 (2H, m, H-1', 1), 3.72 (3H, s, 6-OCH$_3$), 3.38 (3H, s, 6'-OCH$_3$), 2.49 (3H, s, 2'-NCH$_3$), 2.22 (3H, s, 2-NCH$_3$).

H-33 $C_{44}H_{43}N_3O_9$; ELMS: m/z 757 [M]$^+$; $^1$H-NMR (CDCl$_3$, 400 MHz) δ (ppm): 7.42 (1H, s, H-13), 7.34 (1H, d, J=7.6 Hz, H-14'), 7.30 (1H, d, J=3.2 Hz, H-13'), 6.74 (1H, d, J=3.2 Hz, H-11'), 6.60 (1H, s, H-10), 6.46 (1H, s, H-5'), 6.40 (1H, s, H-5), 6.22 (1H, m, H-10'), 5.75 (1H, s, H-8'), 3.98 (3H, s, 12-OCH$_3$), 3.74 (1H, m, H-1'), 3.69 (3H, s, 6-OCH$_3$), 3.59 (1H, m, H-1), 3.53 (3H, s, 6'-OCH$_3$), 2.24 (3H, s, 2'-NCH$_3$), 1.91 (3H, s, 2-NCH$_3$).

Example 6

The Preparation of Tetrandrine B H-34 and H-35 Derivatives

Experiment procedure: a: To a 10 mL round flask were added anhydrous H-33 (100 mg, 0.13 mmol) and then AcOH (2.0 mL). H-33 was dissolved completely with stirring. To the mixture was added Fe powder (74 mg, 1.32 mmol) by three times, warmed to 60° C., detected by TLC. The reaction was kept for 5.5 h and was completed, cooled to room temperature. The mixture solution was poured in ice-water, adjusted pH to alkaline with saturated Na$_2$CO$_3$ solution, extracted with chloroform, washed with saturated NaCl solution, dried over anhydrous MgSO$_4$, filtered and evaporated to dryness. Chloroform was recovered to give solid product (79 mg), purified by column chromatography (chloroform:methanol:diethylamine=40:1:0.1) to give reduction product H-34 (60 mg, 65%) from H-33.

B: To a 10 mL round flask was added anhydrous H-34 (60 mg, 0.08 mmol), then was added pyridine (1.5 mL) at 0° C. and under Ar atmosphere. H-34 was dissolved completely with stirring. To the mixture was added chlorobenzeneformylchloride (16 μL, 0.12 mmol) with TLC detection. The reaction was kept for 4 h and was stopped. The mixture was poured in ice-water, adjusted pH to alkaline with saturated NaHCO$_3$ solution. The aqueous layer was extracted thrice with chloroform, washed with saturated NaCl solution, dried over anhydrous MgSO$_4$, filtered and evaporated to dryness. Chloroform was recovered to give solid product (58 mg), separated by column chromatography (chloroform:methanol:diethylamine=40:1:0.1) to obtain pure H-35 (35 mg, yield: 50%).

over anhydrous MgSO$_4$, filtered. Chloroform was recovered by reduced pressure to obtain crude product (102 mg), purified by column chromatography (chloroform:methanol:diethylamine=:1:0.1) to give pure reduction product H-36 (83 mg, yield 75%) from H-27.

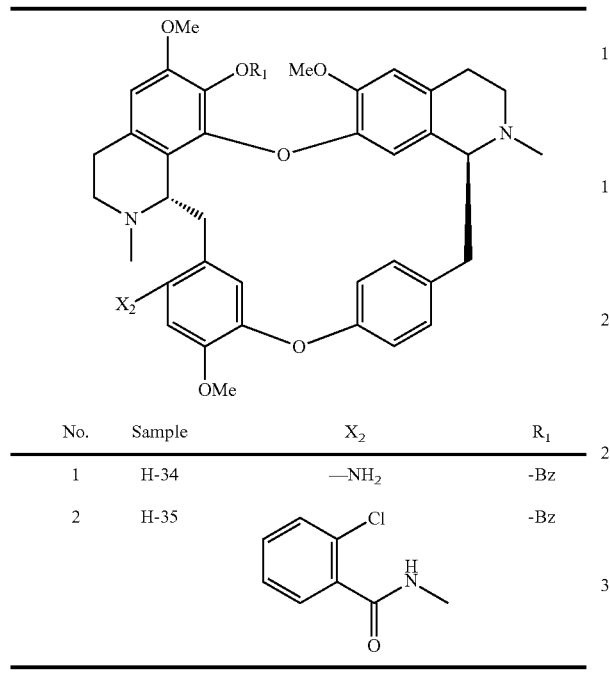

| No. | Sample | X$_2$ | R$_1$ |
|---|---|---|---|
| 1 | H-34 | —NH$_2$ | -Bz |
| 2 | H-35 | (2-Cl-C$_6$H$_4$-C(=O)-NH-) | -Bz |

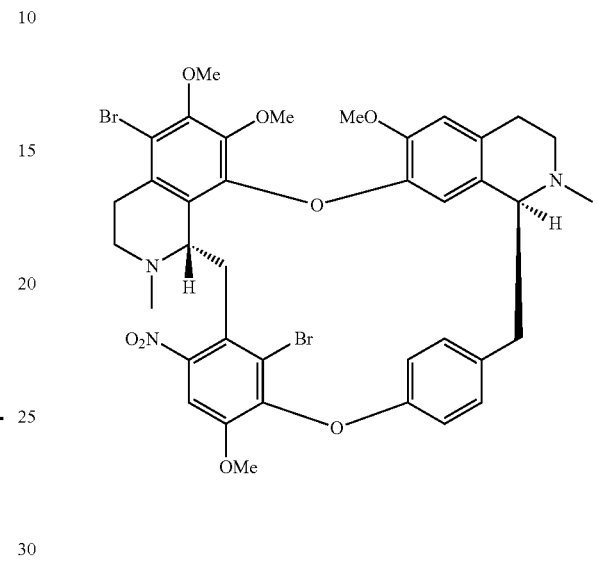

Spectral Data

H-34 C$_{44}$H$_{47}$N$_3$O$_7$; ESI-MS: m/z 727.8 [M+H]$^+$; $^1$H-NMR (CDCl$_3$, 400 MHz) δ (ppm): 7.37 (1H, d, J=8.0 Hz, H-14'), 7.24 (1H, s, H-13), 7.17 (1H, d, J=6.8 Hz, H-13'), 6.56 (1H, m, H-11'), 6.41 (1H, s, H-10), 6.34 (1H, s, H-5'), 6.31 (1H, s, H-5), 6.03 (1H, dd, J=8.0, 3.2 Hz, H-10'), 5.80 (1H, s, H-8'), 4.00 (3H, s, 12-OCH$_3$), 3.63 (3H, s, 6-OCH$_3$), 3.39 (3H, s, 6'-OCH$_3$), 2.22 (3H, s, 2'-NCH$_3$), 2.05 (3H, s, 2-NCH$_3$).

H-35 C$_{51}$H$_{48}$N$_3$O$_8$Cl; ESI-MS: m/z 866.4 [M+H]$^+$; $^1$H-NMR (CDCl$_3$, 400 MHz) δ (ppm): 12.77 (1H, s, —CONH—), 7.56-8.07 (5H, m, H-Bz), 7.37 (1H, d, J=8.0 Hz, H-14'), 7.24 (1H, s, H-13), 7.17 (1H, d, J=6.8 Hz, H-13'), 6.56 (1H, m, H-11'), 6.41 (1H, s, H-10), 6.34 (1H, s, H-5'), 6.31 (1H, s, H-5), 6.03 (1H, dd, J=2.0, 8.4 Hz, H-10'), 5.80 (1H, s, H-8'), 4.00 (3H, s, 12-OCH$_3$), 3.96-3.67 (3H, m, H-1', 1, 3b), 3.63 (3H, s, 6-OCH$_3$), 3.43 (1H, s, H-3'b), 3.39 (3H, s, 6'-OCH$_3$), 2.22 (3H, s, 2'-NCH$_3$), 2.14 (2H, m, H-15b, 4a), 2.05 (3H, s, 2-NCH$_3$).

Example 7

Nitro-Substituted Derivatives

Experiment procedure: To a 10 mL round flask were added anhydrous H-27 (100 mg, 0.15 mmol), and then trifluoroacetic acid (2.0 mL). H-27 was dissolved completely with stirring. To the mixture was added NBS (57 mg, 0.32 mmol) by twice in ice-bath, then kept for 30 min in ice-bath, warmed to room temperature. The reaction was kept for 4 h. The reaction mixture was poured in ice-water, adjusted pH=10 with saturated Na$_2$CO$_3$ solution, extracted with chloroform, washed with saturated NaCl solution, dried Spectral Data H-36 C$_{38}$H$_{39}$Br$_2$N$_3$O$_8$; ESI-MS: m/z 826.3 [M+H]$^+$; $^1$H-NMR (CDCl$_3$, 400 MHz) δ (ppm): 7.45 (1H, s, H-13), 7.43 (1H, dd, J=2.4, 8.4 Hz, H-14'), 7.17 (1H, dd, J=2.4, 8.4 Hz, H-13'), 6.78 (1H, dd, J=2.0, 8.0 Hz, H-11'), 6.51 (1H, s, H-5'), 6.32 (1H, dd, J=2.0, 8.4 Hz, H-10'), 6.13 (1H, s, H-8'), 4.00 (3H, s, 12-OCH$_3$), 3.63 (3H, s, 6-OCH$_3$), 3.39 (3H, s, 6'-OCH$_3$), 2.22 (3H, s, 2'-NCH$_3$), 2.05 (3H, s, 2-NCH$_3$).

Example 8

The Preparation of Compounds H-37, H-38 and H-39

To a 10 mL round flask were added anhydrous tetrandrine (100 mg, 0.15 mmol), anhydrous Na$_2$SO$_4$ (2.13 mg, 0.015 mmol), and then dichloromethane (2.0 mL). The sample was dissolved completely with stirring. To the mixture in ice-bath was dropped concentrated sulfuric acid (27 μL, 1.5 mmol) in 15 min. The reaction was kept for 1 h and warmed to room temperature, completed by 10 h. The reaction mixture was poured in ice-water, adjusted pH=10 with saturated Na$_2$CO$_3$ solution, extracted with chloroform, washed with saturated NaCl solution, dried over anhydrous MgSO$_4$, filtered. Chloroform was recovered by reduced pressure to obtain crude product (102 mg), purified by column chromatography (chloroform:methanol:diethylamine=50:1:0.1) to obtain H-37 (95 mg, yield 90%).

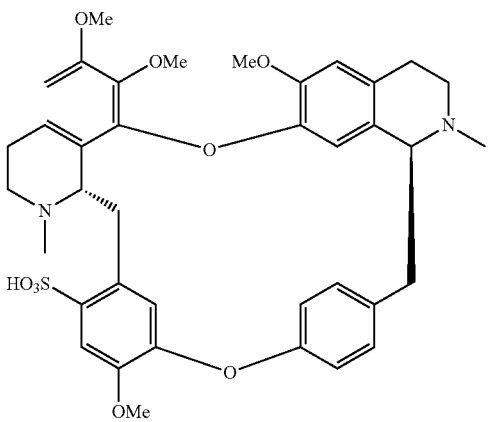 [SMILES: C=C(OC)/C(OC)=C1/Oc2cc3c(cc2OC)CCN(C)[C@H]3Cc2ccc(cc2)Oc2cc(c(S(=O)(=O)O)cc2OC)C[C@H]2C1=CCCN2C]

Spectral Data

H-37 $C_{38}H_{42}N_2O_9S$; ESI-MS: m/z 703.4 [M+H]$^+$; $^1$H-NMR (CDCl$_3$, 500 MHz) δ (ppm): 12.32 (1H, s, H—S), 7.81 (1H, s, H-13), 7.35 (1H, dd, J=1.6, 8.2 Hz, H-14'), 7.18 (1H, dd, J=2.5, 8.2 Hz, H-13'), 6.75 (1H, s, H-10), 6.68 (1H, dd, J=2.5, 8.4 Hz, H-11'), 6.52 (1H, s, H-5'), 6.43 (1H, s, H-5), 6.19 (1H, dd, J=1.7, 8.4 Hz, H-10'), 5.94 (1H, s, H-8'), 3.97 (3H, s, 12-OCH$_3$), 3.91 (1H, dd, J=5.9, 10.6 Hz, H-1'), 3.78 (3H, s, 6-OCH$_3$), 3.42 (1H, m, H-1), 3.38 (3H, s, 6'-OCH$_3$), 3.18 (3H, s, 7-OCH$_3$), 2.84 (3H, s, 2'-NCH$_3$), 2.65 (3H, s, 2-NCH$_3$).

To a 10 mL round flask were added anhydrous H-37 (100 mg, 0.15 mmol) and then dimethylformamide (2.0 mL). H-37 was dissolved completely with stirring. To the mixture in ice-bath was dropped thionyl chloride (11 μL, 1.5 mmol). Then the reaction was kept for 1 h, dropped aniline (14 mg) dissolved in dimethyl formamide (1 mL), warmed to 100° C., completed by 10 h. The reaction mixture was poured in ice-water, adjusted pH=7 with saturated NaHCO$_3$ solution, extracted with chloroform, washed with saturated NaCl solution, dried over anhydrous MgSO$_4$, filtered. Chloroform was recovered by reduced pressure to obtain crude product (102 mg), purified by column chromatography (chloroform:methanol:diethylamine=50:1:0.1) to give H-38 (87 mg, yield 75%).

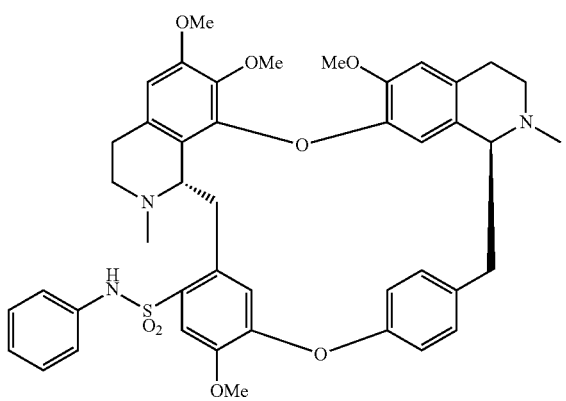 [SMILES: COc1cc(S(=O)(=O)Nc2ccccc2)c2cc1Oc1ccc(cc1)C[C@H]1c3cc(c(OC)cc3CCN1C)Oc1c(OC)c(OC)cc3c1[C@H](C2)N(C)CC3]

Spectral Data

H-38 $C_{44}H_{47}N_3O_8S$; ESI-MS: m/z 778.2 [M+H]$^+$; $^1$H-NMR (CDCl$_3$, 400 MHz) δ (ppm): 7.55 (2H, dd, J=2.2, 8.8 Hz, H-Ph), 7.35 (1H, dd, J=7.4, 14.8 Hz, H-Ph), 7.18 (2H, t, J=8.0, 15.2 Hz, H-Ph), 7.09 (1H, d, J=2.0 Hz, H-14'), 7.05 (1H, s, H-13), 7.01 (1H, dd, J=2.8, 8.0 Hz, H-13'), 6.55 (1H, dd, J=2.4, 8.4 Hz, H-11'), 6.46 (1H, s, H-10), 6.40 (1H, s, H-5'), 6.29 (1H, s, H-5), 6.12 (1H, dd, J=2.0, 8.8 Hz, H-10'), 5.84 (1H, s, H-8'), 3.93 (3H, s, 12-OCH$_3$), 3.85 (1H, d, J=10.0 Hz, H-1'), 3.78 (1H, dd, J=5.6, 11.2 Hz, H-1), 3.73 (3H, s, 6-OCH$_3$), 3.42 (1H, m, H-15'b), 3.35 (3H, s, 6'-OCH$_3$), 3.07 (3H, s, 7-OCH$_3$), =2.58 (3H, s, 2'-NCH$_3$), 2.50 (3H, s, 2-NCH$_3$).

In analogy with the preparation of H-38, H-39 (yield 81%) was prepared, except that methanol (9.0 μL) dissolved in dimethyl formamide was used instead of aniline (14 mg) dissolved in dimethyl formamide (1 mL)

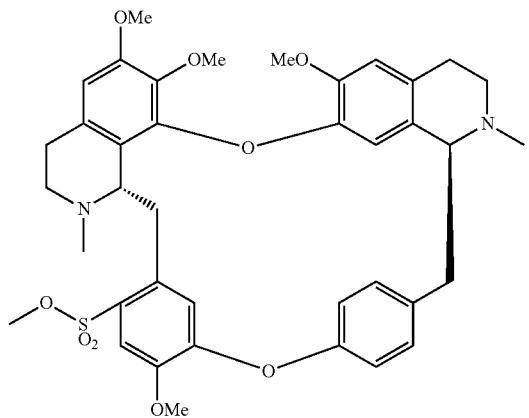

Spectral Data

H-39 $C_{39}H_{44}N_2O_9S$; ESI-MS: m/z 717.4 [M+H]$^+$; $^1$H-NMR (CDCl$_3$, 400 MHz) δ (ppm): 7.78 (1H, s, H-13), 7.50 (1H, dd, J=2.0, 8.4 Hz, H-14'), 7.25 (1H, dd, J=2.8, 8.4 Hz, H-13'), 6.75 (1H, dd, J=2.8, 8.4 Hz, H-11'), 6.66 (1H, s, H-10), 6.65 (1H, s, H-5'), 6.45 (1H, s, H-5), 6.24 (1H, dd, J=2.0, 8.4 Hz, H-10'), 6.02 (1H, s, H-8'), 4.00 (3H, s, 12-OCH$_3$), 3.82 (1H, dd, J=5.7, 10.6 Hz, H-1'), 3.79 (3H, s, 6-OCH$_3$), 3.48 (1H, m, H-1), 3.45 (3H, s, 14-SO$_2$—OCH$_3$), 3.20 (3H, s, 6'-OCH$_3$), 3.06 (3H, s, 7-OCH$_3$), 2.78 (3H, s, 2'-NCH$_3$), 2.57 (3H, s, 2-NCH$_3$).

Example 9

The Preparation of Compounds H-40, H-41, H-43 and H-44

In analogy with the preparation of H-36, H-40 and H-41 were prepared, except that H-37 was used instead of H-27.

In analogy with the preparation of H-36, H-43 and H-44 were prepared, except that N-chlorosuccinimide was used instead of NBS.

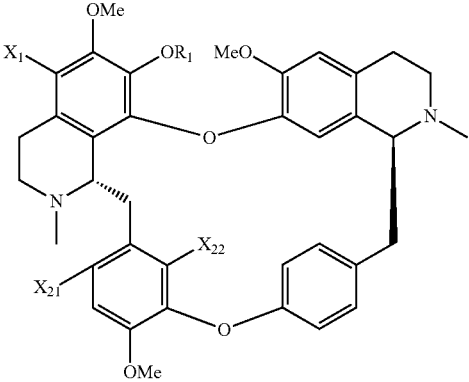

| No. | Sample | $X_1$ | $X_{21}$ | $X_{22}$ |
|---|---|---|---|---|
| 1 | H-40 | Br | —$SO_3H$ | H |
| 2 | H-41 | Br | —$SO_3H$ | Br |
| 3 | H-43 | Cl | —$NO_2$ | H |
| 4 | H-44 | Cl | —$NO_2$ | Cl |

Spectral Data:

H-40 $C_{38}H_{41}BrN_2O_9S$; ESI-MS: m/z 782.1 [M+H]$^+$; $^1$H-NMR (CDCl$_3$, 400 MHz) δ (ppm): 7.45 (1H, s, H-13), 7.43 (1H, dd, J=2.0, 8.4 Hz, H-14'), 7.11 (1H, dd, J=2.0, 8.4 Hz, H-13'), 6.86 (1H, s, H-10), 6.78 (1H, dd, J=2.0, 6.8 Hz, H-11'), 6.51 (1H, s, H-5'), 6.32 (1H, dd, J=1.6, 6.8 Hz, H-10'), 6.04 (1H, s, H-8'), 4.00 (3H, s, 12-OCH$_3$), 3.85 (1H, d, J=10.0 Hz, H-1'), 3.78 (1H, dd, J=2.4, 8.0 Hz, H-1), 3.71 (3H, s, 6-OCH$_3$), 3.45 (1H, m, H-15'b), 3.29 (3H, s, 6'-OCH$_3$), 3.28 (3H, s, 7-OCH$_3$), 2.64 (3H, s, 2'-NCH$_3$), 2.21 (3H, s, 2-NCH$_3$).

H-41 $C_{38}H_{40}Br_2N_2O_9S$; ESI-MS: m/z 860.2 [M+H]$^+$; $^1$H-NMR (CDCl$_3$, 400 MHz) δ (ppm): 7.36 (1H, s, H-13), 7.32 (1H, dd, J=2.0, 8.4 Hz, H-14'), 7.21 (1H, dd, J=2.0, 6.8 Hz, H-13'), 6.78 (1H, dd, J=1.6, 6.8 Hz, H-11'), 6.51 (1H, s, H-5'), 6.32 (1H, dd, J=2.4, 8.4 Hz, H-10'), 6.04 (1H, s, H-8'), 4.00 (3H, s, 12-OCH$_3$), 3.85 (1H, d, J=10.0 Hz, H-1'), 3.78 (1H, dd, J=5.6, 11.2 Hz, H-1), 3.71 (3H, s, 6-OCH$_3$), 3.45 (1H, m, H-15'b), 3.29 (3H, s, 6'-OCH$_3$), 3.28 (3H, s, 7-OCH$_3$), 2.65 (3H, s, 2'-NCH$_3$), 2.24 (3H, s, 2-NCH$_3$).

H-43 $C_{38}H_{40}ClN_3O_8$; ESI-MS: m/z 703.2 [M+H]$^+$; $^1$H-NMR (CDCl$_3$, 400 MHz) δ (ppm): 7.47 (1H, s, H-13), 7.41 (1H, dd, J=2.0, 8.0 Hz, H-14'), 7.35 (1H, dd, J=2.0, 8.0 Hz, H-13'), 7.02 (1H, s, H-10), 6.77 (1H, dd, J=1.6, 6.8 Hz, H-11'), 6.51 (1H, s, H-5'), 6.32 (1H, dd, J=1.6, 6.8 Hz, H-10'), 6.04 (1H, s, H-8'), 4.03 (3H, s, 12-OCH$_3$), 3.86 (1H, d, J=10.0 Hz, H-1'), 3.78 (1H, dd, J=5.6, 11.2 Hz, H-1), 3.71 (3H, s, 6-OCH$_3$), 3.45 (1H, m, H-15'b), 3.29 (3H, s, 6'-OCH$_3$), 3.28 (3H, s, 7-OCH$_3$), 2.64 (3H, s, 2'-NCH$_3$), 2.25 (3H, s, 2-NCH$_3$).

H-44 $C_{38}H_{39}Cl_2N_3O_8$; ESI-MS: m/z 737.2 [M+H]$^+$; $^1$H-NMR (CDCl$_3$, 400 MHz) δ (ppm): 7.47 (1H, s, H-13), 7.41 (1H, dd, J=2.0, 8.0 Hz, H-14'), 7.35 (1H, dd, J=2.0, 8.0 Hz, H-13'), 6.77 (1H, dd, J=1.6, 6.8 Hz, H-11'), 6.51 (1H, s, H-5'), 6.32 (1H, dd, J=1.6, 6.8 Hz, H-10'), 6.04 (1H, s, H-8'), 4.03 (3H, s, 12-OCH$_3$), 3.80 (1H, d, J=10.0 Hz, H-1'), 3.78 (1H, dd, J=5.6, 11.2 Hz, H-1), 3.54 (3H, s, 6-OCH$_3$), 3.45 (1H, m, H-15'b), 3.14 (3H, m, 6'-OCH$_3$), 2.62 (3H, s, 2'-NCH$_3$), 2.20 (3H, s, 2-NCH$_3$).

Example 10

The Preparation of H-42

At 0° C. and under Ar atmosphere, to a 10 mL round flask were added tetrandrine (50 mg) dissolved in dichloromethane (2 mL). The mixture was stirred for 5 min and cooled to −10° C., dropped concentrated nitric acid (0.6 mL) slowly in 15 min, detected by TLC. The reaction was completed for 13 h and was stopped by water, adjusted pH with stronger ammonia water, extracted with chloroform completely, washed with saturated NaCl solution, dried over anhydrous MgSO$_4$, filtered and evaporated to dryness. Chloroform was recovered to give solid product (610 mg), purified by column chromatography (chloroform:methanol=50:1) to give pure H-42 (33 mg, yield 65%).

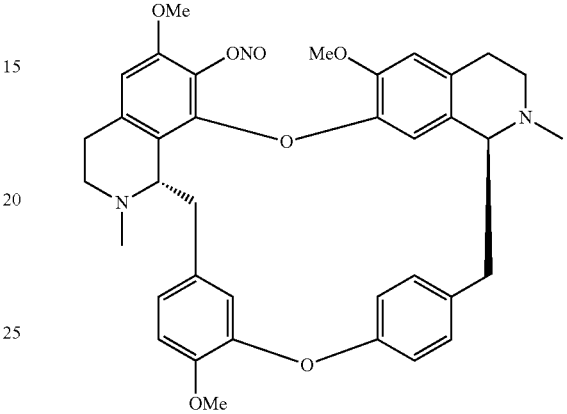

Spectral Data

H-42 $C_{37}H_{39}N_3O_7$; ESI-MS: m/z 638.1 [M+H]$^+$; $^1$H-NMR (CDCl$_3$, 400 MHz) δ (ppm): 7.40 (1H, dd, J=1.6, 6.4 Hz, H-14'), 7.23 (1H, dd, J=2.0, 6.4 Hz, H-13'), 6.86 (1H, s, H-14), 6.85 (1H, s, H-13), 6.76 (1H, s, H-10), 6.74 (1H, dd, J=2.0, 6.8 Hz, H-11'), 6.51 (1H, s, H-5'), 6.37 (1H, dd, J=1.2, 6.0 Hz, H-10'), 5.78 (1H, s, H-5), 5.42 (1H, s, H-8'), 3.93 (3H, s, 12-OCH$_3$), 3.80 (1H, d, J=10.0 Hz, H-1'), 3.78 (1H, dd, J=5.6, 11.2 Hz, H-1), 3.54 (3H, s, 6-OCH$_3$), 3.45 (1H, m, H-15'b), 3.14 (3H, m, 6'-OCH$_3$), 2.62 (3H, s, 2'-NCH$_3$), 2.20 (3H, s, 2-NCH$_3$).

Example 11

The Preparation of Compounds H-45 and H-52

1. To a 10 mL round flask were added anhydrous tetrandrine B (500 mg, 0.8 mmol), and anhydrous DMF (10 mL) under Ar atmosphere and then NaH (70 mg, 1.6 mmol, 55%). The mixture was stirred well, dropped benzoyl chloride (180 μL, 1.6 mmol), kept for 8 h at room temperature. With TLC detection, the reaction was completed and stopped with saturated NH$_4$Cl solution. The mixture solution was poured in ice-water and the aqueous layer was extracted thrice with chloroform, washed with saturated NaCl solution, dried over anhydrous MgSO$_4$, filtered and evaporated to dryness. Chloroform was recovered and the crude solid was separated by column chromatography (silica gel 15 g, 200 to 300 mesh; chloroform:methanol=30:1) to give pure product (512 mg).

2. To a 10 mL round flask were added anhydrous sample of step 1 (100 mg, 0.15 mmol), anhydrous Na$_2$SO$_4$ (2.2 mg, 0.015 mmol), and then dichloromethane (2.0 mL). The sample was dissolved completely with stirring. To the mixture in ice-bath was dropped concentrated sulfuric acid (27 μL, 1.5 mmol) in 15 min, kept for 1 h, warmed to room temperature, completed by 10 h. The mixture was poured in ice-water, adjusted pH=10 with saturated Na$_2$CO$_3$ solution, extracted with chloroform, washed with saturated NaCl solution, dried over anhydrous MgSO$_4$, filtered. Chloroform was recovered by reduced pressure to obtain crude product (102 mg), purified by column chromatography (chloroform:methanol:diethylamine=50:1:0.1) to give H-45 (95 mg, yield 80%).

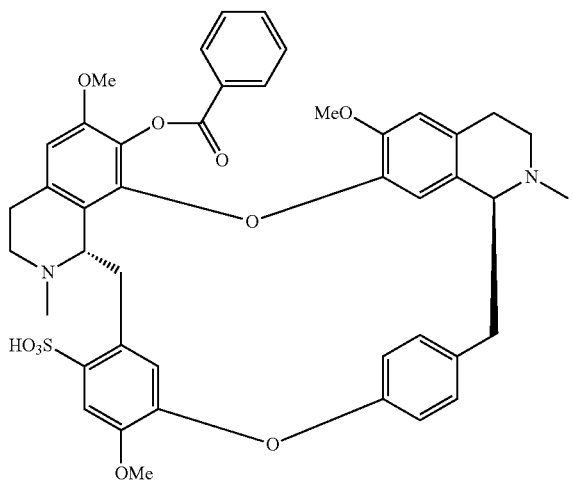 [SMILES: COc1cc(S(=O)(=O)O)c2cc1Oc1ccc(cc1)C[C@H]1c3cc(c(OC)cc3CCN1C)Oc1c(OC(=O)c3ccccc3)c(OC)cc3c1[C@H](C2)N(C)CC3]

Spectral Data

H-45 C$_{44}$H$_{44}$N$_2$O$_{10}$S; ESI-MS: m/z 744.2 [M+H]$^+$; $^1$H-NMR (CDCl$_3$, 400 MHz) δ (ppm): 12.32 (1H, s, 14-SO$_3$H), 7.47-7.78 (5H, m, H-Bz), 7.34 (2H, m, H-13', 14'), 7.10 (1H, s, H-13), 6.87 (1H, s, H-14), 6.77 (1H, m, H-11'), 6.60 (1H, s, H-10), 6.44 (1H, s, H-5'), 6.39 (1H, s, H-5), 6.24 (1H, m, H-10'), 5.57 (1H, s, H-8'), 3.92 (3H, s, 12-OCH$_3$), 3.69 (3H, s, 6-OCH$_3$), 3.55 (3H, m, H-1', 1, 4b), 3.48 (3H, s, 6'-OCH$_3$), 3.14 (3H, m, 6'-OCH$_3$), 2.62 (3H, s, 2'-NCH$_3$), 2.20 (3H, s, 2-NCH$_3$).

In analogy with the preparation of H-45, H-52 (yield 87%) was prepared, except that mixed acid was used instead of concentrated sulfuric acid and Na$_2$SO$_4$.

Spectral Data

H-52 C$_{44}$H$_{41}$N$_3$O$_9$; ESI-MS: m/z 758.1 [M+H]$^+$; $^1$H-NMR (CDCl$_3$, 400 MHz) δ (ppm): 7.41 (1H, s, H-13), 7.36 (1H, dd, J=2.0, 8.4 Hz, H-14'), 7.11 (1H, dd, J=2.4, 8.0 Hz, H-13'), 6.75 (1H, dd, J=2.8, 8.4 Hz, H-11'), 6.55 (1H, s, H-10), 6.49 (1H, s, H-5'), 6.35 (1H, s, H-5), 6.24 (1H, dd, J=1.6, 8.0 Hz, H-10'), 6.04 (1H, s, H-8'), 3.98 (3H, s, 12-OCH$_3$), 3.85 (1H, m, H-1'), 3.72 (3H, s, 6-OCH$_3$), 3.66 (1H, s, H-1), 3.42 (1H, m, H-15'b), 3.45 (3H, s, 6'-OCH$_3$), 3.11 (3H, s, 7-CH$_3$), 2.59 (3H, s, 2'-NCH$_3$), 2.32 (3H, s, 2'-NCH$_3$).

Example 12

The Preparation of Compounds H-46, H-47, H-48, H-49, H-50 and H-51

Experiment procedure: 1. To a 10 mL round flask were added anhydrous tetrandrine B (500 mg, 0.8 mmol), anhydrous DMF (10 mL) under Ar atmosphere, and then NaH (70 mg, 1.6 mmol, 55%). The mixture was stirred well, dropped benzoyl chloride (180 μL, 1.6 mmol), kept for 8 h at the room temperature. The reaction was stopped by saturated NH$_4$Cl with TLC detection. The mixture was poured in ice-water. The aqueous layer was extracted thrice with chloroform, washed with saturated NaCl solution, dried over anhydrous MgSO$_4$, filtered and evaporated to dryness. Chloroform was recovered and the crude product was separated by column chromatography (silica gel 15 g, 200 to 300 mesh; chloroform:methanol=30:1) to give pure sample (512 mg).

2. To a 10 mL round flask were added anhydrous sample of step 1 (100 mg, 0.15 mmol) and then trifluoro acetic acid (2.0 mL). The sample was dissolved completely with stirring. To the mixture in ice-bath was added N-chlorosuccinimide (25 mg) twice, kept for 30 min, warmed to room temperature, completed by 5 h. The reaction mixture was poured in ice-water, adjusted pH=7 with saturated NaHCO$_3$ solution, extracted with chloroform, washed with saturated NaCl solution, dried over anhydrous MgSO$_4$, filtered. Chloroform was recovered by reduced pressure to obtain crude product (93 mg), purified by column chromatography (chloroform:methanol:diethylamine=50:1:0.1) to give H-46 (56 mg, yield 51%).

| No. | Sample | X$_1$ | R$_1$ | X$_{21}$ | X$_{22}$ |
|---|---|---|---|---|---|
| 1 | H-46 | Cl | benzoyl | H | H |
| 2 | H-47 | Cl | benzoyl | Cl | H |
| 3 | H-48 | Br | isobutyryl | H | H |
| 4 | H-49 | Br | isobutyryl | Br | H |
| 5 | H-50 | Cl | isobutyryl | Cl | H |
| 6 | H-51 | Cl | isobutyryl | Cl | Cl |

Spectral Data

H-46 $C_{44}H_{43}ClN_2O_7$; ESI-MS: m/z 747.3 [M+H]$^+$; $^1$H-NMR (CDCl$_3$, 400 MHz) δ (ppm): 7.37-7.66 (5H, m, H-Bz), 7.34 (2H, m, H-13', 14'), 7.10 (1H, s, H-13), 7.06 (1H, s, H-14), 6.77 (1H, m, H-11'), 6.60 (1H, s, H-10), 6.44 (1H, s, H-5'), 6.39 (1H, s, H-5), 6.24 (1H, m, H-10'), 5.57 (1H, s, H-8'), 3.92 (3H, s, 12-OCH$_3$), 3.69 (3H, s, 6-OCH$_3$), 3.55 (3H, m, H-1', 1, 4b), 3.49 (3H, s, 6'-OCH$_3$), 3.17 (3H, s, 2'-NCH$_3$), 2.68 (2H, m, H-15b, 4a), 2.46 (3H, s, 2-NCH$_3$).

In analogy with the preparation of H-46, H-47 (yield 46%) was prepared, except that N-chlorosuccinimide (50 mg) was used instead of N-chlorosuccinimide (25 mg).

Spectral Data

H-47 $C_{44}H_{42}Cl_2N_2O_7$; ESI-MS: m/z 781.7 [M+H]$^+$; $^1$H-NMR (CDCl$_3$, 400 MHz) δ (ppm): 7.37-7.66 (5H, m, H-Bz), 7.34 (2H, m, H-13', H-14'), 7.10 (1H, s, H-13), 6.77 (1H, m, H-11'), 6.60 (1H, s, H-10), 6.44 (1H, s, H-5'), 6.39 (1H, s, H-5), 6.24 (1H, m, H-10'), 5.57 (1H, s, H-8'), 3.92 (3H, s, 12-OCH$_3$), 3.69 (3H, s, 6-OCH$_3$), 3.55 (3H, m, H-1', 1, 4b), 3.48 (3H, s, 6'-OCH$_3$), 3.20 (3H, s, 2'-NCH$_3$), 2.58 (2H, m, H-15b, 4a), 2.17 (3H, s, 2-NCH$_3$).

In analogy with the preparation of H-46, H-48 (yield 63%) was prepared, except that acetic anhydride was used instead of benzoyl chloride and NBS (32 mg) was used instead of N-chlorosuccinimide.

Spectral Data

H-48 $C_{39}H_{41}BrN_2O_7$; ESI-MS: m/z 729.7 [M+H]$^+$; $^1$H-NMR (CDCl$_3$, 400 MHz) δ (ppm): 7.35 (1H, dd, J=1.6, 6.4 Hz, H-14'), 7.14 (1H, dd, J=2.0, 6.4 Hz, H-13'), 6.86 (2H, m, H-13, H-14), 6.80 (1H, dd, J=2.0, 6.8 Hz, H-11'), 6.54 (1H, s, H-10), 6.45 (1H, s, H-5'), 6.28 (1H, dd, J=2.0, 6.8 Hz, H-10'), 5.95 (1H, s, H-8'), 3.93 (3H, s, 12-OCH$_3$), 3.82 (1H, m, H-1'), 3.28 (1H, dd, J=5.6, 11.2 Hz, H-1), 3.00 (3H, s, 6-OCH$_3$), 2.85 (1H, m, H-15'b), 2.73 (3H, m, 6'-OCH$_3$), 2.50 (3H, m, 2'-NCH$_3$), 2.15 (3H, s, 2-NCH$_3$).

In analogy with the preparation of H-46, H-49 (yield 49%) was prepared, except that acetic anhydride was used instead of benzoyl chloride and NBS (65 mg) was used instead of N-chlorosuccinimide (25 mg).

Spectral Data

H-49 $C_{39}H_{40}Br_2N_2O_7$; ESI-MS: m/z 808.6 [M+H]$^+$; $^1$H-NMR (CDCl$_3$, 400 MHz) δ (ppm): 7.36 (1H, dd, J=2.4, 8.4 Hz, H-14'), 7.08 (1H, m, H-13, H-14), 7.02 (1H, dd, J=2.8, 8.4 Hz, H-13'), 6.85 (1H, dd, J=2.8, 8.0 Hz, H-11'), 6.55 (1H, s, H-10), 6.53 (1H, s, H-5'), 6.32 (1H, dd, J=2.0, 8.4 Hz, H-10'), 5.93 (1H, s, H-8'), 3.85 (3H, s, 12-OCH$_3$), 3.50 (1H, m, H-1'), 3.15 (1H, d, J=3.2 Hz, H-1), 2.80 (3H, s, 6-OCH$_3$), 2.63 (1H, m, H-15'b), 2.48 (3H, m, 6'-OCH$_3$), 2.35 (3H, m, 2'-NCH$_3$), 2.11 (3H, s, 2-NCH$_3$).

In analogy with the preparation of H-46, H-50 (yield 41%) was prepared, except that acetic anhydride was used instead of benzoyl chloride and N-chlorosuccinimide (50 mg) was used instead of N-chlorosuccinimide (25 mg).

Spectral Data

H-50 $C_{39}H_{40}Cl_2N_2O_7$; ESI-MS: m/z 719.7 [M+H]$^+$; $^1$H-NMR (CDCl$_3$, 400 MHz) δ (ppm): 7.41 (1H, s, H-13), 7.36 (1H, dd, J=2.0, 6.4 Hz, H-14'), 7.12 (1H, dd, J=2.0, 6.4 Hz, H-13'), 6.75 (1H, dd, J=2.0, 6.8 Hz, H-11'), 6.55 (1H, s, H-10), 6.52 (1H, s, H-5'), 6.28 (1H, dd, J=2.0, 6.8 Hz, H-10'), 6.01 (1H, s, H-8'), 3.98 (3H, s, 12-OCH$_3$), 3.93 (1H, m, H-1'), 3.73 (3H, s, 6-OCH$_3$), 3.68 (1H, d, J=2.0 Hz, H-1), 3.45 (1H, m, H-15'b), 3.37 (3H, m, 6'-OCH$_3$), 3.19 (3H, m, 2'-NCH$_3$), 2.65 (3H, s, 2-NCH$_3$).

In analogy with the preparation of H-46, H-51 (yield 38%) was prepared, except that acetic anhydride was used instead of benzoyl chloride and N-chlorosuccinimide (80 mg) was used instead of N-chlorosuccinimide (25 mg).

Spectral Data

H-51 $C_{39}H_{39}Cl_3N_2O_7$; ESI-MS: m/z 754.1 [M+H]$^+$; $^1$H-NMR (CDCl$_3$, 400 MHz) δ (ppm): 7.43 (1H, s, H-13), 7.41 (1H, dd, J=2.0, 6.4 Hz, H-14'), 7.16 (1H, dd, J=2.0, 6.8 Hz, H-13'), 6.78 (1H, dd, J=2.0, 6.4 Hz, H-11'), 6.51 (1H, s, H-5'), 6.32 (1H, dd, J=1.6, 6.4 Hz, H-10'), 6.04 (1H, s, H-8'), 4.00 (3H, s, 12-OCH$_3$), 3.92 (1H, m, H-1'), 3.71 (3H, s, 6-OCH$_3$), 3.67 (1H, s, H-1), 3.42 (1H, m, H-15b), 3.27 (3H, m, 6'-OCH$_3$), 2.64 (3H, m, 2'-NCH$_3$), 2.21 (3H, s, 2-NCH$_3$).

Example 13

The Preparation of H-53

1. To a 10 mL round flask were added anhydrous tetrandrine B (500 mg, 0.8 mmol), anhydrous DMF (10 mL) under Ar atmosphere, and then NaH (70 mg, 1.6 mmol, 55%). The mixture was stirred well, dropped acetyl chloride (113 μL, 1.6 mmol), kept for 9 h at the room temperature, completed with TLC detection. The reaction was stopped with saturated NH$_4$Cl solution. The mixture solution was poured in ice-water. The aqueous layer was extracted thrice with chloroform., washed with saturated NaCl solution, dried over anhydrous MgSO$_4$, filtered and evaporated to dryness. Chloroform was recovered and the crude product was separated by column chromatography (silica gel 15 g, 200 to 300 mesh; chloroform:methanol=30:1) to give acetyl tetrandrine B (512 mg).

2. To a 10 mL round flask were added anhydrous acetyl tetrandrine B of step 1 (100 mg, 0.15 mmol), anhydrous Na$_2$SO$_4$ (2.13 mg, 0.015 mmol), and then dichloromethane (2.0 mL). The acetyl tetrandrine B was dissolved completely with stirring. To the mixture in ice-bath dropped concentrated sulfuric acid (27 μL, 1.5 mmol) in 15 min, kept for 1 h, warmed to room temperature, completed by 10 h. The reaction mixture was poured in ice-water, adjusted pH=10 with saturated Na$_2$CO$_3$ solution, extracted with chloroform, washed with saturated NaCl solution, dried over anhydrous MgSO$_4$, filtered. Chloroform was recovered by reduced pressure to obtain crude product (102 mg), purified by column chromatography (chloroform:methanol:diethylamine=50:1:0.1) to give H-53 (82 mg, 79% yield).

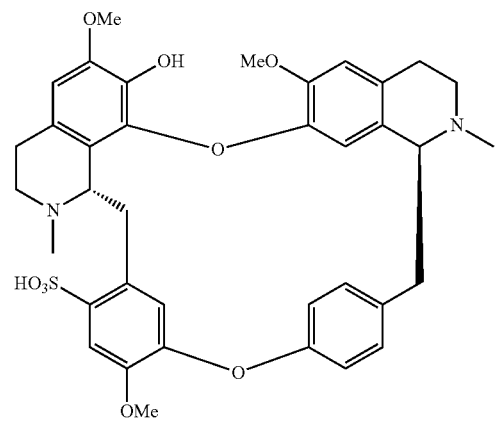

Spectral Data

H-53 $C_{37}H_{40}N_2O_9S$; ESI-MS: m/z 688.8 [M+H]$^+$; $^1$H-NMR (CDCl$_3$, 400 MHz) δ (ppm): 12.31 (1H, s, 14-SO$_3$H), 7.83 (1H, s, H-13), 7.32 (1H, dd, J=2.0, 8.4 Hz, H-14'), 7.11 (1H, dd, J=2.0, 8.0 Hz, H-13'), 6.77 (1H, s, H-10), 6.67 (1H, dd, J=2.8, 8.4 Hz, H-11'), 6.50 (1H, s, H-5'), 6.39 (1H, s, H-5), 6.24 (1H, dd, J=1.6, 6.8 Hz, H-10'), 5.97 (1H, s, H-8'), 3.98 (3H, s, 12-OCH$_3$), 3.90 (1H, m, H-1'), 3.81 (3H, s, 6-OCH$_3$), 3.36 (3H, s, 6'-OCH$_3$), 3.23 (1H, m, H-15'b), 2.79 (3H, s, 2'-NCH$_3$), 2.64 (3H, s, 2'-NCH$_3$).

Example 14

The Preparation of H-54

1. To a 10 mL round flask were added anhydrous tetrandrine (100 mg, 0.15 mmol), and then trifluoro acetic acid (2.0 mL). The tetrandrine was dissolved completely with stirring. To the mixture in ice-bath was added N-chlorosuccinimide (25 mg) twice, kept for 30 min, warmed to room-temperature, completed by 5 h. The reaction mixture was poured in ice-water, adjusted pH=7 with saturated NaHCO$_3$ solution, extracted with chloroform, washed with saturated NaCl solution, dried over anhydrous MgSO$_4$, filtered. Chloroform was recovered by reduced pressure to obtain crude product (93 mg), purified by column chromatography (chloroform:methanol:diethylamine=50:1:0.1) to give chlorotetrandrine (86 mg).

2. To a 10 mL round flask were added anhydrous chlorotetrandrine (50 mg, 0.08 mmol), and then trifluoro acetic acid (2.0 mL). The chlorotetrandrine was dissolved completely with stirring. To the mixture in ice-bath was added NBS (25 mg) twice, kept for 30 min, warmed to room temperature, completed by 5 h. The reaction mixture was poured in ice-water, adjusted pH=7 with saturated NaHCO$_3$ solution, extracted with chloroform, washed with saturated NaCl solution, dried over anhydrous MgSO$_4$, filtered. Chloroform was recovered by reduced pressure to obtain crude product (41 mg), purified by column chromatography (chloroform:methanol:diethylamine=50:1:0.1) to give H-54 (35 mg, yield 48%).

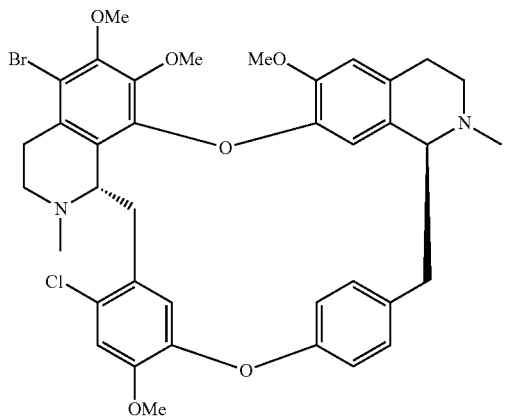 [SMILES: COc1cc(Cl)c2cc1Oc1ccc(cc1)C[C@H]1c3cc(c(OC)cc3CCN1C)Oc1c(OC)c(OC)c(Br)c3c1[C@H](C2)N(C)CC3]

Spectral Data

H-54 C$_{38}$H$_{40}$BrClN$_2$O$_6$; ESI-MS: m/z 736.1 [M+H]$^+$; $^1$H-NMR (CDCl$_3$, 400 MHz) δ (ppm): 7.38 (1H, dd, J=1.6, 8.0 Hz, H-14'), 7.16 (1H, dd, J=2.0, 6.8 Hz, H-13'), 7.08 (1H, s, H-13), 6.86 (1H, dd, J=2.4, 8.8 Hz, H-11'), 6.57 (1H, s, H-5'), 6.56 (1H, s, H-5'), 6.35 (1H, dd, J=1.6, 6.4 Hz, H-10'), 6.03 (1H, s, H-8'), 4.00 (3H, s, 12-OCH$_3$), 3.85 (1H, d, J=10.0 Hz, H-1'), 3.78 (1H, dd, J=5.6, 11.2 Hz, H-1), 3.71 (3H, s, 6-OCH$_3$), 3.45 (1H, m, H-15'b), 3.29 (3H, s, 6'-OCH$_3$), 3.28 (3H, s, 7-OCH$_3$), 2.64 (3H, s, 2'-NCH$_3$), 2.21 (3H, s, 2-NCH$_3$).

Example 15

The Preparation of H-55

1. To a 10 mL round flask were added tetrandrine (100 mg, 0.15 mmol), anhydrous Na$_2$SO$_4$ (2.13 mg, 0.015 mmol), and then dichloromethane (2.0 mL). The tetrandrine was dissolved completely with stirring. To the mixture in ice-bath was dropped concentrated sulfuric acid (27 μL, 1.5 mmol) in 15 min, kept for 1 h, warmed to room temperature, completed by 10 h. The reaction mixture was poured in ice-water, adjusted pH=10 with saturated Na$_2$CO$_3$ solution, extracted with chloroform, washed with saturated NaCl solution, dried over anhydrous MgSO$_4$, filtered. Chloroform was recovered by reduced pressure to obtain crude product (102 mg), purified by column chromatography (chloroform:methanol:diethylamine=50:1:0.1) to give H-37 (95 mg).

2. At 0° C. and under nitrogen atmosphere, to a 10 mL round flask was added (CH$_3$CO)$_2$O (0.15 mL), after that concentrated nitric acid (0.06 mL) were dropped slowly with stirring. The resultant mixture was slowly cooled to −10° C. after stirring for 5 min to obtain mixed acid. To the mixed acid was dropped slowly H-37 (50 mg, 0.08 mmol) in absolute chloroform (3 mL). The reaction was carried on for 70 min with TLC detection and was stopped by water. PH was adjusted with stronger ammonia water, extracted with chloroform completely, washed with saturated NaCl solution, dried over anhydrous MgSO$_4$, filtered and evaporated to dryness. Chloroform was recovered to give solid product (610 mg), purified by column chromatography (chloroform:methanol=50:1) to give pure H-55 (39 mg, yield 65%).

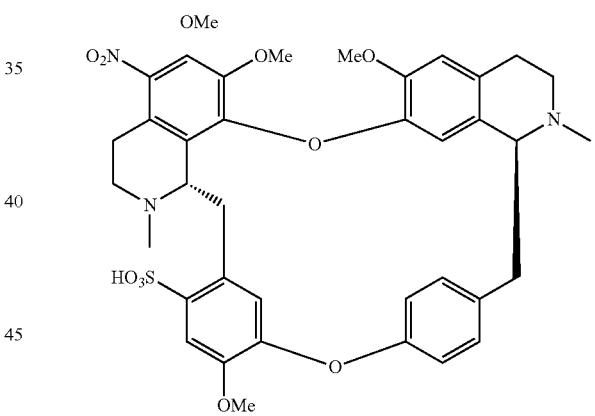

Spectral Data

H-55 C$_{38}$H$_{40}$N$_3$O$_{11}$S; ESI-MS: m/z 748.2 [M+H]$^+$; $^1$H-NMR (CDCl$_3$, 400 MHz) δ (ppm): 7.41 (1H, dd, J=2.0, 8.0 Hz, H-14'), 7.14 (1H, dd, J=2.0, 6.8 Hz, H-13'), 7.08 (1H, s, H-13), 6.86 (1H, dd, J=2.4, 8.8 Hz, H-11'), 6.57 (1H, s, H-5'), 6.56 (1H, s, H-5'), 6.35 (1H, dd, J=1.6, 6.4 Hz, H-10'), 6.03 (1H, s, H-8'), 4.00 (3H, s, 12-OCH$_3$), 3.92 (1H, d, J=10.0 Hz, H-1'), 3.78 (1H, dd, J=5.6, 11.2 Hz, H-1), 3.71 (3H, s, 6-OCH$_3$), 3.45 (1H, m, H-15'b), 3.29 (3H, s, 6'-OCH$_3$), 3.28 (3H, s, 7-OCH$_3$), 2.80 (3H, s, 2'-NCH$_3$), 2.17 (3H, s, 2-NCH$_3$).

Example 16

The Preparation of Hard Capsules

Compound H-32 (5 g), medicinal starch (75 g) and microcrystalline cellulose (20 g) were used. Firstly, the medicinal starch was dried, sieved (120 mesh), mixed with compound H-32 and microcrystalline cellulose, sieved (120 mesh) twice. The mixture was put in hard capsules to give 1000 hard capsules of the present invention. The compound H-32 (0.5 mg) was contained in every hard capsule.

Example 17

The Preparation of Coated Tablets

Compound H-28 (5 g), HPMC (6 g), sodium starch glycolate (10 g), microcrystalline cellulose (8 g), lactose (115 g), starch (50 g) and magnesium stearate (1 g) were used. The active matter and excipients were mixed well and then put in homogenizer, sprayed water appropriately, adjusted particle size, controlled water of 3-4%. The mixture was tabletted to 1000 tablets, then packed film.

Example 18

The Preparation of Solutions

Compound H-30 (5 g) was dissolved in polyethylene glycol 200 (400 mL), diluted with moderate amount of distilled water. To the mixture was added moderate amount of sucrose to adjust volume to 1000 mL, stirred well, filtered filled (10 mL per unit or 20 mL per unit), sterilized and packed.

Biology Example 1. human liver cancer cell strains BEL-7402 model discrimination
Tested compound: H-03
Tested methods: Sulforhodamine B (SRB)
Detecting Methods:
(1) Administration
According to growth rate of tumor cells, the adherent cells in logarithmic growth phase was implanted into a 96-well cell culture plate by 200 μL per well. Adhering for 24 h before dosing, each concentration was set with 3 holes. The corresponding concentration of saline as for control group and withering holes without cells. The tumor cells were cultured for 72 h under 5% $CO_2$ at 37° C.
(2) Stationary
The culture plate was takene out, 50 uL of trichloro acetic acid TCA fixed cells which were diluted to 50% (m/v) were added to each well. The plate was kept for 1 h at 4° C. If suspension cells are cultured, 50 uL cold TCA (80%) was added to each well. Final concentration of TCA is 16%, standed for 5 min, kept in a refrigerator for 1 h at 4° C.
(3) Washing
Stationary liquid was sucked out, washed by 5 times with distilled water, dried in the air.
(4) Staining
After drying in the air, 100 μL of SRB solution was added in each well, kept for 10-30 min at the room temperature.
(5) Washing
The supernatant was sucked out, washed by 5 times with acetic acid (1%), dried in the air.
(6) Dissolution
150 μL Tris solution was added in each well, vibrated for 5 min on the tablet oscillator.
(7) Measurement
OD values were measured with ELISA at 515 nm, zeroed with blank control.

(8) Calculation
Growth inhibition ratio of tumor cells was calculated according to the following formula:

Inhibition=$[(OD_{515control\ hole}-OD_{515dosing\ hole})/OD_{515control\ hole}] \times 100\%$.

According to inhibition ratio of different concentration, IC50 was determined with Logit method. Above experiment was repeated 2-3 times to give average $IC_{50}$ values as for final index.

Model principle: SRB is a kind of protein binding dye which can be binded with basic amino acid in biological macromolecules. OD values in specific wavelength range have linear relationship with cell number. According to OD values of binding substance, action effect of sample on tumor cell is defected.

Experiment result: When the concentration of example was is $1.0 \times 10^{-5}$ mol/L, inhibition ratio was 93.61%±0.68%. The tested compounds were shown inhibition to BEL-7402 cell.

Using above same method, inhibition effects of different compounds in the present application, tetrandrine, tetrandrine B and doxorubicin on BEL-7402 cell were measured. The results were shown in the table below.

| Sample | Density (mol/L) | BEL-7402/ Inhibition (%) |
|---|---|---|
| H-02 | $1.00 \times 10^{-5}$ | 81.43 ± 14.06 |
| H-03 | $1.00 \times 10^{-5}$ | 93.61 ± 0.68 |
| H-05 | $1.00 \times 10^{-5}$ | 92.14 ± 5.51 |
| H-06 | $1.00 \times 10^{-5}$ | 93.76 ± 1.96 |
| H-09 | $1.00 \times 10^{-5}$ | 90.72 ± 5.69 |
| H-10 | $1.00 \times 10^{-5}$ | 87.74 ± 0.63 |
| H-15 | $1.00 \times 10^{-5}$ | 87.23 ± 2.26 |
| H-16 | $1.00 \times 10^{-5}$ | 93.40 ± 4.70 |
| H-19 | $1.00 \times 10^{-5}$ | 92.70 ± 0.55 |
| H-20 | $1.00 \times 10^{-5}$ | 93.91 ± 0.40 |
| H-24 | $1.00 \times 10^{-5}$ | 90.01 ± 2.82 |
| H-26 | $1.00 \times 10^{-5}$ | 89.60 ± 2.01 |
| H-35 | $1.00 \times 10^{-5}$ | 86.88 ± 3.33 |
| Tetrandrine | $1.00 \times 10^{-5}$ | 53.87 ± 3.72 |
| Tetrandrine B | $1.00 \times 10^{-5}$ | 23.94 ± 3.65 |
| Doxorubicin | $1.00 \times 10^{-5}$ | 57.81 ± 4.05 |

2. human liver cancer cell strains PLC/PRF/5 model discrimination
Tested compound: H-03
Tested methods: Tetrazolium salt reduction method (MTT)
(1) Inoculating cells: A uniform cell suspension was prepared with culture solution containing fetal calf serum (10%). The suspension was implanted into a 96-well cell culture disc by 1000-10000 cells/200 μL per well.
(2) Culturing cells: The cells were cultured for 3-5 days according to known methods in the art (culturing time depending on experiment objective and requirement).
(3) Colour response: The cells were cultured for 3-5 days, 20 μl of MTT solution (5 mg/mL, PBS <pH=7.4>) was added in each well, incubated for 4 h. Culture was terminated and the culture suspension was carefully sucked out. As for suspension cells, they need be centrifuged before suspension solution in wells was sucked out. 150 μL of DMSO was added in each well, vibrated for 10 min. The crystal was fully dissolved.
(4) Colorimetry: Light absorbance values in each well were measured by ELISA at 490 nm and the results were recorded. The cell growth curve was drawn with time as the abscissa and absorbance values as vertical coordinates.
Model principle: Dehydrogenase related to NADP exists in mitochondria of living cell. Yellow MIT is reduced to insoluble blue-purple Formanzan. Dehydrogenase is disappeared in dead cell and MIT can not be reduced. According to reduction extent, action effect of sample on tumor cell is defected.

Experiment results: $IC_{50}$ value of compound H-03 on PLC/PRF/5 liver cancer cell strains is 12.1 μM. Inhibition rate of H-03 is much better than that of post-marketing sorafenib (PLC/PRF/5:$IC_{50}$=26.9 μM) and tetrandrine B.

Using above same method, inhibition effects of different compounds in the present application on PLC/PRF/5 cell were measured. The results were shown in the table below.

| Sample | PLC/PRF/5 $IC_{50}$ (μM) |
|---|---|
| H-01 | 12.3 |
| H-02 | 9.1 |
| H-03 | 12.1 |
| H-04 | 5.4 |
| H-05 | 9.5 |
| H-06 | 11.9 |
| H-07 | 5.3 |
| H-08 | 4.6 |
| H-09 | 9.8 |
| H-10 | 10.7 |
| H-11 | 7.6 |
| H-12 | 10.1 |
| H-13 | 10.1 |
| H-14 | 12.7 |
| H-15 | 2.5 |
| H-16 | 9.0 |
| H-17 | 4.6 |
| H-18 | 10.7 |
| H-19 | 11.6 |
| H-20 | 11 |
| H-21 | 10.8 |
| H-22 | 2.1 |
| H-23 | 10.9 |
| H-24 | 9.1 |
| H-25 | 13.2 |
| H-26 | 12.2 |
| H-27 | 2.9 |
| H-28 | 20.1 |
| H-29 | 14.8 |
| H-31 | 12.7 |
| H-32 | 8.9 |
| H-33 | 9.3 |
| H-34 | 7.8 |
| H-35 | 9.5 |
| H-36 | 11.9 |
| H-37 | 7.6 |
| H-38 | 10.2 |
| H-39 | 8.1 |
| H-40 | 10.5 |
| H-41 | 9.0 |
| H-42 | 3.4 |
| H-43 | 8.1 |
| H-44 | 4.1 |
| H-45 | 11.7 |
| H-46 | 3.5 |
| H-47 | 0.7 |
| H-48 | 0.5 |
| H-49 | 2.4 |
| H-50 | 9.8 |
| H-51 | 1.4 |
| H-52 | 6.7 |
| H-53 | 3.2 |
| H-54 | 3.2 |
| H-55 | 5.7 |
| Tetrandrine B | 16.9 |
| Sorafenib | 26.9 |

3. human liver cancer cell strains MHCC97L model discrimination

Tested compound: H-03

Tested methods: Tetrazolium salt reduction method (MTT)

(1) Inoculating cells: Inoculating cells: A uniform cell suspension was prepared with culture solution containing fetal calf serum (10%). The suspension was implanted into a 96-well cell culture disc by 1000-10000 cells/200 μL per well.

(2) Culturing cells: The cells were cultured for 3-5 days according to known methods in the art (culturing time depending on experiment objective and requirement).

(3) Colour response: The cells were cultured for 3-5 days, 20 μl of MTT solution (5 mg/mL, PBS <pH=7.4>) was added in each well, incubated for 4 h. Culture was terminated and the culture suspension was carefully sucked out. As for suspension cells, they need be centrifuged before suspension solution in wells was sucked out. 150 μL of DMSO was added in each well, vibrated for 10 min. The crystal was fully dissolved.

(4) Colorimetry: Light absorbance values in each well were measured by ELISA at 490 nm and the results were recorded. The cell growth curve was drawn with time as the abscissa and absorbance values as vertical coordinates.

Model principle: Dehydrogenase related to NADP exists in mitochondria of living cell. Yellow MTT is reduced to insoluble blue-purple Formanzan. Dehydrogenase is disappeared in dead cell and MTT can not be reduced. According to reduction extent, action effect of sample on tumor cell is defected.

Experiment results: $IC_{50}$ value of compound H-03 on MHCC97L liver cancer cell strains is 2.77 μM. Inhibition rate of H-03 is much better than that of post-marketing sorafenib (HCC $IC_{50}$=34.42 μM) and tetrandrine B.

Using above same method, inhibition effects of different compounds in the present application on HCC cell were measured. The results were shown in the table below.

| Sample | MHCC97L $IC_{50}$ (μM) |
|---|---|
| H-01 | 12.9 |
| H-02 | 7.8 |
| H-03 | 2.8 |
| H-04 | 12.2 |
| H-05 | 8.4 |
| H-06 | 10.3 |
| H-07 | 6.3 |
| H-08 | 1.4 |
| H-09 | 7.7 |
| H-10 | 10.4 |
| H-11 | 6.3 |
| H-12 | 9.1 |
| H-13 | 8.4 |
| H-14 | 7.9 |
| H-15 | 2.1 |
| H-16 | 11.9 |
| H-17 | 9.8 |
| H-18 | 9.1 |
| H-19 | 9.4 |
| H-20 | 12.5 |
| H-21 | 11.3 |
| H-22 | 5.6 |
| H-23 | 7.9 |
| H-24 | 8.2 |
| H-25 | 6.9 |
| H-26 | 10.8 |
| H-27 | 1.9 |
| H-28 | 8.1 |
| H-29 | 10.1 |
| H-30 | 10.7 |
| H-31 | 12.7 |
| H-32 | 1.26 |
| H-34 | 6.6 |
| H-35 | 8.2 |
| H-36 | 12.1 |
| H-37 | 7.3 |
| H-38 | 10.7 |
| H-39 | 9.9 |
| H-40 | 9.2 |

-continued

| Sample | MHCC97L IC$_{50}$ (μM) |
| --- | --- |
| H-41 | 8.6 |
| H-42 | 9.6 |
| H-43 | 8.8 |
| H-44 | 9.4 |
| H-45 | 8.9 |
| H-46 | 7.1 |
| H-47 | 7.9 |
| H-48 | 4.1 |
| H-49 | 8.7 |
| H-50 | 3.3 |
| H-51 | 10.4 |
| H-52 | 9.7 |
| H-53 | 1.1 |
| H-54 | 0.4 |
| H-55 | 3.1 |
| Tetrandrine B | 12.8 |
| Sorafenib | 34.4 |

From the foregoing it will be appreciated that, although specific embodiments of the present application have been described herein for purpose of illustration, various modifications or improvements may be made by a person having ordinary skill in the art without deviating from the spirit and scope of the present application. These modifications and improvements should fall within the scope of the appended claims in the present application.

The invention claimed is:

1. A compound of general formula (I), a single stereoisomer thereof, a mixture of stereoisomers thereof, and pharmaceutically acceptable salt thereof,

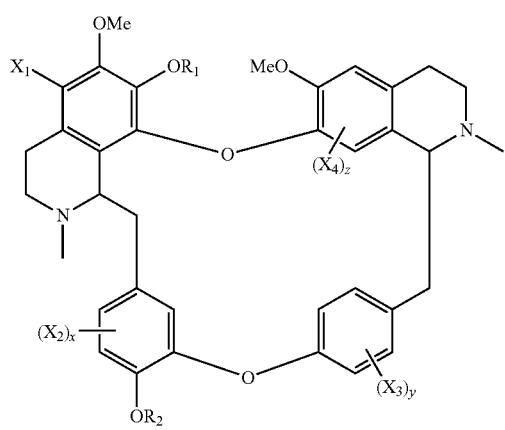

(I)

wherein,
$X_1$ is selected from hydrogen, halogen, nitro, nitroso, —SO$_3$H or optionally substituted sulfonyl;
$X_2$ is independently selected from hydrogen, halogen, nitro, nitroso, —SO$_3$H, optionally substituted amino or optionally substituted sulfonyl;
$X_3$ and $X_4$ are hydrogen;
said optionally substituted sulfonyl is selected from —SO$_3$H, sulfonyl substituted with arylamino, sulfonyl substituted with alkyl sulfonyl substituted with alkyl substituted with alkoxy or sulfonyl substituted with halogen;
said optionally substituted amino is selected from amino substituted with alkylcarbonyl, amino substituted with hydroxy substituted alkylcarbonyl, amino substituted with alkylcarbonyl, amino substituted with alkenylcarbonyl, amino substituted with alkynylcarbonyl, amino substituted with alkoxycarbonyl, amino substituted with aryl substituted alkoxycarbonyl, amino substituted with cycloalkylcarbonyl, amino substituted with arylcarbonyl, amino substituted with halogen substituted arylcarbonyl, amino substituted with alkoxy substituted arylcarbonyl, amino substituted with haloalkyl substituted arylcarbonyl, amino substituted with furylcarbonyl, amino substituted with thienylcarbonyl, amino substituted with morpholinylcarbonyl, amino substituted with aminocarbonyl, amino substituted with alkoxycarbonylcarbonyl, amino substituted with alkylsulfonyl, amino substituted with alkenylsulfonyl, amino substituted with alkynylsulfonyl, amino substituted with alkoxysulfonyl, amino substituted with arylsulfonyl, amino substituted with nitro substituted arylsulfonyl, amino substituted with alkyl substituted arylsulfonyl, amino substituted with halogen substituted arylsulfonyl, amino substituted with aminosulfonyl or arylalkylsulfonyl substituted amino;
$R_1$ is independently selected from hydrogen, nitroso, alkyl, alkyl substituted with aryl, alkenyl, alkynyl, aryl, arylcarbonyl, alkylcarbonyl, alkenylcarbonyl or alkynylcarbonyl;
$R_2$ is hydrogen;
x is 1, 2 or 3;
y is 1, 2, 3 or 4; and
z is 1 or 2;
provided that:
$X_1$, $X_2$, $X_3$ and $X_4$ are not hydrogen simultaneously; and
when one of $X_1$ and $X_2$ is halogen, the rest of $X_1$ and $X_2$ are independently selected from hydrogen, nitro, nitroso, —SO$_3$H, optionally substituted amino or optionally substituted sulfonyl, but they are not hydrogen simultaneously and $X_1$ is not optionally substituted amino.

2. A compound according to claim 1, wherein
$X_1$ is selected from hydrogen, halogen, nitro, nitroso or —SO$_3$H;
$X_2$ is independently selected from hydrogen, halogen, nitro, nitroso, amino or —SO$_3$H;
$R_1$ is independently selected from hydrogen, nitroso, alkyl, alkyl substituted with aryl, alkenyl, alkynyl, aryl, arylcarbonyl, alkylcarbonyl, alkenylcarbonyl or alkynylcarbonyl;
x is 1, 2 or 3;
y is 1, 2, 3 or 4; and
z is 1 or 2;
provided that:
$X_1$, $X_2$, $X_3$ and $X_4$ are not hydrogen simultaneously; and
when one of $X_1$ and $X_2$ is halogen, the rest of $X_1$ and $X_2$ are independently selected from hydrogen, nitro, nitroso, amino or —SO$_3$H, but they are not hydrogen simultaneously and $X_1$ is not amino.

3. A compound according to claim 1, wherein $X_1$ is selected from hydrogen, halogen, nitro, nitroso, —SO$_3$H, sulfonyl substituted with arylamino or sulfonyl substituted with alkyl; $X_2$ is independently selected from hydrogen, halogen, nitro, nitroso, —SO$_3$H, amino substituted with alkylcarbonyl, amino substituted with alkenylcarbonyl, amino substituted with alkynylcarbonyl, amino substituted with alkoxycarbonyl, amino substituted with cycloalkylcarbonyl, amino substituted with arylcarbonyl, amino substituted with aminocarbonyl, amino substituted with furylcarbonyl, amino substituted with thienylcarbonyl, amino substituted with alkoxycarbonylcarbonyl, amino substituted with alkylsulfonyl, amino substituted with alkenylsulfonyl, amino substituted with alkynylsulfonyl, amino substituted with alkoxysulfonyl, amino substituted with arylsulfonyl, amino substituted with aminosulfonyl, sulfonyl substituted with arylamino or sulfonyl substituted with alkyl.

4. A compound of claim 1, wherein $R_1$ is selected from hydrogen, nitroso, alkyl, aryl substituted alkyl, aryl, alkylcarbonyl or arylcarbonyl.

5. A compound of claim 1, wherein y is 4.

6. A compound of claim 1, wherein z is 2.

7. A compound of claim 1, wherein $X_1$ is hydrogen, nitro or halogen.

8. A compound according to claim 1, wherein $R_1$ is selected from hydrogen, nitroso, $C_1$-$C_6$ alkyl, phenylcarbonyl or $C_1$-$C_6$ alkylcarbonyl.

9. A compound according to claim 1, wherein $R_1$ is selected from hydrogen, methyl, benzyl, benzoyl, nitroso or acetyl.

10. A compound according to claim 1, wherein $R_1$ is selected from hydrogen, methyl, benzyl, benzoyl, nitroso or acetyl; and/or $X_1$ is hydrogen, nitro or halogen; and/or x is 1 or 2, and at least one $X_2$ is hydrogen, amino, nitro, nitroso, —$SO_3H$, Br, Cl, methylcarbonylamino, isobutylcarbonylamino, ethenylcarbonylamino, styrylcarbonylamino, 2-methylpropenylcarbonylamino, 2-methylpropoxycarbonylamino, hydroxymethylcarbonylamino, methylcarbonyloxymethylcarbonylamino, methoxycarbonylcarbonylamino, furylcarbonylamino, thienylcarbonylamino, morpholinylcarbonylamino, phenylcarbonylamino, chlorophenylcarbonylamino, methoxyphenylcarbonylamino, trifluoromethylphenylcarbonylamino, phenylmethoxycarbonylamino, methylsulfonylamino, phenylsulfonylamino, nitrophenylsulfonylamino, methylphenylsulfonylamino, chlorophenylsulfonylamino, dichlorophenylsulfonylamino, phenylmethylsulfonylamino, dimethylaminosulfonylamino, phenylaminosulfonyl or methoxymethylsulfonyl; and/or y is 3; and/or z is 2, provided that:

$X_1$, $X_2$, $X_3$ and $X_4$ are not hydrogen simultaneously, and when one of $X_1$ and $X_2$ is halogen, the rest of $X_1$ and $X_2$ are not hydrogen simultaneously.

11. A compound selected from:

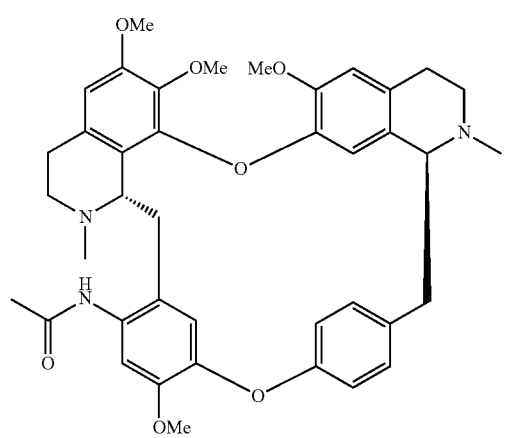

H-01

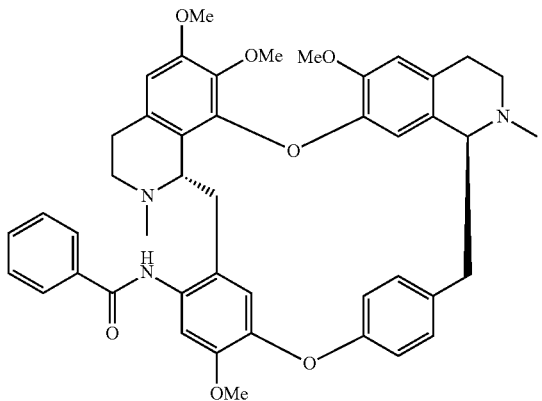

H-02

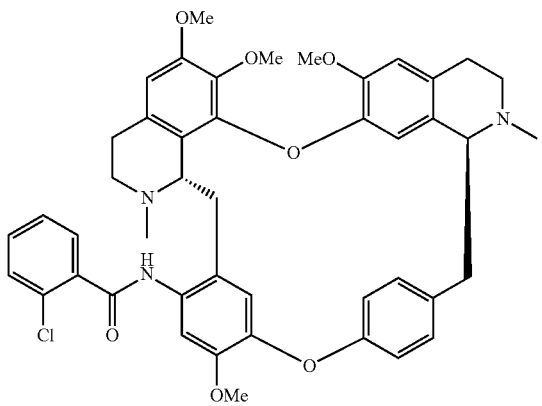

H-03

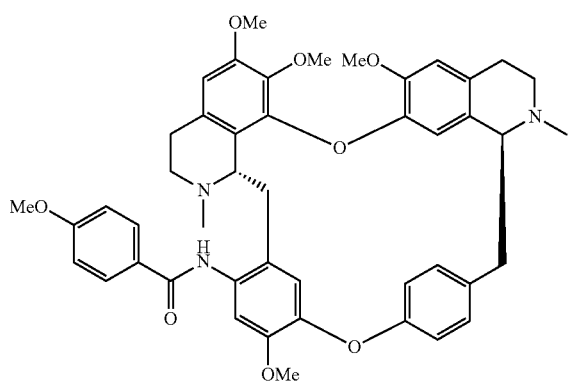

H-04

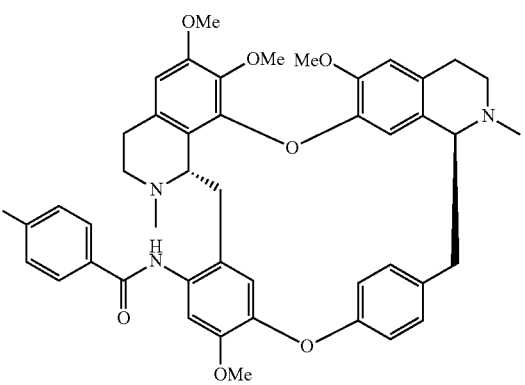

H-05

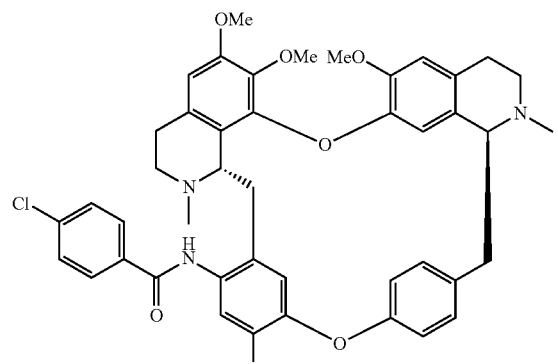
H-06
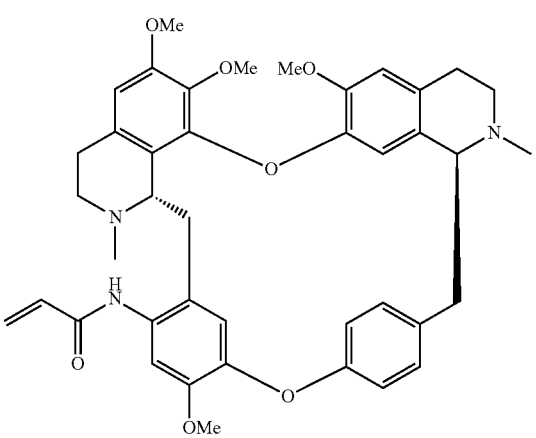
H-10
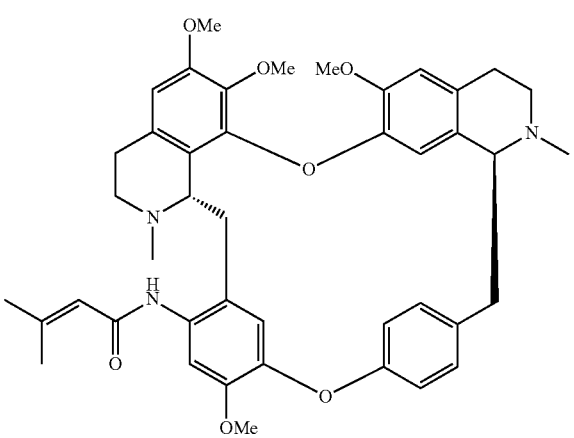
H-11
H-07
H-08
H-09
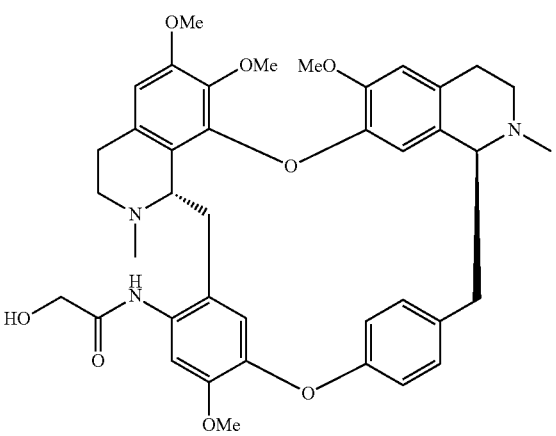
H-12

-continued
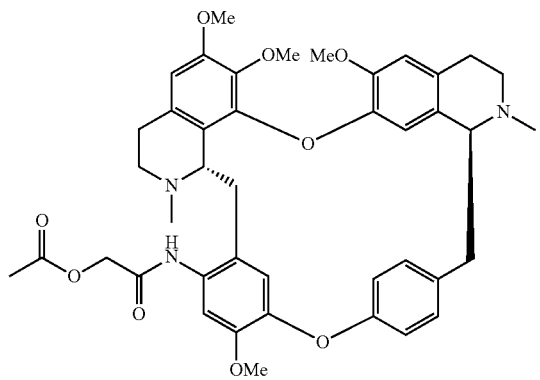
H-13
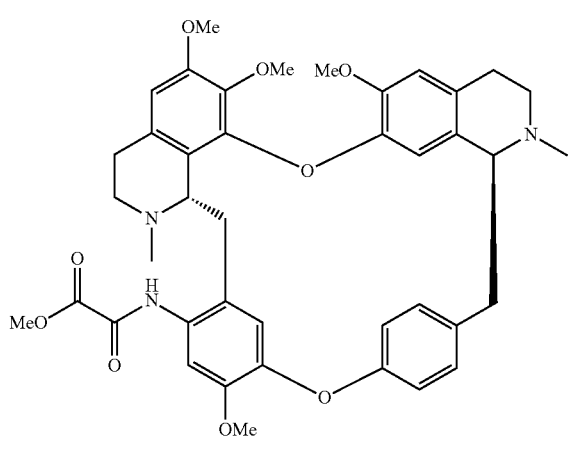
H-14
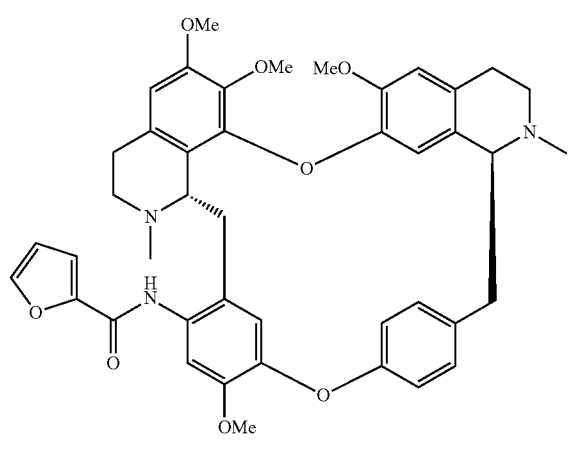
H-15
-continued
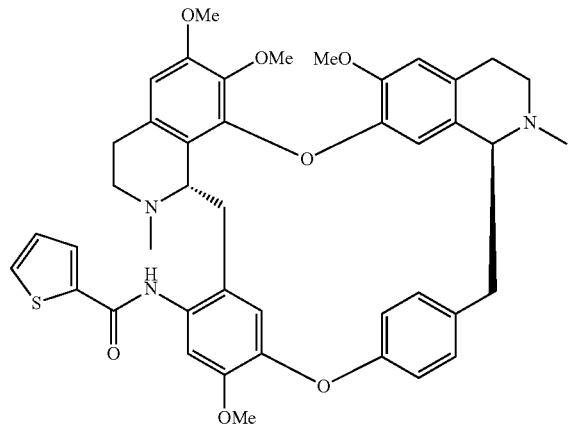
H-16
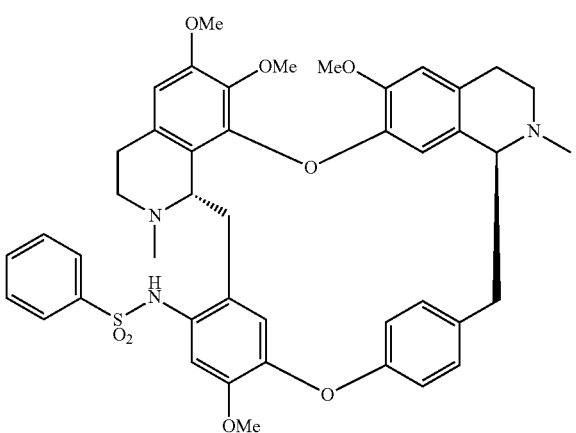
H-17
H-18

-continued
H-19
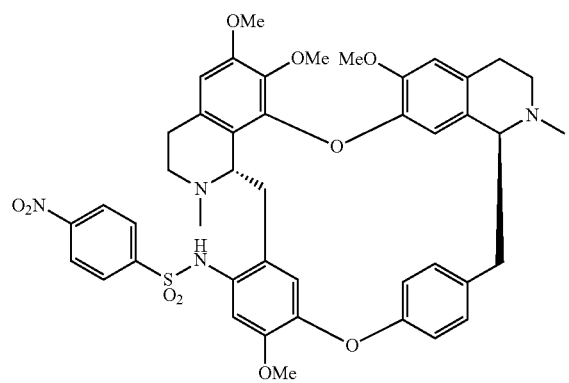
H-20
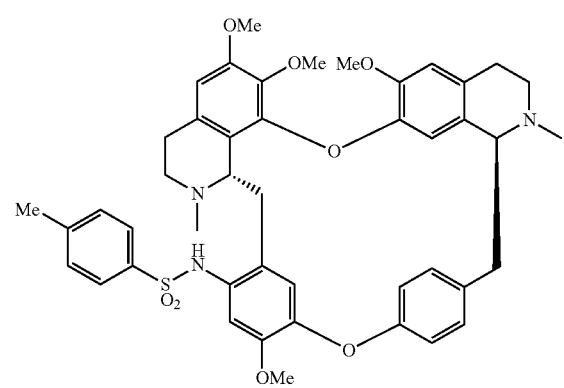
H-21
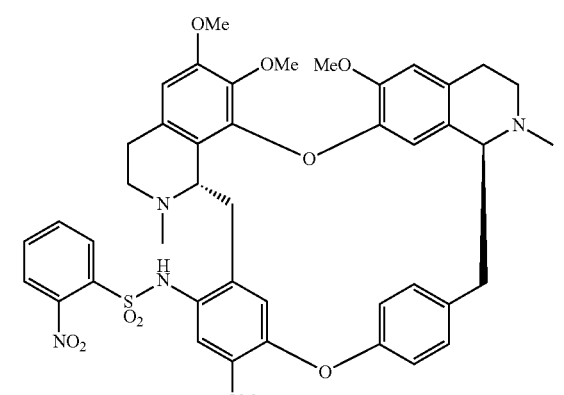
H-22
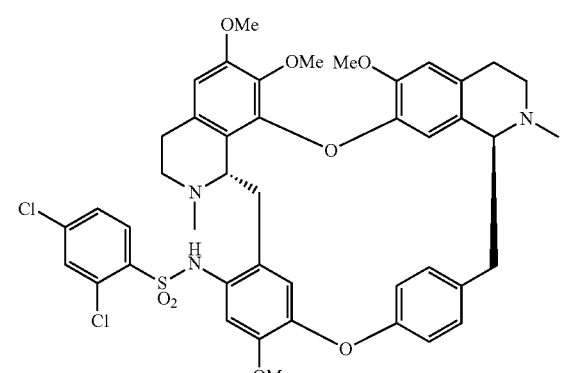
-continued
H-23
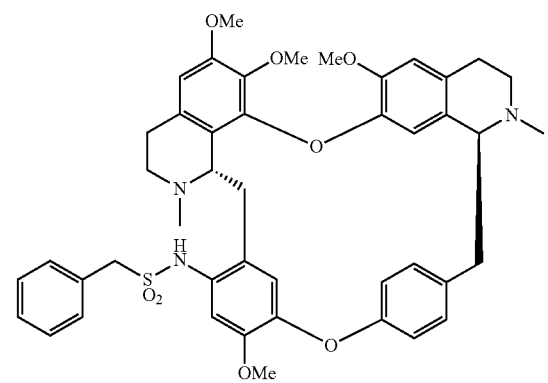
H-24
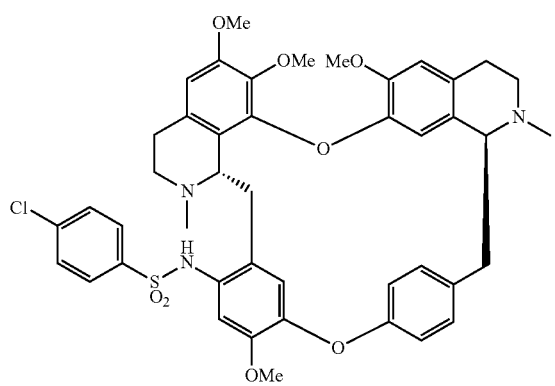
H-25
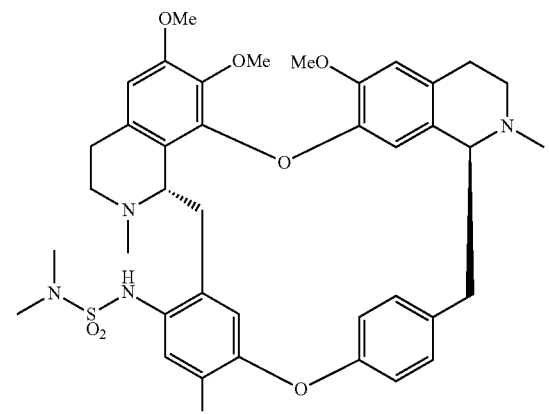

H-26
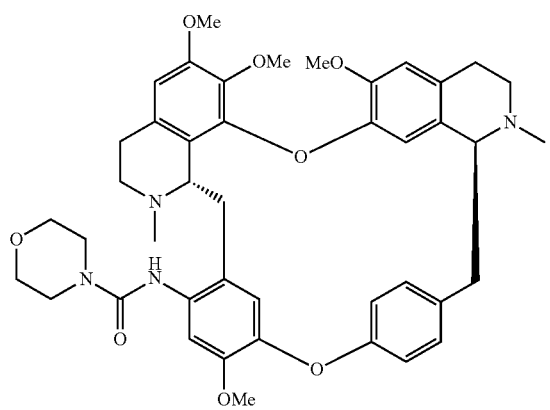
H-29
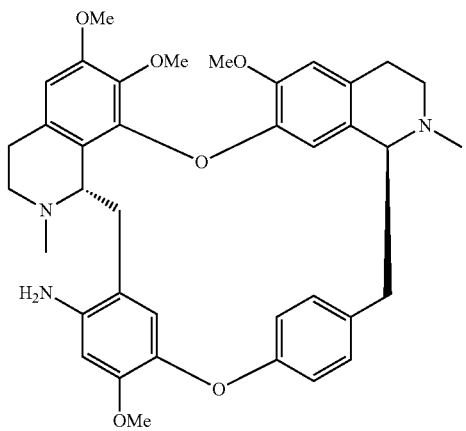
H-27
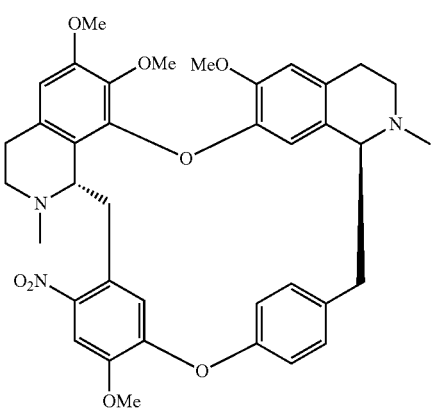
H-30
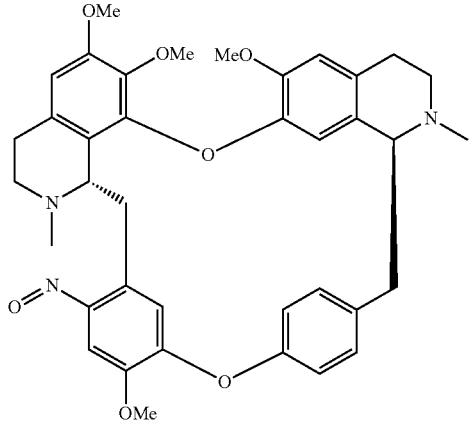
H-28
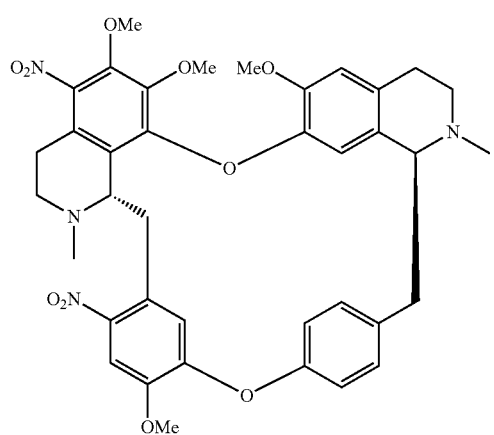
H-31
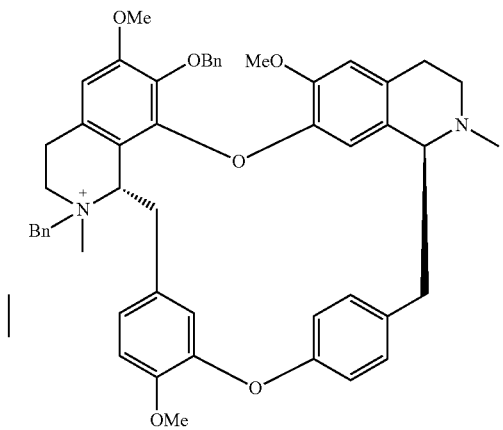

105
-continued
H-32
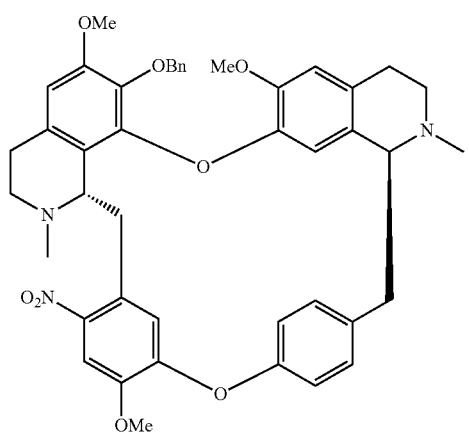
H-33
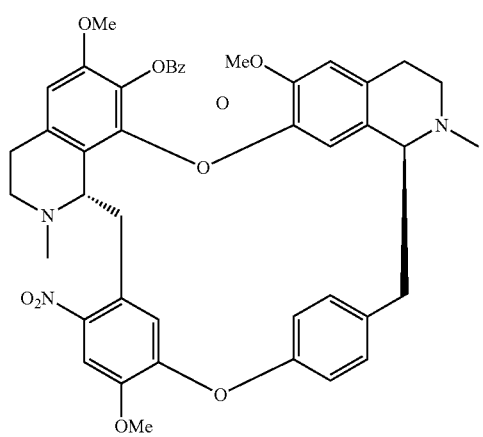
H-34
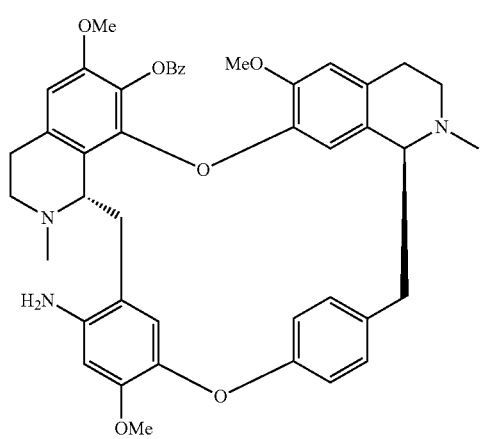
106
-continued
H-35
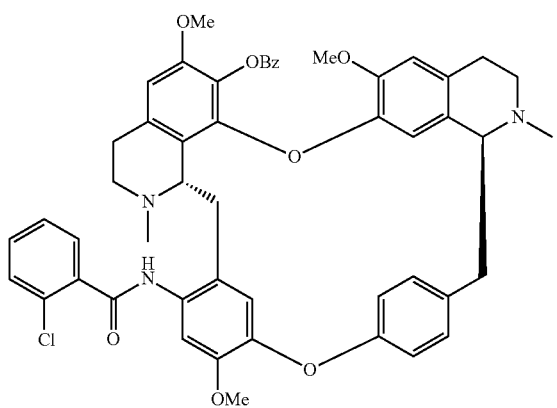
H-37
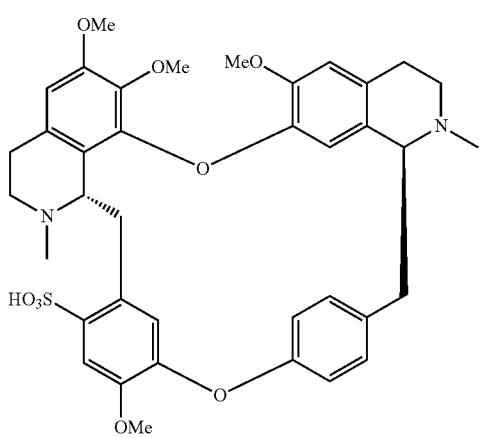
H-38
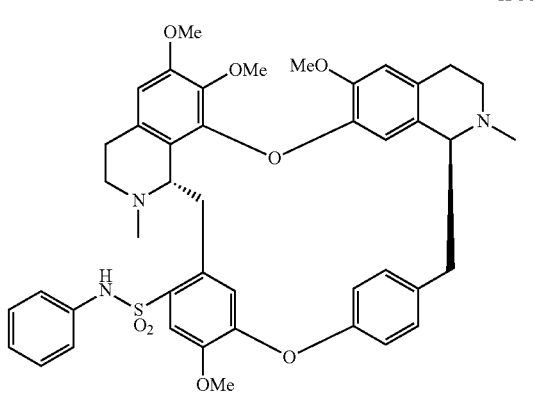

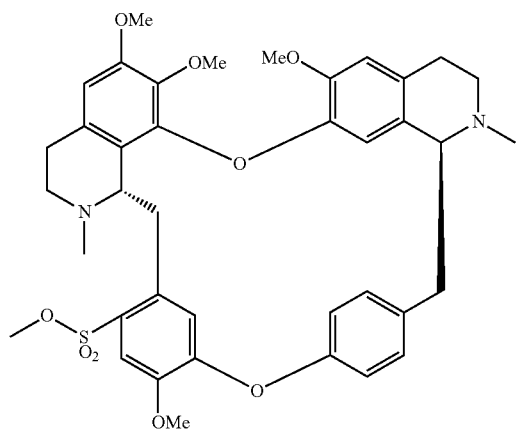
H-39
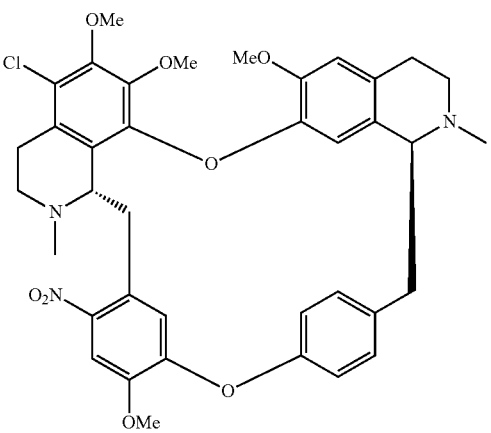
H-43
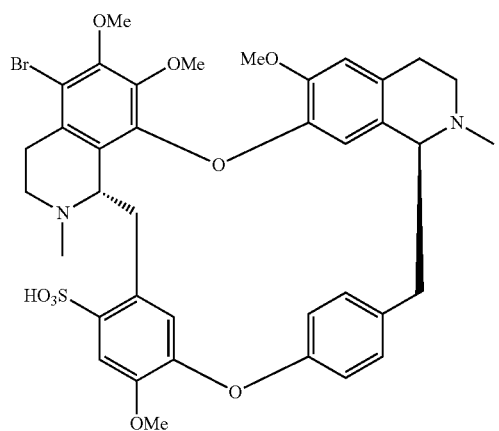
H-40
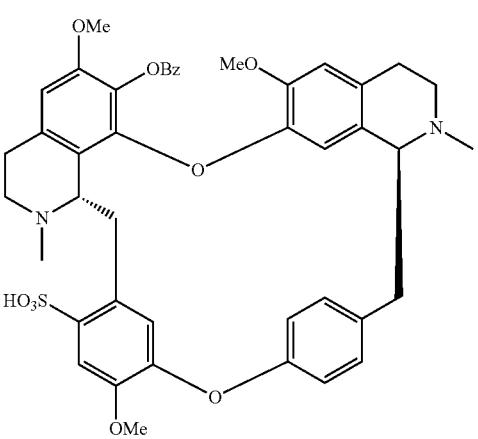
H-45
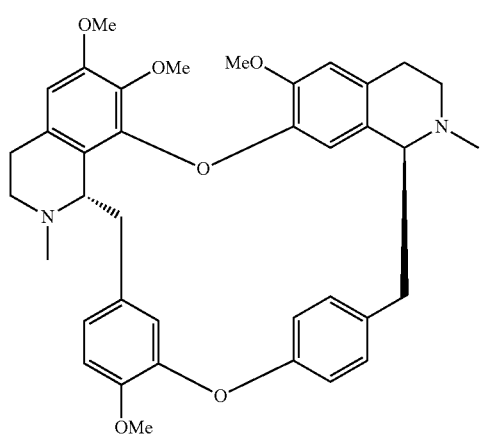
H-42
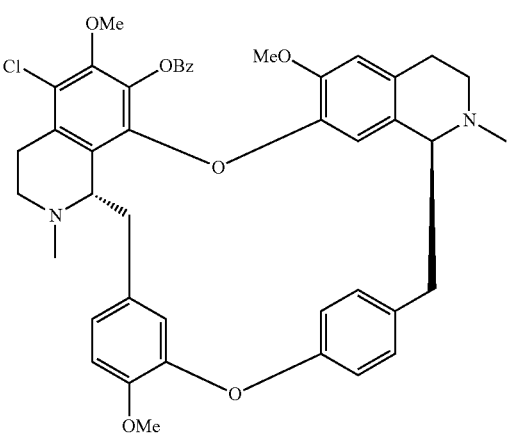
H-46

H-48

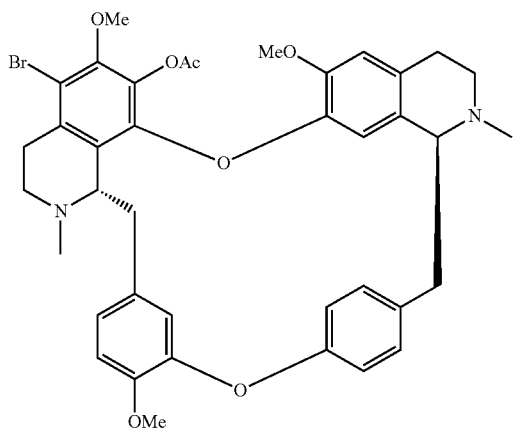

H-52

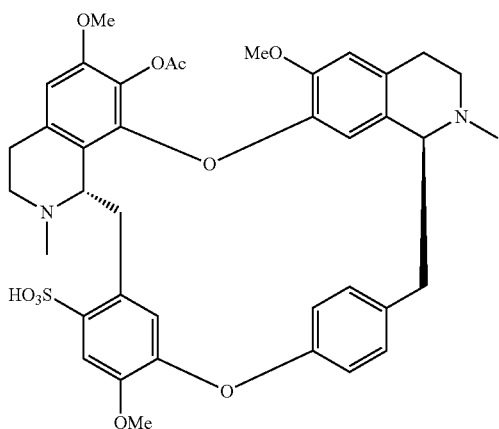

H-53

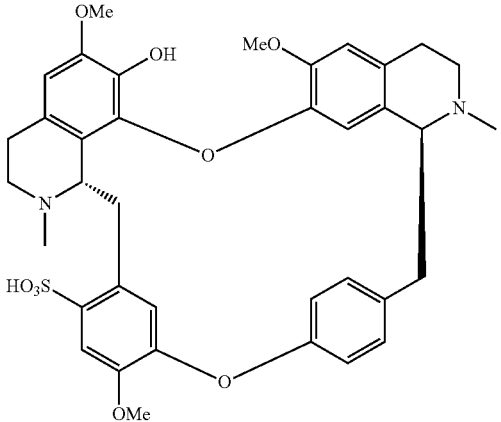

or

H-55

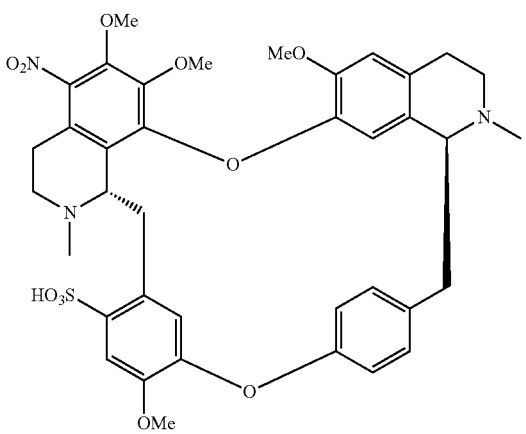

or a pharmaceutically acceptable salt thereof.

12. A pharmaceutical composition comprising a compound of claim 1, a single stereoisomer thereof, a mixture of stereoisomers thereof, or pharmaceutically acceptable salt thereof, and a pharmaceutically acceptable carrier.

13. A pharmaceutical composition according to claim 12 in the form of tablet, capsule, pill, suppository, cream, ointment, injection or infusion.

14. A pharmaceutical composition comprising a compound of claim 11, a single stereoisomer thereof, a mixture of stereoisomers thereof, or pharmaceutically acceptable salt and a pharmaceutically acceptable carrier.

* * * * *